US008609686B2

(12) United States Patent
Nell et al.

(10) Patent No.: US 8,609,686 B2
(45) Date of Patent: Dec. 17, 2013

(54) SUBSTITUTED AZABICYCLIC COMPOUNDS AND THE USE THEREOF

(75) Inventors: Peter Nell, Wuppertal (DE); Alexandros Vakalopoulos, Hilden (DE); Frank Süßmeier, Wuppertal (DE); Barbara Albrecht-Küpper, Wülfrath (DE); Katja Zimmerman, Düsseldorf (DE); Joerg Keldenich, Wuppertal (DE); Daniel Meibom, Leverkusen (DE)

(73) Assignee: Bayer Intellectual Property GmbH, Monheim (DE)

( * ) Notice: Subject to any disclaimer, the term of this patent is extended or adjusted under 35 U.S.C. 154(b) by 473 days.

(21) Appl. No.: 12/809,674

(22) PCT Filed: Dec. 9, 2008

(86) PCT No.: PCT/EP2008/010409
§ 371 (c)(1),
(2), (4) Date: Sep. 21, 2010

(87) PCT Pub. No.: WO2009/080197
PCT Pub. Date: Jul. 2, 2009

(65) Prior Publication Data
US 2011/0003845 A1    Jan. 6, 2011

(30) Foreign Application Priority Data
Dec. 20, 2007   (DE) .................. 10 2007 061 763

(51) Int. Cl.
| | | |
|---|---|---|
| *A01N 43/42* | (2006.01) |
| *A61K 31/44* | (2006.01) |
| *A01N 43/40* | (2006.01) |
| *C07D 471/02* | (2006.01) |
| *C07D 491/02* | (2006.01) |
| *C07D 498/02* | (2006.01) |
| *C07D 221/02* | (2006.01) |
| *C07D 401/00* | (2006.01) |
| *C07D 405/00* | (2006.01) |
| *C07D 409/00* | (2006.01) |
| *C07D 411/00* | (2006.01) |
| *C07D 413/00* | (2006.01) |
| *C07D 417/00* | (2006.01) |
| *C07D 419/00* | (2006.01) |
| *C07D 421/00* | (2006.01) |

(52) U.S. Cl.
USPC ........... 514/300; 514/333; 546/116; 546/183; 546/256

(58) Field of Classification Search
USPC ................. 514/300, 333; 546/116, 183, 256
See application file for complete search history.

(56) References Cited

U.S. PATENT DOCUMENTS

| | | |
|---|---|---|
| 4,052,510 A | 10/1977 | Simpson et al. |
| 5,670,525 A | 9/1997 | Urbahns et al. |
| 5,889,002 A | 3/1999 | Nielsen et al. |
| 6,191,280 B1 | 2/2001 | Hamprecht et al. |
| 6,586,441 B2 | 7/2003 | Barroni et al. |
| 6,632,823 B1 | 10/2003 | Vernier et al. |
| 6,693,102 B2 | 2/2004 | Stasch et al. |
| 6,706,717 B2 | 3/2004 | Barrish et al. |
| 6,743,798 B1 | 6/2004 | Straub et al. |
| 6,833,364 B1 | 12/2004 | Straub et al. |
| 6,864,287 B1 | 3/2005 | Alonso-Alija et al. |
| 7,045,631 B2 | 5/2006 | Rosentreter et al. |
| 7,078,417 B2 | 7/2006 | Rosentreter et al. |
| 7,109,218 B2 | 9/2006 | Rosentreter et al. |
| 7,129,255 B2 | 10/2006 | Rosentreter et al. |
| 7,135,486 B1 | 11/2006 | Rosentreter et al. |
| 7,173,036 B2 | 2/2007 | Sircar et al. |
| 7,173,037 B2 | 2/2007 | Alonso-Alija et al. |
| 7,186,716 B2 | 3/2007 | Wei et al. |
| 7,674,825 B2 | 3/2010 | Alonso-Alija et al. |
| 7,692,017 B2 | 4/2010 | Dinsmore et al. |
| 7,705,043 B2 | 4/2010 | Alonso-Alija et al. |
| 7,709,504 B2 | 5/2010 | Krahn et al. |
| 7,781,470 B2 | 8/2010 | Alonso-Alija et al. |
| 7,825,255 B2 | 11/2010 | Rosentreter et al. |
| 7,855,219 B2 | 12/2010 | Rosentreter et al. |
| 7,932,259 B2 | 4/2011 | Nakazato et al. |
| 7,951,811 B2 | 5/2011 | Nakazato et al. |
| 2003/0232860 A1 | 12/2003 | Harada et al. |
| 2004/0162427 A1 | 8/2004 | Rosentreter et al. |
| 2004/0176446 A1 | 9/2004 | Alonso-Alija et al. |
| 2005/0182105 A1 | 8/2005 | Nirschi et al. |
| 2005/0227972 A1 | 10/2005 | Rosentreter et al. |

(Continued)

FOREIGN PATENT DOCUMENTS

| | | |
|---|---|---|
| EP | 0 608 565 A1 | 12/1993 |
| JP | 09-132529 | 5/1997 |

(Continued)

OTHER PUBLICATIONS

Rattue, P. Medical News Today, Aug. 2011, pp. 1-4.*

(Continued)

*Primary Examiner* — Samira Jean-Louis

(74) *Attorney, Agent, or Firm* — Karen B. King; Thomas C. Blankinship

(57) ABSTRACT

The present application relates to novel substituted pyrrolopyridine, pyrazolopyridine and isoxazolopyridine derivatives, to processes for their preparation, to their use for the treatment and/or prevention of diseases and to their use for preparing medicaments for the treatment and/or prevention of diseases, preferably for the treatment and/or prevention of cardiovascular disorders.

10 Claims, No Drawings

(56) References Cited

U.S. PATENT DOCUMENTS

| | | | |
|---|---|---|---|
| 2005/0250774 | A1 | 11/2005 | Ono et al. |
| 2006/0264432 | A1 | 11/2006 | Rosentreter et al. |
| 2007/0066630 | A1 | 3/2007 | Palani et al. |
| 2007/0293670 | A1 | 12/2007 | Nakazato et al. |
| 2008/0167321 | A1 | 7/2008 | Kamboj et al. |
| 2008/0269300 | A1 | 10/2008 | Erguden et al. |
| 2009/0221649 | A1 | 9/2009 | Krahn et al. |
| 2010/0009973 | A1 | 1/2010 | Rhodes et al. |
| 2010/0022544 | A1 | 1/2010 | Nell et al. |
| 2010/0048641 | A1 | 2/2010 | Nell et al. |
| 2010/0069363 | A1 | 3/2010 | Nell et al. |
| 2010/0093728 | A1 | 4/2010 | Nell et al. |
| 2011/0046162 | A1 | 2/2011 | Nell et al. |
| 2011/0130377 | A1 | 6/2011 | Nell et al. |
| 2011/0136871 | A1 | 6/2011 | Hübsch et al. |
| 2011/0207698 | A1 | 8/2011 | Meibom et al. |
| 2011/0237629 | A1 | 9/2011 | Meibom et al. |
| 2011/0294718 | A1 | 12/2011 | Lerchen et al. |

FOREIGN PATENT DOCUMENTS

| | | |
|---|---|---|
| JP | 10-324687 | 12/1998 |
| JP | 2003-183254 | 7/2003 |
| WO | 95/34563 | 12/1995 |
| WO | 97/27177 A2 | 7/1997 |
| WO | 99/03861 A1 | 1/1999 |
| WO | 02/48115 A2 | 6/2002 |
| WO | 02/50071 A1 | 6/2002 |
| WO | 03/091246 | 11/2003 |
| WO | 2004/014372 A1 | 2/2004 |
| WO | 2004/054505 A2 | 7/2004 |
| WO | 2005/007647 | 1/2005 |
| WO | 2007/073855 | 7/2007 |
| WO | 2008/008059 | 1/2008 |

OTHER PUBLICATIONS

Zaragoza et al. J. of Biomedicine & Biotechnology, 2011, vol. 2011, pp. 1-13.*

Anand, et al.:"Novel Dipeptide Prodrugs of Acyclovir for Ocular Herpes Infections: Bioreversion, Antiviral Activity and Transport Across Rabbit Cornea," Current Eye Research, Mar. 2003, 26 (3-4):151-163.

Avila, et al.: A1-, A2A- and A3-subtype adenosine receptors modulate intraocular pressure in the mouse, British Journal of Pharmacology, 2001, 134:241-245.

Barnaby, et al.:"Structure-Activity Relationship Study of Prion Inhibition by 2-Aminopyridine-3,5-dicarbonitrile-Based Compounds: Parallel Synthesis, Bioactivity, and in Vitro Pharmacokinetics," J. Med. Chem., 2007, 50:65-73.

Barton et al.,:"Homologation of Acids via Carbon Radicals Generated from the Acyl Derivatives of N-Hydroxy-2-Thiopyrodine. (The Two-Carbon Problem)," Tetrahedron Letters, 1991, 32(28): 3309-3312.

Bauman:"Updating the Evidence that Physical Activity is Good for Health: An Epidemiological Review 2000-2003," J. Sci. Med. Sport, Apr. 2004, 7(1): Suppl:6-19.

Beaumont, et al.:"Design of Ester Prodrugs to Enhance Oral Absorption of Poorly Permeable Compounds: Challenges to the Discovery Scientist," Current Drug Metabolism, 2003, 4(6):461-485.

Beukers, et al.:"New, Non-Adenosine, High-Potency Agonists for the Human Adenosine A2B Receptor with an Improved Selectivity Profile Compared to the Reference Agonist N-Ethylcarboxamidoadenosine," Journal of Medicinal Chemistry, Jul. 15, 2004, 47(15): 3707-3709.

Bundgaard:"Design of Prodrugs: Bioreversible Derivatives for Various Functional Groups and Chemical Entities," Elsevier Science Publishers B.V. 1985, pp. 1092.

Castedo, et al.:"Synthesis and Pharmacological Activity of Some Nitrofuraldehyde Cyanopyridine Derivatives," Eur. J. Med. Chem., 1984, 19(6):555-557, abstract retrieved from CAPLUS Accession No. 1985:437337, EPO Document XP002202946.

Cesar, et al.:"Trimethylsilyldiazomethane in the Preparation of Diazoketonesvia Mixed Anhydride and Coupling Reagent Methods:A New Approach to the Arndt-Eistert Synthesis," Tetrahedron Letters, 2001, 42: 7099-7102.

Crosson: "Intraoccular Pressure Responses to the Adenosine Agonist Cyclohexyladenosine: Evidence for a Dual Mechanism of Action," IOVS, Jul. 2001, 42(8): 1837-1840.

Dhalla, et al.:"Pharmacology and Theraputic Applications of A1 Adenosine Receptor Ligands," Current Topics in Medicinal Chemisty, 2003, 3:369-385.

Dyachenko, et al.:"Single Stage Synthesis of 2-Alkylthio(seleno)-4-Hetaryl-3-cyano-5,6,7,8-Tetrahydroquinolines," Chemistry of Heterocyclic Compounds, 1997, 33(10): 1203-1208.

Dyachenko, et al.:"New Route to 6-Amino-4-aryl-3,5-dicyano-pyridine-2(1H)-thiones," Russian Journal of Organic Chemistry,1997, 33(7):1014-1017.

Dyachenko, et al.:"Michael Reaction in SyntheSis of 6-Amino-4-(4-Butoxyphenyl)-3,5- Dicyanopyridine-2(1H)-thionene," Chemistry of Heterocyclic Compounds, 1998, 34(2):188-194.

Dyachenko:"Cyclohexanecarbaldehyde in Multicomponent Syntheses of Functionalized Cyclohexyl-Substituted Acrylonitriles, 4H-Chalcogenopyrans, 1,4-Dihydropyridines, and Pyridines," Russian Journal of General Chemistry, 2006, 76(2):282-291.

Dyachenko, et al.,:"Synthesis and Recyclization of 4-Aryl-2,6-diamino-3,5-dicyano-4H-thiopyrans," Russian Journal of Organic Chemistry, 1998, 34(4): 557-563.

Eissa, et al.:"Synthesis and Biological Evaluation of Pyrido[2,3-d]pyrimidine as Antitumor Effect," Egypt. J. Chem., 2006, 49(6):761-774.

Elnagdi, et al.:"Studies with Polyfunctionally Substituted Heterocycles: Synthesis of New Pyridines, Naphtho[1,2-b] pyrans, Pyrazolo[3,4]pyridines and Pyrazolo[1,5-a]pyrimidines," Z. Naturforsch, 1992, 47b:572-578.

El-Torgoman, et al.:"Nitriles in Heterocyclic Synthesis: The reaction of 2-Thiocarbamoyl Cinnamonitriles with Active Methylene Reagents," Z. Naturforsch., 1987, 42b:107-111.

Ettmayer, et al.:"Lessons Learned from Marketed and Investigational Prodrugs," J. Med. Chem., May 6, 2004, 47(10) 2393-2404.

Fuentes, et al.:"Heterocycle Synthesis. XVI. Reaction of Malononitrile with Benzylidenemalononitriles in Presence of Amines." An. Quim., Ser. C., 1980, 76(1): 68-69, English language abstract retrieved from CAPLUS Accession No. 1981:139574, EPO Document No. XP002202947.

Goto, et al.:"Studies on Azole Compounds.III.1 Reactions of Oxazole N-Oxides with Phosphoryl Chloride and Acetic Anhydride 2", Chem. Pharm. Bull. 1971, 19: 2050-2057.

Ibrahim, et al.:"Synthesis and Biological Activity of Some New Heterocyclic Quinoline Derivatives," Phosphorus, Sulfer, and Silicon, 1991, 57: 293-301.

Jacobson, et al,:"Adenosine Receptors as Theraputic Targets," Nat. Rev. Drug Discover.,2005, 5:247-264.

Jacobson, et al.:"Adenosine Receptor Ligands: Differences with Acute Versus Chronic Treatment," Trends in Pharmacological Sciences, Mar. 1996, 17(3):108-113.

Kambe, et al.:"Synthetic Studies Using α,β-Unsaturated Nitriles: Facile Synthesis of Pyridine Derivatives," Synthesis Communications, Jul. 1981, pp. 531-533.

Klotz, et al.:"Comparative Pharmacology of Human Adenosine Receptor Subtypescharacterization of Stably Transfected Receptors in CHO Cells," Naunyn-Schmiedeberg's Arch Pharmacol, 1998, 357:1-9.

Klotz:"Adenosine Receptors and their Ligands," Naunyn-Schmiedeberg's Arch. Pharmacol., 2000, 362: 382-391.

Müller, et al.:"Adenosine Receptor Antagonists: Structures and Potential Therapeutic Applications," Current Pharmaceutical Design, 1996, 2:501-530.

Müller:"Adenosine Receptor Ligands-Recent Developments Part I. Agonists," Current Medicinal Chemistry, 2000, 7:1269-1288.

Müller:"Review. Cardiovascular & Renal. A1-Adenosine Receptor Antagonists," Exp. Opin. Ther. Patents, 1997, 7 (5):419-440.

(56) References Cited

OTHER PUBLICATIONS

Inotek Pharmaceuticals Press Release, "Inotek Pharmaceuticals Initiates Multiple-Dose Phase 2 Clinical Trial of INO-8875 in Patients with Glaucoma," Jun. 17, 2010.
Olah, et al.:"Cloning, Expression, and Characterization of the Unique Bovine A1 Adenosine Receptor," Journal of Biological Chemistry, May 25, 1992, 267(15):10764-10770.
Patani, et al.: "Bioisosterism: A Rational Approach in Drug Design," Chem. Rev., 1996, 96:3147-3176.
Pflueger, et al.:"Role of Adenosine in Contrast Media-Induced Acute Renal Failure in Diabetes Mellitus," Mayo Clin Proc., Dec. 2000, 75(12):1275-1283.
Poulsen, et al.:"Adenosine Receptors: New Opportunities for Future Drugs," Bioorganic & Medicinal Chemistry, Jan. 8, 1998, 6(6): 619-641.
Quintela, et al.:"Reactivity of Heterocyclic Compounds. V. Behavior of 6-alkoxy-2-amino-(or chloro)-4-aryl-3,5-dicyanopyridines in the Presence of Nucleophiles," Anales de Quimica, Serie C: Quimica Organica y Bioquimica, 1984, 80(3):268-72, English language abstract retrieved from CAPLUS Accession No. 1985:437345, CAPLUS Document No. 103:37345, EPO Document No. XP002202945.
Quintela, et al.:"Synthesis, Antihistaminic and Cytotoxic Activity of Pyridothieno- and Pyridodithienotriazines", Eur. J. Med. Chem, 1998, 33:887-897.
Rodinovskaya, et al.:"Substituted 4-(3-Cyanopyridin-2-ylthio)acetoacetates: New Convenient Reagents for the Synthesis of Heterocycles," Synthesis, 2006, (14): 2357-2370.
Rosenman:"Do Environmental Effects on Human Emotions Cause Cardiovascular Disorders?," Acta Physiologica Scandinavica, Supplement,1997, 161/640 (133-136), abstract retrieved from EMBASE Accession No. 97358868.
Ruhe, et al.:"Use of Antioxidant Nutrients in the Prevention and Treatment of Type 2 Diabetes," Journal of the American College of Nutrition, 2001, 20(5): 363S-369S.
Shams, et al.:"Nitriles in Organic Synthesis. New Routes for Synthesis of Pyridines and Azinothiopyrans," Journal fuer Praktische Chemie (Leipzig), 1988, 330(5):817-13, abstract retrieved from CAPLUS Accession No. 1989:497050.
Sheridan:"The Most Common Chemical Replacements in Drug-Like Compounds," J Chem. Inf. Comput. Sci., 2002, 42:103-108.
Suttner, et al.:"The Heart in the Elderly Critically Ill Patient," Curr. Opin. Crit. Care, Oct. 2002, 8(5):389-94, abstract retrieved from MEDLINE Accession No. 2002495386, PubMed ID: 12357105.
Szydlowski, et al.:"Biological Role of Chromium," Diabetologia Polska, 2003, 10(3):365-370, English language abstract retrieved from EMBASE Accession No. 2004016455.
Vasudevan A. et al., "Aminopiperidine indazoles as orally efficacious melanin concentrating hormone receptoer-1 antagonists," Bioorg. Med. Chem. Lett. 2005, 15 (23), 5293-5297.
Vippagunta, et al.:"Crystalline Solids," Advanced Drug Delivery Reviews, May 16, 2001, 48(1):3-26.
West:"Solid State Chemistry and its Applications," Wiley, New York, 1988, pp. 358 & 365.
Ye, et al.:Organic Synthesis with α-Diazocarbonyl Compounds, Chem. Rev. 1994, 94:1091-1160.
Yu, et al:"Physical Characterization of Polymorphic Drugs: An Integrated Characterization Strategy," Pharmaceutical Science & Technology Today, Jun. 1998, 1(3):118-127.
Zhu, G. et al., "Design and synthesis of pyridine-pyrazolopyridine-based inhibitors of protein kinase B/Akt," Bioorg. Med. Chem. 2007, 15 (6), 2441-2452.
U.S. Appl. No. 12/809,688, filed Sep. 20, 2010 published as US 2011-004162.
Clark, Kenneth, et al., "Potential of adenosine receptor agonists for the prevention and treatment of coronary artery disease and acute myocardial infarction," Emerging Drugs, 2000, 5(1):89-108.
Albrecht-Kopper, Barbara E, et al., "Partial adenosine A1 receptor agonists for cardiovascular tharapies.," Purinergic Signalling, 2012 8(Suppl 1): 891-899.

\* cited by examiner

SUBSTITUTED AZABICYCLIC COMPOUNDS AND THE USE THEREOF

The present application relates to novel substituted pyrrolopyridine, pyrazolopyridine and isoxazolopyridine derivatives, to processes for their preparation, to their use for the treatment and/or prevention of diseases and to their use for preparing medicaments for the treatment and/or prevention of diseases, preferably for the treatment and/or prevention of cardiovascular disorders.

Adenosine, a purine nucleoside, is present in all cells and is released by a large number of physiological and pathophysiological stimuli. Adenosine is formed intracellularly as an intermediate during the degradation of adenosine 5'-monophosphate (AMP) and S-adenosylhomocysteine, but it can be released from the cell, in which case it acts as a hormone-like substance or neurotransmitter by binding to specific receptors.

Under normoxic conditions, the concentration of free adenosine in the extracellular space is very low. However, under ischemic or hypoxic conditions, the extracellular concentration of adenosine in the affected organs increases dramatically. Thus, it is known, for example, that adenosine inhibits platelet aggregation and increases the blood supply to the coronary arteries. Furthermore, it acts on the blood pressure, on the heart rate, on the release of neurotransmitters and on lymphocyte differentiation. In adipocytes, adenosine is capable of inhibiting lipolysis, thus lowering the concentration of free fatty acids and triglycerides in the blood.

The aim of these actions of adenosine is to increase the oxygen supply of the affected organs and/or to reduce the metabolism of these organs in order to adjust the metabolism of the organ to the blood supply of the organ under ischemic or hypoxic conditions.

The action of adenosine is mediated via specific receptors. To date, subtypes A1, A2a, A2b and A3 are known. According to the invention, "adenosine-receptor-selective ligands" are substances which bind selectively to one or more subtypes of the adenosine receptors, thus being able either to mimic the action of adenosine (adenosine agonists) or to block its action (adenosine antagonists).

The actions of these adenosine receptors are mediated intracellularly by the messenger cAMP. In the case of the binding of adenosine to the A2a or A2b receptors, the intracellular cAMP increases via activation of the membrane-bound adenylate cyclase, whereas binding of adenosine to the A1 or A3 receptors results in a decrease in the intracellular cAMP concentration via inhibition of adenylate cyclase.

In the cardiovascular system, the main consequences of the activation of adenosine receptors are: bradycardia, negative inotropism and protection of the heart against ischemia ("preconditioning") via A1 receptors, dilation of the blood vessels via A2a and A2b receptors and inhibition of the fibroblasts and smooth-muscle-cell proliferation via A2b receptors.

In the case of A1 agonists (coupling preferably via $G_i$ proteins), a decrease of the intracellular cAMP concentration is observed (preferably after direct prestimulation of adenylate cyclase by forskolin). Correspondingly, A2a and A2b agonists (coupling preferably via $G_s$ proteins) leads to an increase and A2a and A2b antagonists to a decrease of the cAMP concentration in the cells. In the case of A2 receptors, a direct prestimulation of adenylate cyclase by forskolin is of no benefit.

In humans, activation of A1 receptors by specific A1 agonists leads to a frequency-dependent lowering of the heart rate, without any effect on blood pressure. Selective A1 agonists may thus be suitable inter alia for treating angina pectoris and atrial fibrillation. The cardioprotective action of the A1 receptors in the heart may be utilized inter alia by activating these A1 receptors with specific A1 agonists for treatment and organ protection in cases of acute myocardial infarction, acute coronary syndrome, heart failure, bypass operations, heart catheter examinations and organ transplantations.

The activation of A2b receptors by adenosine or specific A2b agonists leads, via dilation of blood vessels, to lowering of the blood pressure. The lowering of the blood pressure is accompanied by a reflectory increase in heart rate. The increase in heart rate can be reduced by activation of A1 receptors using specific A1 agonists.

The combined action of selective A1/A2b agonists on the vascular system and heart rate thus results in a systemic lowering of the blood pressure without relevant heart-rate increase. Dual A1/A2b agonists having such a pharmacological profile could be employed, for example, for treating hypertension in humans.

In humans, the inhibition of A1 receptors by specific A1 antagonists has a uricosuric, natriuretic and potassium-sparing diuretic effect without affecting the glomerular filtration rate, thus being renoprotective. Accordingly, selective A1 antagonists can be suitable inter alia for treating acute heart failure and chronic heart failure. Furthermore, they can be used for renoprotection in cases of nephropathy and other renal disorders.

In adipocytes, the activation of A1 and A2b receptors leads to an inhibition of lipolysis. Thus, the combined action of A1/A2b agonists on lipid metabolism results in a lowering of free fatty acids and triglycerides. In turn, in patients suffering from metabolic syndrome and in diabetics, reducing lipids leads to lower insulin resistance and improved symptoms.

The abovementioned receptor selectivity can be determined by the effect of the substances on cell lines which, after stable transfection with the corresponding cDNA, express the receptor subtypes in question (see the publication M. E. Olah, H. Ren, J. Ostrowski, K. A. Jacobson, G. L. Stiles, "Cloning, expression, and characterization of the unique bovine A1 adenosine receptor. Studies on the ligand binding site by site-directed mutagenesis", *J. Biol. Chem.* 267 (1992), pages 10764-10770, the disclosure of which is hereby fully incorporated by way of reference).

The effect of the substances on such cell lines can be studied by biochemical measurement of the intracellular messenger cAMP (see the publication K. N. Klotz, J. Hessling, J. Hegler, C. Owman, B. Kull, B. B. Fredholm, M. J. Lohse, "Comparative pharmacology of human adenosine receptor subtypes—characterization of stably transfected receptors in CHO cells", *Naunyn Schmiedebergs Arch. Pharmacol.* 357 (1998), pages 1-9, the disclosure of which is hereby fully incorporated by way of reference).

The "adenosine-receptor-specific" ligands known from the prior art are mainly derivatives based on natural adenosine [S.-A. Poulsen and R. J. Quinn, "Adenosine receptors: New opportunities for future drugs", *Bioorganic and Medicinal Chemistry* 6 (1998), pages 619-641]. However, these adenosine ligands known from the prior art usually have the disadvantage that their action is not really receptor-specific, that their activity is less than that of natural adenosine or that they have only very weak activity after oral administration. Thus, they are mainly used only for experimental purposes. Compounds of this type which are still in clinical development are hitherto only suitable for intravenous application.

WO 95/34563 describes substituted pyrazolo- and pyrrolopyridines as CRF antagonists for the treatment of stress-related disorders. WO 2004/014368 discloses 3-pyrrolylpyridopyrazoles and 3-pyrrolylindazoles as kinase inhibitors for the treatment of cancer. WO 2004/035740 claims substituted heterobicyclic compounds for the treatment of rheumatic arthritis, sepsis and multiple sclerosis, inter alia. WO 2004/058767, WO 2006/001501 and WO 2006/001511 disclose pyrrolopyridines and -pyrimidines as CRF ligands for the treatment of CNS disorders and hypertension.

It is an object of the present invention to provide novel compounds which act as selective ligands of the adenosine A1 and/or adenosine A2b receptor and as such for the treatment and/or prevention of diseases, in particular for the treatment and/or prevention of cardiovascular disorders.

The present invention provides compounds of the formula (I)

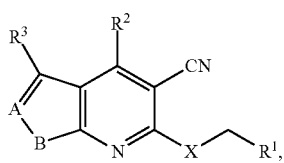

in which
either
A represents $CR^4$ or N,
where
$R^4$ represents $(C_1-C_4)$-alkoxycarbonyl, aminocarbonyl, mono-$(C_1-C_4)$-alkylaminocarbonyl or di-$(C_1-C_4)$-alkylaminocarbonyl,
and
B represents $NR^5$,
where
$R^5$ represents hydrogen or $(C_1-C_4)$-alkyl,
in which $(C_1-C_4)$-alkyl may be substituted by a $(C_1-C_4)$-alkoxycarbonyl substituent,
or
A represents N,
and
B represents O,
X represents O or S,
$R^1$ represents $(C_6-C_{10})$-aryl or 5- to 10-membered heteroaryl,
where $(C_6-C_{10})$-aryl and 5- to 10-membered heteroaryl may be substituted by 1 or 2 substituents independently of one another selected from the group consisting of halogen, nitro, cyano, $(C_1-C_6)$-alkyl, trifluoromethyl, hydroxyl, $(C_1-C_6)$-alkoxy, amino, mono-$(C_1-C_6)$-alkylamino, di-$(C_1-C_6)$-alkylamino, hydroxycarbonyl, $(C_1-C_6)$-alkoxycarbonyl, aminocarbonyl, mono-$(C_1-C_6)$-alkylaminocarbonyl, di-$(C_1-C_6)$-alkylaminocarbonyl, pyrrolidino, piperidino, morpholino, piperazino and N'—$(C_1-C_4)$-alkylpiperazino, phenyl and 5- or 6-membered heteroaryl,
in which phenyl and 5- or 6-membered heteroaryl may be substituted by 1 to 3 substituents independently of one another selected from the group consisting of halogen, nitro, cyano, $(C_1-C_6)$-alkyl, difluoromethyl, trifluoromethyl, hydroxyl, $(C_1-C_6)$-alkoxy, difluoromethoxy, trifluoromethoxy, amino, mono-$(C_1-C_6)$-alkylamino, di-$(C_1-C_6)$-alkylamino, hydroxycarbonyl and $(C_1-C_6)$-alkoxycarbonyl,
$R^2$ represents $(C_5-C_6)$-cycloalkyl, 5- or 6-membered heterocyclyl, phenyl or 5- or 6-membered heteroaryl,
where $(C_5-C_6)$-cycloalkyl may be substituted by 1 or 2 substituents independently of one another selected from the group consisting of $(C_1-C_6)$-alkyl, hydroxyl, oxo, $(C_1-C_6)$-alkoxy, amino, mono-$(C_1-C_6)$-alkylamino and di-$(C_1-C_6)$-alkylamino,
in which $(C_1-C_6)$-alkyl and $(C_1-C_6)$-alkoxy may be substituted by 1 or 2 substituents independently of one another selected from the group consisting of hydroxyl, $(C_1-C_4)$-alkoxy and $(C_3-C_7)$-cycloalkyl,
in which $(C_3-C_7)$-cycloalkyl for its part may be substituted by 1 or 2 substituents independently of one another selected from the group consisting of $(C_1-C_4)$-alkyl, hydroxyl, oxo and $(C_1-C_4)$-alkoxy,
and
where 5- or 6-membered heterocyclyl may be substituted by 1 to 3 substituents independently of one another selected from the group consisting of oxo, thioxo, hydroxyl, $(C_1-C_6)$-alkyl, $(C_1-C_6)$-alkoxy, $(C_1-C_6)$-alkylcarbonyl, amino, mono-$(C_1-C_6)$-alkylamino, di-$(C_1-C_6)$-alkylamino and $(C_3-C_7)$-cycloalkyl,
in which $(C_1-C_6)$-alkyl may be substituted by 1 to 3 substituents independently of one another selected from the group consisting of fluorine, oxo, hydroxyl, trifluoromethyl, $(C_1-C_4)$-alkoxy, $(C_1-C_4)$-alkylcarbonyloxy, amino, mono-$(C_1-C_4)$-alkylamino, di-$(C_1-C_4)$-alkylamino and $(C_3-C_7)$-cycloalkyl,
in which $(C_3-C_7)$-cycloalkyl for its part may be substituted by 1 or 2 substituents independently of one another selected from the group consisting of $(C_1-C_4)$-alkyl, hydroxyl, oxo and $(C_1-C_4)$-alkoxy,
and
in which $(C_1-C_6)$-alkylcarbonyl may be substituted by a substituent selected from the group consisting of hydroxyl and $(C_1-C_4)$-alkoxy,
and
in which $(C_3-C_7)$-cycloalkyl may be substituted by 1 or 2 substituents independently of one another selected from the group consisting of $(C_1-C_4)$-alkyl, hydroxyl, oxo and $(C_1-C_4)$-alkoxy,
and
where phenyl and 5- or 6-membered heteroaryl may be substituted by 1 to 3 substituents independently of one another selected from the group consisting of halogen, cyano, hydroxyl, $(C_1-C_6)$-alkyl, $(C_1-C_6)$-alkoxy, $(C_3-C_7)$-cycloalkoxy and —$NR^A R^B$,
in which $(C_1-C_6)$-alkyl may be substituted by 1 to 3 fluorine substituents,
and
in which $(C_1-C_6)$-alkoxy may be substituted by 1 to 3 substituents independently of one another selected from the group consisting of fluorine, trifluoromethyl, $(C_3-C_7)$-cycloalkyl, oxo, hydroxyl, $(C_1-C_4)$-alkoxy, hydroxycarbonyl, amino, mono-$(C_1-C_4)$-alkylamino and di-$(C_1-C_4)$-alkylamino,
and
in which $(C_3-C_7)$-cycloalkoxy may be substituted by 1 or 2 substituents independently of one another selected from the group consisting of $(C_1-C_4)$-alkyl, hydroxyl, oxo and $(C_1-C_4)$-alkoxy,
and
in which
$R^A$ represents hydrogen or $(C_1-C_6)$-alkyl,
in which $(C_1-C_6)$-alkyl for its part may be substituted by a substituent selected from the group consisting of hydroxyl and $(C_1-C_4)$-alkoxy,
$R^B$ represents hydrogen, $(C_1-C_6)$-alkyl, $(C_3-C_7)$-cycloalkyl, $(C_1-C_4)$-alkylsulfonyl or $(C_3-C_7)$-cycloalkylsulfonyl, in which $(C_1-C_6)$-alkyl for its part may be substituted by 1 or 2 substituents independently of one another selected from the group consisting of $(C_3-C_7)$-cycloalkyl, oxo, hydroxyl, $(C_1-C_4)$-alkoxy, hydroxycarbonyl, amino, mono-$(C_1-C_4)$-alkylamino and di-$(C_1-C_4)$-alkylamino, and in which $(C_3-C_7)$-cycloalkyl for its part may be substituted by 1 or 2 substituents independently of one another selected from the group consisting of $(C_1-C_4)$-alkyl, hydroxyl, oxo and $(C_1-C_4)$-alkoxy, or in which two adjacent substituents at the phenyl together with the carbon atoms to which they are attached may form a 1,3-dioxolane or 2,2-difluoro-1,3-dioxolane, $R^3$ represents hydrogen, $(C_1-C_4)$-alkyl, $(C_1-C_4)$-alkoxy, amino, mono-$(C_1-C_4)$-alkylamino, di-$(C_1-C_4)$-alkylamino or $(C_1-C_4)$-alkylcarbonyl and N-oxides, salts, solvates, salts of the N-oxides and solvates of the N-oxides and salts thereof.

Compounds according to the invention are the compounds of the formula (I) and the salts, solvates and solvates of the salts, the compounds which are encompassed by the formula (I) of the formulae mentioned below, and the salts, solvates and solvates of the salts thereof, and the compounds which are encompassed by formula (I) and are mentioned below as exemplary embodiments, and the salts, solvates and solvates of the salts thereof, where the compounds which are encompassed by the formula (I) and are mentioned below are not already salts, solvates and solvates of the salts.

The compounds according to the invention may, depending on their structure, exist in stereoisomeric forms (enantiomers, diastereomers). The invention therefore encompasses the enantiomers or diastereomers and respective mixtures thereof. The stereoisomerically pure constituents can be isolated from such mixtures of enantiomers and/or diastereomers in a known manner.

Where the compounds according to the invention can exist in tautomeric forms, the present invention encompasses all tautomeric forms.

Salts preferred for the purposes of the present invention are physiologically acceptable salts of the compounds according to the invention. Also included are salts which are not themselves suitable for pharmaceutical applications but can be used, for example, for the isolation or purification of the compounds according to the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid. Physiologically acceptable salts of the compounds according to the invention also include salts of conventional bases such as, by way of example and preferably, alkali metal salts (for example sodium and potassium salts), alkaline earth metal salts (for example calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. For the purposes of the present invention, preferred solvates are hydrates.

In addition, the present invention also encompasses prodrugs of the compounds according to the invention. The term "prodrugs" encompasses compounds which for their part may be biologically active or inactive but are converted (for example metabolically or hydrolytically) into compounds according to the invention during their residence time in the body.

For the purposes of the present invention, the substituents have the following meaning, unless specified otherwise:

Alkyl is in the context of the invention a straight-chain or branched alkyl radical having 1 to 6 or 1 to 4 carbon atoms. A straight-chain or branched alkyl radical having 1 to 4 carbon atoms is preferred. The following radicals may be mentioned by way of example and by way of preference: methyl, ethyl, n-propyl, isopropyl, n-butyl, isobutyl, sec-butyl, tert-butyl, 1-ethylpropyl, n-pentyl and n-hexyl.

Cycloalkyl is in the context of the invention a monocyclic saturated carbocycle having 3 to 7 or 5 or 6 ring carbon atoms. The following radicals may be mentioned by way of example and by way of preference: cyclopropyl, cyclobutyl, cyclopentyl, cyclohexyl and cycloheptyl.

Alkylcarbonyl is in the context of the invention a straight-chain or branched alkyl radical having 1 to 6 or 1 to 4 carbon atoms and a carbonyl group attached in position 1. The following radicals may be mentioned by way of example and by way of preference: methylcarbonyl, ethylcarbonyl, n-propylcarbonyl, isopropylcarbonyl, n-butylcarbonyl, isobutylcarbonyl and tert-butylcarbonyl.

Alkylcarbonyloxy is in the context of the invention a straight-chain or branched alkyl radical having 1 to 4 carbon atoms and, attached in position 1, a carbonyl group which is attached via an oxygen atom. The following radicals may be mentioned by way of example and by way of preference: methylcarbonyloxy, ethylcarbonyloxy, n-propylcarbonyloxy, isopropylcarbonyloxy and tert-butylcarbonyloxy.

Alkoxy is in the context of the invention a straight-chain or branched alkoxy radical having 1 to 6 or 1 to 4 or 2 to 4 carbon atoms. A straight-chain or branched alkoxy radical having 1 to 4 or 2 to 4 carbon atoms is preferred. The following radicals may be mentioned by way of example and by way of preference: methoxy, ethoxy, n-propoxy, isopropoxy, n-butoxy, tert-butoxy, n-pentoxy and n-hexoxy.

Cycloalkoxy is in the context of the invention a monocyclic saturated alkoxy radical having 3 to 7 carbon atoms. The following radicals may be mentioned by way of example and by way of preference: cyclopropyloxy, cyclobutyloxy, cyclopentyloxy, cyclohexyloxy and cycloheptyloxy.

Alkoxycarbonyl is in the context of the invention a straight-chain or branched alkoxy radical having 1 to 6 or 1 to 4 carbon atoms and a carbonyl group attached at the oxygen. A straight-chain or branched alkoxycarbonyl radical having 1 to 4 carbon atoms in the alkoxy group is preferred. The following radicals may be mentioned by way of example and by way of preference: methoxycarbonyl, ethoxycarbonyl, n-propoxycarbonyl, isopropoxycarbonyl and tert-butoxycarbonyl.

Monoalkylamino is in the context of the invention an amino group having a straight-chain or branched alkyl substituent having 1 to 6 or 1 to 4 or 2 to 4 carbon atoms. A straight-chain or branched monoalkylamino radical having 1 to 4 or 2 to 4 carbon atoms is preferred. The following radicals may be mentioned by way of example and by way of preference: methylamino, ethylamino, n-propylamino, isopropylamino, n-butylamino, tert-butylamino, n-pentylamino and n-hexylamino.

Dialkylamino is in the context of the invention an amino group having two identical or different straight-chain or branched alkyl substituents having 1 to 6 or 1 to 4 carbon atoms each. Straight-chain or branched dialkylamino radicals having 1 to 4 carbon atoms each are preferred. The following radicals may be mentioned by way of example and by way of preference: N,N-dimethylamino, N,N-diethylamino, N-ethyl-N-methyl-amino, N-methyl-N-n-propylamino, N-isopropyl-N-n-propylamino, N,N-diisopropylamino, N-n-butyl-N-methylamino, N-tert-butyl-N-methylamino, N-ethyl-N-n-pentylamino and N-n-hexyl-N-methylamino.

Monoalkylaminocarbonyl is in the context of the invention an amino group which is attached via a carbonyl group and has a straight-chain or branched alkyl substituent having 1 to 6 or 1 to 4 carbon atoms. A monoalkylaminocarbonyl radical having 1 to 4 carbon atoms in the alkyl group is preferred. The following radicals may be mentioned by way of example and by way of preference: methylaminocarbonyl, ethylaminocarbonyl, n-propylaminocarbonyl, isopropylaminocarbonyl, n-butylaminocarbonyl and tert-butylaminocarbonyl.

Dialkylaminocarbonyl is in the context of the invention an amino group which is attached via a carbonyl group and which has two identical or different straight-chain or branched alkyl substituents having 1 to 6 or 1 to 4 carbon atoms each. A dialkylaminocarbonyl radical having in each case 1 to 4 carbon atoms per alkyl group is preferred. The following radicals may be mentioned by way of example and by way of preference: N,N-dimethylaminocarbonyl, N,N-diethylaminocarbonyl, N-ethyl-N-methylaminocarbonyl, N-methyl-N-n-propylaminocarbonyl, N-n-butyl-N-methylaminocarbonyl and N-tert-butyl-N-methylaminocarbonyl.

Alkylsulfonyl is in the context of the invention a straight-chain or branched alkyl radical which has 1 to 4 carbon atoms and is attached via a sulfone group. The following radicals may be mentioned by way of example and by way of preference: methylsulfonyl, ethylsulfonyl, n-propylsulfonyl, isopropylsulfonyl, n-butylsulfonyl and tert-butylsulfonyl. Cycloalkylsulfonyl is in the context of the invention a monocyclic saturated alkyl radical which has 3 to 7 carbon atoms and is attached via a sulfone group. The following radicals may be mentioned by way of example and by way of preference: cyclopropylsulfonyl, cyclobutylsulfonyl, cyclopentylsulfonyl, cyclohexylsulfonyl and cycloheptylsulfonyl.

Heterocyclyl is in the context of the invention a saturated heterocycle having a total of 5 or 6 ring atoms which contains one or two ring heteroatoms from the group consisting of N, O and S and is attached via a ring carbon atom or, if appropriate, via a ring nitrogen atom. The following radicals may be mentioned by way of example: pyrrolidinyl, pyrazolidinyl, tetrahydrofuranyl, piperidinyl, piperazinyl, tetrahydropyranyl, morpholinyl and thiomorpholinyl. Pyrrolidinyl, tetrahydrofuranyl, piperidinyl, piperazinyl, tetrahydropyranyl and morpholinyl are preferred.

($C_6$-$C_{10}$)-Aryl is in the context of the invention an aromatic carbocycle having 6 or 10 ring carbon atoms. Preferred aryl radicals are phenyl and naphthyl.

Heteroaryl is in the context of the invention a mono- or optionally bicyclic aromatic heterocycle (heteroaromatic) which has a total of 5 to 10 ring atoms, contains up to three identical or different ring heteroatoms from the group consisting of N, O and S and is attached via a ring carbon atom or, if appropriate, via a ring nitrogen atom. The following radicals may be mentioned by way of example: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, indolyl, indazolyl, quinolinyl, isoquinolinyl, naphthyridinyl, quinazolinyl, quinoxalinyl, phthalazinyl, pyrazolo[3,4-b]pyridinyl. Monocyclic 5- or 6-membered heteroaryl radicals having up to three ring heteroatoms from the group consisting of N, O and S, such as, for example, furyl, thienyl, thiazolyl, oxazolyl, isothiazolyl, isoxazolyl, pyrazolyl, imidazolyl, triazolyl, oxadiazolyl, thiadiazolyl, pyridyl, pyrimidinyl, pyridazinyl, pyrazinyl, triazinyl, are preferred.

Halogen includes in the context of the invention fluorine, chlorine, bromine and iodine. Preference is given to chlorine or fluorine.

When radicals in the compounds according to the invention are substituted, the radicals may be mono- or polysubstituted, unless specified otherwise. For the purposes of the present invention, the meanings of all radicals which occur more than once are independent of one another. Preference is given to substitution by one, two or three identical or different substituents. Very particularly preferred is substitution by one or two identical or different substituents.

In the context of the present invention, preference is given to compounds of the formula (I) in which A represents $CR^4$ or N, where $R^4$ represents ($C_1$-$C_4$)-alkoxycarbonyl, aminocarbonyl or mono-($C_1$-$C_4$)-alkylaminocarbonyl, and B represents $NR^5$, where $R^5$ represents hydrogen, methyl or ethyl, in which methyl and ethyl may be substituted by a substituent selected from the group consisting of methoxycarbonyl and ethoxycarbonyl, X represents O or S, $R^1$ represents phenyl or 5- or 6-membered heteroaryl, where phenyl and 5- or 6-membered heteroaryl may be substituted by 1 or 2 substituents independently of one another selected from the group consisting of fluorine, chlorine, cyano, ($C_1$-$C_4$)-alkyl, trifluoromethyl, hydroxyl, ($C_1$-$C_4$)-alkoxy, amino, hydroxycarbonyl, ($C_1$-$C_4$)-alkoxycarbonyl, aminocarbonyl, phenyl and 5- or 6-membered heteroaryl, in which phenyl and 5- or 6-membered heteroaryl may be substituted by 1 to 3 substituents independently of one another selected from the group consisting of fluorine, chlorine, nitro, cyano, ($C_1$-$C_4$)-alkyl, difluoromethyl, trifluoromethyl, hydroxyl, methoxy, ethoxy, amino, hydroxycarbonyl and ($C_1$-$C_4$)-alkoxycarbonyl, $R^2$ represents cyclohexyl, tetrahydropyranyl, piperidinyl, piperazinyl, morpholinyl, phenyl, pyrazolyl, imidazolyl, oxazolyl, thiazolyl or pyridyl, where cyclohexyl may be substituted by a substituent selected from the group consisting of hydroxyl and ($C_1$-$C_4$)-alkoxy, in which $(C_2-C_4)$-alkoxy may be substituted by 1 or 2 substituents independently of one another selected from the group consisting of hydroxyl and methoxy, and where piperidinyl, piperazinyl and morpholinyl may be substituted by a substituent selected from the group consisting of $(C_1-C_4)$-alkyl, hydroxyl, $(C_1-C_4)$-alkoxy and $(C_1-C_4)$-alkylcarbonyl, in which $(C_1-C_4)$-alkyl may be substituted by 1 or 2 substituents independently of one another selected from the group consisting of hydroxyl, methoxy, ethoxy, methylcarbonyloxy and ethylcarbonyloxy, and in which $(C_1-C_4)$-alkylcarbonyl may be substituted by a substituent selected from the group consisting of hydroxyl, methoxy and ethoxy, and where phenyl and pyridyl may be substituted by 1 to 3 substituents independently of one another selected from the group consisting of fluorine, chlorine, cyano, hydroxyl, $(C_1-C_4)$-alkyl and $(C_1-C_4)$-alkoxy, in which $(C_2-C_4)$-alkoxy may be substituted by 1 or 2 substituents independently of one another selected from the group consisting of oxo, hydroxyl, $(C_1-C_4)$-alkoxy, hydroxycarbonyl and amino, and where pyrazolyl, imidazolyl, oxazolyl and thiazolyl may be substituted by 1 or 2 substituents independently of one another selected from the group consisting of fluorine, chlorine, cyano, hydroxyl, $(C_1-C_4)$-alkyl and $(C_1-C_4)$-alkoxy, in which $(C_2-C_4)$-alkoxy may be substituted by 1 or 2 substituents independently of one another selected from the group consisting of oxo, hydroxyl, $(C_1-C_4)$-alkoxy, hydroxycarbonyl and amino, $R^3$ represents hydrogen, amino, methylamino or dimethylamino, and salts, solvates and solvates of the salts thereof.

In the context of the present invention, preference is also given to compounds of the formula (I) in which A represents $CR^4$ or N, where $R^4$ represents $(C_1-C_4)$-alkoxycarbonyl, aminocarbonyl or mono-$(C_1-C_4)$-alkylaminocarbonyl, and B represents $NR^5$, where $R^5$ represents hydrogen, methyl or ethyl, in which methyl and ethyl may be substituted by a substituent selected from the group consisting of methoxycarbonyl and ethoxycarbonyl, X represents O or S, $R^1$ represents phenyl or 5- or 6-membered heteroaryl, where phenyl and 5- or 6-membered heteroaryl may be substituted by 1 or 2 substituents independently of one another selected from the group consisting of fluorine, chlorine, cyano, $(C_1-C_4)$-alkyl, trifluoromethyl, hydroxyl, $(C_1-C_4)$-alkoxy, amino, hydroxycarbonyl, $(C_1-C_4)$-alkoxycarbonyl, aminocarbonyl, phenyl and 5- or 6-membered heteroaryl, in which phenyl and 5- or 6-membered heteroaryl may be substituted by 1 to 3 substituents independently of one another selected from the group consisting of fluorine, chlorine, nitro, cyano, $(C_1-C_4)$-alkyl, difluoromethyl, trifluoromethyl, hydroxyl, methoxy, ethoxy, amino, hydroxycarbonyl and $(C_1-C_4)$-alkoxycarbonyl, $R^2$ represents a group of the formula

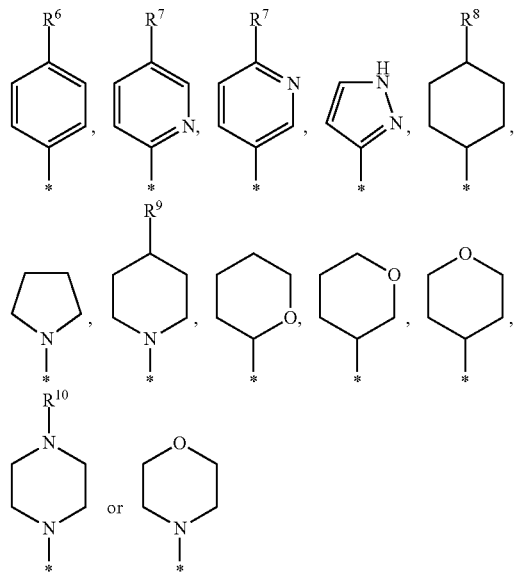

where

* represents the point of attachment to the bicycle, $R^6$ represents hydrogen or $(C_1-C_4)$-alkoxy, in which $(C_2-C_4)$-alkoxy may be substituted by 1 or 2 hydroxyl substituents, $R^7$ represents hydrogen or $(C_1-C_4)$-alkoxy, in which $(C_2-C_4)$-alkoxy may be substituted by 1 or 2 hydroxyl substituents, $R^8$ represents hydrogen, hydroxyl, methoxy, ethoxy or 2-hydroxyethoxy, $R^9$ represents hydrogen or hydroxyl, and $R^{10}$ represents hydrogen or methyl, $R^3$ represents hydrogen, amino, methylamino or dimethylamino, and salts, solvates and solvates of the salts thereof.

In the context of the present invention, particular preference is given to compounds of the formula (I) in which A represents $CR^4$ or N, where $R^4$ represents methoxycarbonyl, aminocarbonyl or methylaminocarbonyl, and B represents $NR^5$, where $R^5$ represents hydrogen or methyl, in which methyl may be substituted by a methoxycarbonyl substituent, X represents O or S, $R^1$ represents thiazolyl, oxazolyl, phenyl or pyridyl, where phenyl and pyridyl may be substituted by 1 or 2 substituents independently of one another selected from the group consisting of fluorine, chlorine, cyano, methyl, ethyl, methoxy, amino, hydroxycarbonyl, methoxycarbonyl, ethoxycarbonyl and aminocarbonyl, and where thiazolyl and oxazolyl are substituted by a phenyl group substituent, in which phenyl may be substituted by a substituent selected from the group consisting of fluorine, chlorine, cyano, methyl, methoxy and hydroxycarbonyl, and
where thiazolyl and oxazolyl may be substituted by a substituent selected from the group consisting of fluorine, chlorine, cyano, methyl, ethyl, methoxy, amino, hydroxycarbonyl, methoxycarbonyl, ethoxycarbonyl and aminocarbonyl, $R^2$ represents a group of the formula

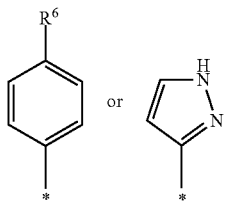

where
* represents the point of attachment to the bicycle,
$R^6$ represents hydrogen or $(C_1-C_4)$-alkoxy,
in which $(C_2-C_4)$-alkoxy may be substituted by 1 or 2 hydroxyl substituents,
$R^3$ represents amino,
and salts, solvates and solvates of the salts thereof.

In the context of the present invention, preference is also given to compounds of the formula (I) in which
$R^2$ represents a compound of the formula

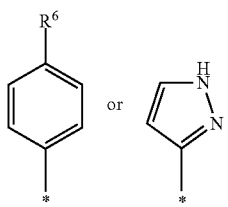

where
* represents the point of attachment to the bicycle,
$R^6$ represents hydrogen or $(C_1-C_4)$-alkoxy,
in which $(C_2-C_4)$-alkoxy may be substituted by 1 or 2 hydroxyl substituents.

In the context of the present invention, preference is also given to compounds of the formula (I) in which
$R^1$ represents thiazolyl, oxazolyl, phenyl or pyridyl,
where phenyl and pyridyl may be substituted by 1 or 2 substituents independently of one another selected from the group consisting of fluorine, chlorine, cyano, methyl, ethyl, methoxy, amino, hydroxycarbonyl, methoxycarbonyl, ethoxycarbonyl and aminocarbonyl,
and
where thiazolyl and oxazolyl are substituted by phenyl,
in which phenyl may be substituted by a substituent selected from the group consisting of fluorine, chlorine, cyano, methyl, methoxy and hydroxycarbonyl,
and/or
where thiazolyl and oxazolyl may be substituted by a substituent selected from the group consisting of fluorine, chlorine, cyano, methyl, ethyl, methoxy, amino, hydroxycarbonyl, methoxycarbonyl, ethoxycarbonyl and aminocarbonyl.

In the context of the present invention, preference is also given to compounds of the formula (I) in which $R^3$ represents amino.

The present invention furthermore provides a process for preparing the compounds of the formula (I) according to the invention in which $R^3$ represents amino, characterized in that a compound of the formula (II)

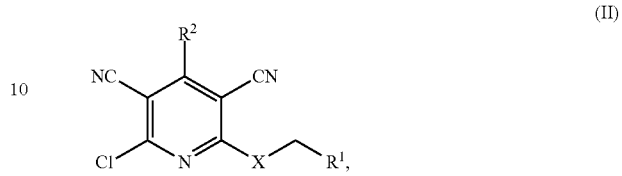

in which X, $R^1$ and $R^2$ each have the meanings given above,
[A] is reacted in an inert solvent in the presence of a suitable base with a compound of the formula (III-A)

in which $R^4$ and $R^5$ each have the meanings given above,
to give a compound of the formula (IV-A)

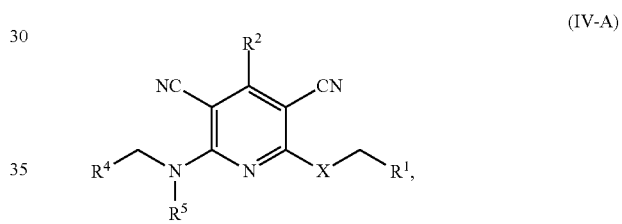

in which X, $R^1$, $R^2$, $R^4$ and $R^5$ each have the meanings given above,
and this is then cyclized in an inert solvent and in the presence of a suitable base to give compounds of the formula (I-A)

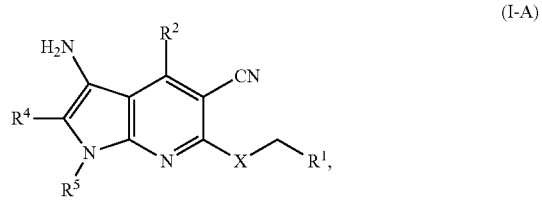

in which X, $R^1$, $R^2$, $R^4$ and $R^5$ each have the meanings given above,
or
[B] is cyclized in an inert solvent in the presence of a suitable base with a compound of the formula (III-B)

in which R⁵ has the meaning given above,
to give compounds of the formula (I-B)

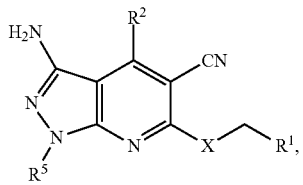

in which X, R¹, R² and R⁵ each have the meanings given above,
or

[C] is reacted in an inert solvent in the presence of a suitable base with the compound of the formula (III-C)

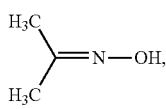

to give a compound of the formula (IV-C)

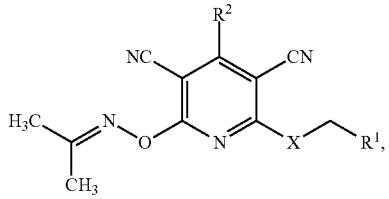

in which X, R¹ and R² each have the meanings given above, and this is then cyclized in a suitable solvent in the presence of a suitable base to give compounds of the formula (I-C)

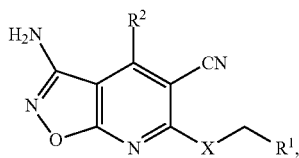

in which X, R¹ and R² each have the meanings given above,
any protective groups present are then cleaved off and the resulting compounds of the formulae (I-A), (I-B) and (I-C) are, if appropriate, converted with the appropriate (i) solvents and/or (ii) bases or acids into their solvates, salts and/or solvates of the salts. Any functional groups which may be present in the compounds of the formula (II) or in the radical R²—such as, in particular, amino, hydroxyl and carboxyl groups—may in this process, if expedient or required, also be present in temporarily protected form. The introduction and removal of such protective groups takes place in this connection by conventional methods known to those skilled in the art [see, for example, T. W. Greene and P. G. M. Wuts, *Protective Groups in Organic Synthesis*, Wiley, New York, 1999; M. Bodanszky and A. Bodanszky, *The Practice of Peptide Synthesis*, Springer-Verlag, Berlin, 1984]. If a plurality of protective groups is present, the removal may optionally be carried out simultaneously in a one-pot reaction or in separate reaction steps.

The compounds of the formulae (III-A), (III-B) and (III-C) are commercially available, known from the literature, or they can be prepared analogously to processes known from the literature.

The process described above can be illustrated by Reaction Schemes 1 to 3 below:

Scheme 1

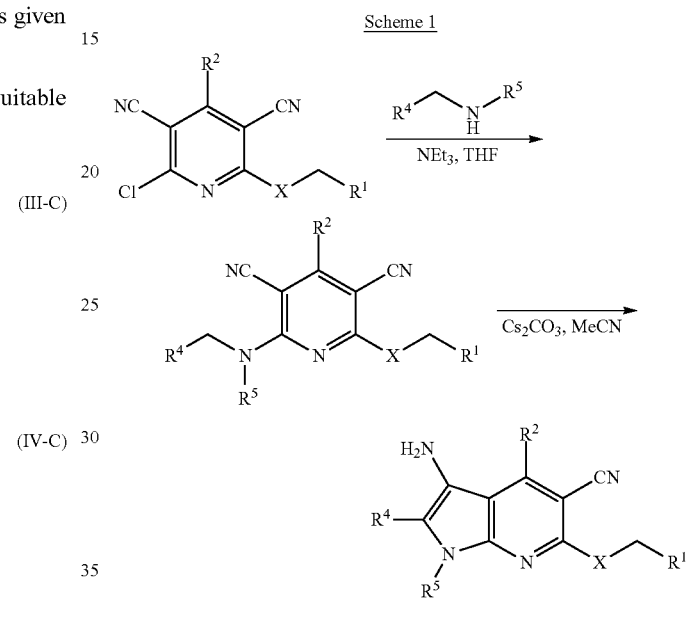

Scheme 2

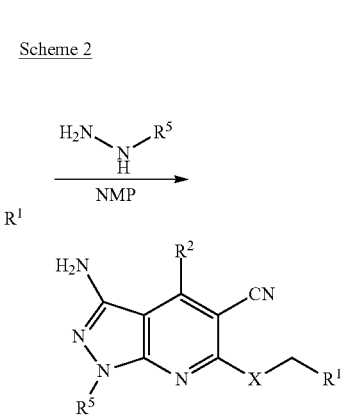

Scheme 3

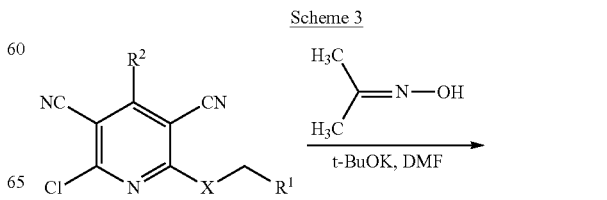

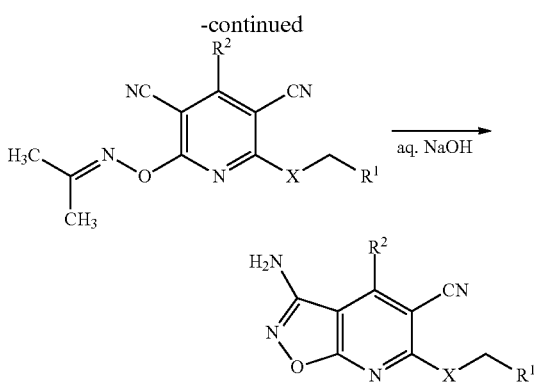

Inert solvents for the reactions (II)+(III-A)→(IV-A), (IV-A)→(I-A), (II)+(III-B)→(I-B), (II)+(III-C)→(IV-C) are, for example, alcohols, such as methanol, ethanol, n-propanol, isopropanol, n-butanol and tert-butanol, ketones, such as acetone and methyl ethyl ketone, acyclic and cyclic ethers, such as diethyl ether, methyl tert-butyl ether, 1,2-di-methoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, trichloromethane and chlorobenzene, or other solvents, such as dimethylformamide (DMF), dimethyl sulfoxide (DMSO), N-methylpyrrolidinone (NMP), acetonitrile, pyridine or water. It is also possible to use mixtures of the solvents mentioned above. Preference is given to using dimethyl-formamide, acetonitrile, tetrahydrofuran or dioxane as solvent.

Suitable bases for the reaction (II)+(III-A)→(IV-A)→(I-A) are the customary inorganic or organic bases. These preferably include alkali metal hydroxides, such as lithium-hydroxide, sodium hydroxide or potassium hydroxide, alkali metal carbonates, such as lithium carbonate, sodium carbonate, potassium carbonate or cesium carbonate, alkali metal bicarbonates, such as sodium bicarbonate or potassium bicarbonate, alkali metal alkoxides, such as sodium methoxide or potassium methoxide, sodium ethoxide or potassium ethoxide or potassium tert-butoxide, or amides, such as sodium amide, lithium bis(trimethylsilyl)amide, sodium bis(trimethylsilyl)amide or potassium bis(trimethylsilyl)amide or lithium diisopropylamide, organometallic compounds, such as butyllithium or phenyllithium, organic amines, such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to triethylamine and alkali metal carbonates.

Inert solvents for the reactions (IV-C)→(I-C) are, for example, alcohols, such as methanol, ethanol, n-propanol, isopropanol, n-butanol and tert-butanol, ketones, such as acetone and methyl ethyl ketone, ethers, such as 1,2-dimethoxyethane, tetrahydrofuran and dioxane, hydrocarbons, such as benzene, toluene, xylene, hexane and cyclohexane, chlorinated hydrocarbons, such as dichloromethane, trichloromethane and chlorobenzene, other solvents, such as dimethylformamide (DMF), dimethyl sulfoxide (DMSO), N-methylpyrrolidinone (NMP), acetonitrile or pyridine, or water. It is also possible to use mixtures of the solvents mentioned above. Preference is given to using water as solvent.

Suitable bases for the reaction (II)+(III-C)→(IV-C) and (IV-C)→(I-C) are the customary inorganic or organic bases. These preferably include alkali metal hydroxides, such as lithium hydroxide, sodium hydroxide or potassium hydroxide, alkali metal alkoxides, such as sodium methoxide or potassium methoxide, sodium ethoxide or potassium ethoxide or potassium tert-butoxide, amides, such as sodium amide, lithium bis(trimethylsilyl)amide, sodium bis(trimethylsilyl)amide or potassium bis(trimethylsilyl)-amide or lithium diisopropylamide, or organometallic compounds, such as butyllithium or phenyllithium. Preference is given to alkali metal alkoxides and alkali metal hydroxides. Here, the base can be employed in an amount of from 1 to 10 mol, preferably from 1 to 5 mol, in particular from 1 to 4 mol, based on 1 mol of the compound of the formula (II). The reactions are generally carried out in a temperature range of from −78° C. to +140° C., preferably in the range from −20° C. to +80° C., in particular at from 0° C. to +50° C., if appropriate in a microwave. The reaction can be carried out at atmospheric, elevated or reduced pressure (for example in the range from 0.5 to 5 bar). The reactions are generally carried out at atmospheric pressure.

Further compounds according to the invention can be prepared from the compounds of the formula (I) obtained by the above processes in which $R^3$ represents amino by converting these analogously to the process described in Ortega, M. A. et al., *Bioorg. Med. Chem.* 2002, 10 (7), 2177-2184 into compounds of the formula (V),

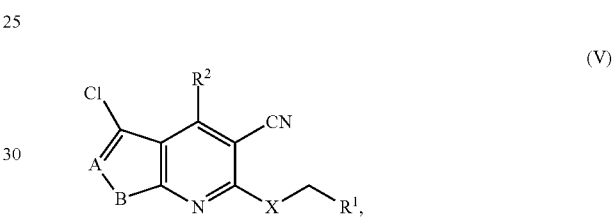

in which A, B, X, $R^1$ and $R^2$ each have the meanings given above, and then reacting these compounds further analogously to processes known from the literature [cf. Fischer E. et al., *Chem. Ber.* 1901, 34, 798; Zhu, G. et al., *Bioorg. Med. Chem.* 2007, 15 (6), 2441-2452; Vasudevan A. et al., *Bioorg. Med. Chem. Lett.* 2005, 15 (23), 5293-5297; Pillai P. et al., *Indian J. Chem. Sect. B,* 1989, 28, 1026-1030].

Other compounds according to the invention can, if appropriate, also be prepared from the compounds, obtained by the above processes, of the formula Formel (I) by converting functional groups of individual substituents, in particular those listed under $R^2$, $R^3$, $R^4$ and $R^5$. These conversions are carried out by customary methods customary methods known to the person skilled in the art and include, for example, reactions such as nucleophilic and electrophilic substitutions, oxidations, reductions, hydrogenations, transition metal-catalyzed coupling reactions, eliminations, alkylation, amination, esterification, ester cleavage, etherification, ether cleavage, formation of carboxamides, and also the introduction and removal of temporary protective groups.

The compounds of the formula (II) can be prepared by reacting a compound of the formula (VI)

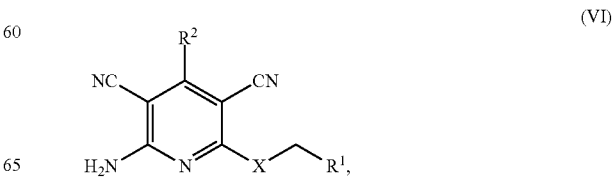

in which X, $R^1$ and $R^2$ each have the meanings given above,
in an inert solvent with copper(II) chloride and isopentyl nitrite.

The process described above can be illustrated by the Reaction Scheme below:

Scheme 4

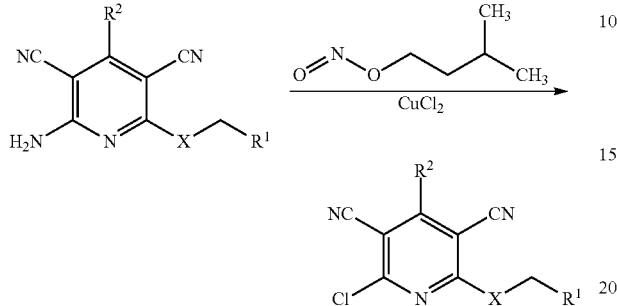

The reaction (VI)→(II) is generally carried in a molar ratio of from 2 to 12 mol of copper(II) chloride and 2 to 12 mol of isopentyl nitrite, based on 1 mol of the compound of the formula (VI).

Suitable solvents for the process step (VI)→(II) are all organic solvents which are inert under the reaction conditions. These include acyclic and cyclic ethers, such as diethyl ether and tetrahydrofuran, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or other solvents, such as dimethyl sulfoxide (DMSO), dimethylformamide, acetonitrile or pyridine. It is also possible to use mixtures of the solvents mentioned above. Preferred solvents are acetonitrile and dimethylformamide.

The reaction is generally carried out in a temperature range of from −78° C. to +180° C., preferably in the range from 0° C. to +100° C., in particular at from +20° C. to +80° C., if appropriate in a microwave. The reaction can be carried out at atmospheric, elevated or reduced pressure (for example in the range from 0.5 to 5 bar). The reaction is generally carried out at atmospheric pressure.

Compounds of the formula (VI) in which X represents S can be prepared by reacting a compound of the formula (VII-A)

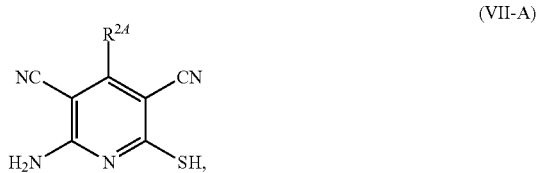

in which
$R^{2A}$ represents ($C_5$-$C_6$)-cycloalkyl, 5- or 6-membered heterocyclyl which is attached via carbon, phenyl or 5- or 6-membered heteroaryl which is attached via carbon,
each of which may be substituted as described above under $R^2$, in an inert solvent in the presence of a base with a compound of the formula (VIII)

in which $R^1$ has the meaning given above, and
Q represents a suitable leaving group, preferably halogen, in particular chlorine, bromine or iodine, or represents mesylate, tosylate or triflate,
to give compounds of the formula (VI-A)

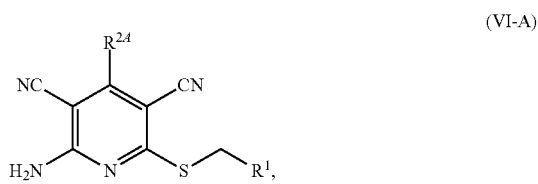

in which $R^1$ and $R^{2A}$ each have the meanings given above.

The compounds of the formula (VIII) are commercially available, known from the literature, or they can be prepared by methods known from the literature. Thus, substituted oxazole and thiazole derivatives of the formulae (VIII-A) and (VIII-B) can be obtained, for example, by reaction of amides or thioamides with a 1,3-dihaloacetone (see Scheme 5):

Scheme 5

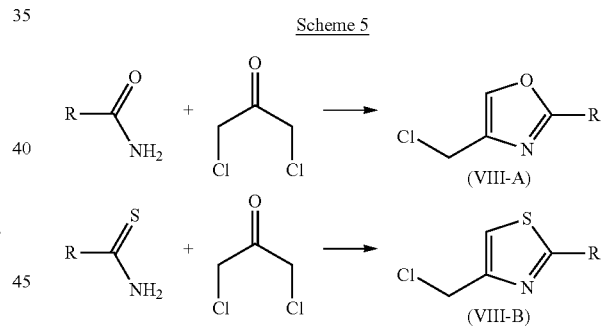

Inert solvents for the reaction (VII-A)+(VIII)→(VI-A) are, for example, alcohols, such as methanol, ethanol, n-propanol, isopropanol, n-butanol and tert-butanol, ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, trichloromethane and chlorobenzene, or other solvents, such as dimethylformamide (DMF), dimethyl sulfoxide (DMSO), N-methylpyrrolidinone (NMP), acetonitrile or pyridine. Another suitable solvent is water. It is also possible to use mixtures of the solvents mentioned above. Preference is given to using dimethylformamide as solvent. Suitable bases for the reaction (VII-A)+(VIII)→(VI-A) are the customary inorganic or organic bases. These preferably include alkali metal hydroxides, such as lithium-hydroxide, sodium hydroxide or potassium hydroxide, alkali metal carbonates, such as lithium carbonate, sodium carbonate, potassium carbonate or cesium carbonate, alkali metal bicarbonates, such as sodium bicarbonate or potassium bicarbonate, alkali metal alkoxides, such as sodium methoxide or potassium methoxide, sodium ethoxide or potassium ethoxide or potassium tert-butoxide, amides, such as sodium amide, lithium bis(trimethylsilyl)amide, sodium bis(trimethylsilyl)amide or potassium bis(trimethylsilyl)-amide or lithium diisopropylamide, organometallic compounds, such as butyllithium or phenyllithium, or organic amines, such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to alkali metal carbonates and alkali metal bicarbonates.

Here, the base can be employed in an amount of from 1 to 10 mol, preferably from 1 to 5 mol, in particular from 1 to 4 mol, based on 1 mol of the compound of the formula (II). The reaction is generally carried out in a temperature range of from −78° C. to +140° C., preferably in the range from −20° C. to −80° C., in particular at from 0° C. to +50° C., if appropriate in a microwave. The reaction can be carried out at atmospheric, elevated or reduced pressure (for example in the range from 0.5 to 5 bar). The reaction is generally carried out at atmospheric pressure.

Compounds of the formula (VII-A) can be prepared analogously to methods known from the literature, for example by reacting aldehydes of the formula (IX)

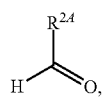

(IX)

in which $R^{2A}$ has the meaning given above, in the presence of a base with two equivalents of cyanothioacetamide [cf., for example, Dyachenko et al., *Russ. J. Chem.* 33 (7), 1014-1017 (1997), 34 (4), 557-563 (1998); Dyachenko et al., *Chemistry of Heterocyclic Compounds* 34 (2), 188-194 (1998); Qintela et al., *Eur. J. Med. Chem.* 33, 887-897 (1998); Kandeel et al., *Z. Naturforsch.* 42b, 107-111 (1987); Reddy et al., *J. Med. Chem.* 49, 607-615 (2006); Evdokimov et al., *Org. Lett.* 8, 899-902 (2006)].

The compounds of the formula (IX) are commercially available, known from the literature, or they can be prepared analogously to processes known from the literature. Further compounds of the formula (VI) in which X represents S can be prepared by converting the compound of the formula (X)

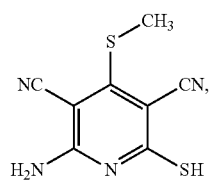

(X)

in an inert solvent in the presence of a base with a compound of the formula (VIII) into a compound of the formula (XI)

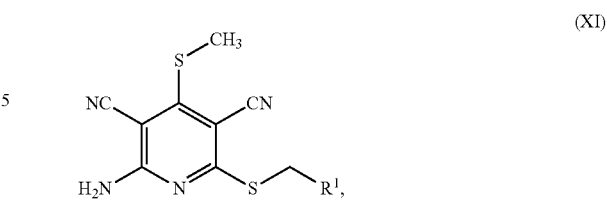

(XI)

in which $R^1$ has the meaning given above, and then reacting this compound in an inert solvent or in the absence of a solvent with a compound of the formula (XII)

$$R^{2B}-H \qquad (XII),$$

in which $R^{2B}$ represents 5- or 6-membered heterocyclyl attached via nitrogen or 5- or 6-membered heteroaryl attached via nitrogen, each of which may be substituted as described above for $R^2$, to give compounds of the formula (VI-B)

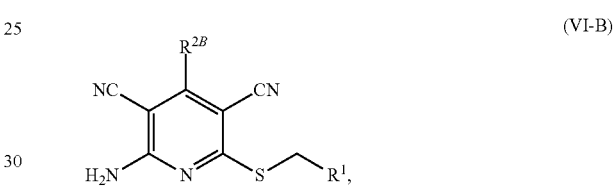

(VI-B)

in which $R^1$ and $R^{2B}$ each have the meanings given above.

Suitable solvents for the process step (X)+(VIII)→(XI) are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, trichloromethane and chlorobenzene, or other solvents, such as dimethylformamide (DMF), dimethyl sulfoxide (DMSO), N-methylpyrrolidinone (NMP), acetonitrile or pyridine. Another suitable solvent is water. It is also possible to use mixtures of the solvents mentioned above. Preference is given to using dimethylformamide as solvent.

Suitable bases for the process step (X)+(VIII)→(XI) are the customary inorganic or organic bases. These preferably include alkali metal hydroxides, such as lithium-hydroxide, sodium hydroxide or potassium hydroxide, alkali metal carbonates, such as lithium carbonate, sodium carbonate, potassium carbonate or cesium carbonate, alkali metal bicarbonates, such as sodium bicarbonate or potassium bicarbonate, alkali metal alkoxides, such as sodium methoxide or potassium methoxide, sodium ethoxide or potassium ethoxide or potassium tert-butoxide, amides, such as sodium amide, lithium bis(trimethylsilyl)amide, sodium bis(trimethylsilyl)amide or potassium bis(trimethylsilyl)-amide or lithium diisopropylamide, organometallic compounds, such as butyllithium or phenyllithium, or organic amines, such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to alkali metal carbonates and alkali metal bicarbonates.

Here, the base can be employed in an amount of from 1 to 10 mol, preferably from 1 to 5 mol, in particular from 1 to 4 mol, based on 1 mol of the compound of the formula (II). The reaction is generally carried out in a temperature range of from −78° C. to +140° C., preferably in the range from −20° C. to +80° C., in particular at from 0° C. to +50° C., if appropriate in a microwave. The reaction can be carried out at atmospheric, elevated or reduced pressure (for example in the range from 0.5 to 5 bar). The reaction is generally carried out at atmospheric pressure.

Suitable solvents for the process step (XI)+(XII)→(VI-B) are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane or chlorobenzene, or other solvents, such as dimethylformamide (DMF), dimethyl sulfoxide (DMSO), N-methylpyrrolidinone (NMP), acetonitrile or pyridine. Another suitable solvent is water. It is also possible to use mixtures of the solvents mentioned above. If appropriate, the reaction can also advantageously be carried out in the presence of an excess of the compound (XII) without addition of a further solvent. The reaction is preferably carried out in the solvent acetone or N-methylpyrrolidinone.

The process step (XI)+(XII)→(VI-B) is generally carried out in a temperature range of from 0° C. to +180° C., preferably in the range from +20° C. to +100° C., in particular at from +60° C. to +100° C., if appropriate in a microwave. The reaction can be carried out at atmospheric, elevated or reduced pressure (for example in the range from 0.5 to 5 bar). The reaction is generally carried out at atmospheric pressure.

The compounds of the formula (XII) are commercially available, known from the literature, or they can be prepared analogously to processes known from the literature. The compound of the formula (X) can be obtained in a simple manner by reacting [bis-(methylthio)methylene]malononitrile with cyanothioacetamide in the presence of a base such as triethylamine.

Compounds of the formula (VI) in which X represents O can be prepared by reacting a compound of the formula (XIII)

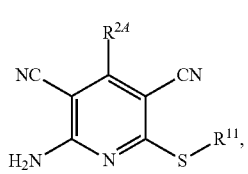
(XIII)

in which $R^{24}$ has the meaning given above,
and
$R^{11}$ represents $(C_1-C_4)$-alkyl or phenyl,
in an inert solvent in the presence of a base with a compound of the formula (XIV)

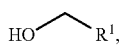
(XIV)

in which $R^1$ has the meaning given above, and to give compounds of the formula (VI-C)

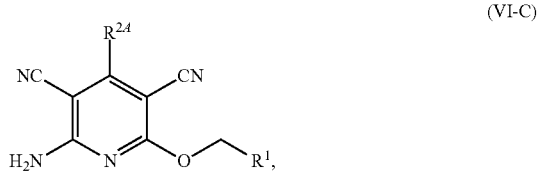
(VI-C)

in which $R^1$ and $R^{24}$ each have the meanings given above.

The compounds of the formula (XIII) can be prepared analogously to processes described in the literature [cf., for example, Kambe et al., *Synthesis*, 531-533 (1981); Elnagdi et al., *Z. Naturforsch.* 47b, 572-578 (1991); Reddy et al., *J. Med. Chem.* 49, 607-615 (2006); Evdokimov et al., *Org. Lett.* 8, 899-902 (2006)] or by reacting compounds of the formula (VII-A) analogy to processes described in the literature [cf., for example, Fujiwara, H. et al., *Heterocycles* 1993, 36 (5), 1105-1113, Su et al., *J. Med. Chem.* 1988, 31, 1209-1215].

Further compounds of the formula (VI) in which X represents O can be prepared by converting the compound of the formula (XV)

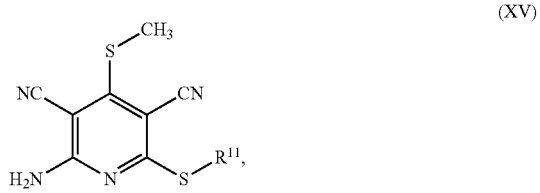
(XV)

in which $R^{11}$ has the meaning given above,
in an inert solvent in the presence of a base with a compound of the formula (XIV) into a compound of the formula (XVI)

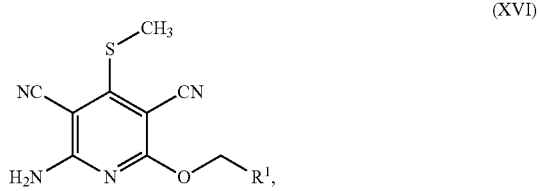
(XVI)

in which $R^1$ has the meaning given above,
and then reacting this compound in an inert solvent or in the absence of a solvent with a compound of the formula (XII) to give compounds of the formula (VI-D)

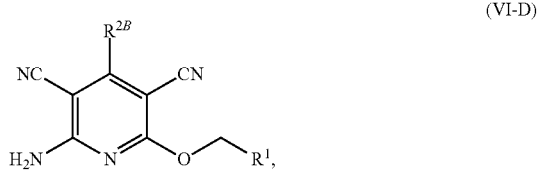
(VI-D)

in which $R^1$ and $R^{2B}$ each have the meanings given above, or
alternatively initially reacting a compound of the formula (XV) in an inert solvent or in the absence of a solvent with a compound of the formula (XII) to give compounds of the formula (XVII)

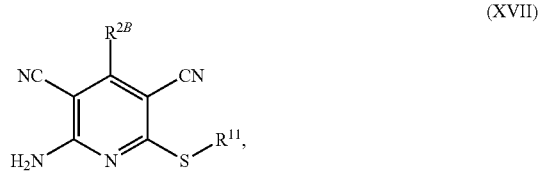

(XVII)

in which $R^{2B}$ and $R^{11}$ each have the meanings given above,
and then converting these with a compound of the formula (XIV) into compounds of the formula (VI-D).

The compounds of the formula (XV) in which $R^{11}$ represents phenyl can be prepared from the compound of the formula (X) analogously to the process described in Fujiwara, H. et al., *Heterocycles* 1993, 36 (5), 1105-1113.

The compounds of the formula (XV) in which $R^{11}$ represents ($C_1$-$C_4$)-alkyl can be prepared from the compound of the formula (X) analogously to the process described in Su et al., *J. Med. Chem.* 1988, 31, 1209-1215.

Suitable inert solvents for the reactions (XIII)+(XIV), (XV)+(XIV) and (XVII)+(XIV) are in particular acyclic and cyclic ethers, such as diethyl ether, methyl tert-butyl ether, 1,2-dimethoxyethane, tetrahydrofuran and dioxane, hydrocarbons, such as benzene, toluene, xylene, hexane and cyclohexane, or other solvents, such as dimethylformamide (DMF), dimethyl sulfoxide (DMSO), N-methylpyrrolidinone (NMP) and pyridine. It is also possible to use mixtures of these solvents. Preference is given to using 1,2-dimethoxyethane.

Suitable bases for these reactions are in particular alkali metal alkoxides, such as sodium methoxide or potassium methoxide, sodium ethoxide or potassium ethoxide or sodium tert-butoxide or potassium tert-butoxide, alkali metal hydrides, such as lithium hydride, sodium hydride or potassium hydride, amides, such as sodium amide, lithium bis(trimethylsilyl)amide, sodium bis(trimethylsilyl)amide or potassium bis(trimethylsilyl)-amide or lithium diisopropylamide, or organometallic compounds, such as butyllithium or phenyllithium. Preference is given to using potassium tert-butoxide.

Here, the base is generally employed in an amount of from 1 to 1.25 mol, preferably in an equimolar amount, based on 1 mol of the compound of the formula (XIV).

The reactions (XIII)+(XIV), (XV)+(XIV) and (XVII)+(XIV) are generally carried out in a temperature range of from −20° C. to +120° C., preferably at from +20° C. to +100° C., if appropriate in a microwave. The reactions can be carried out at atmospheric, elevated or reduced pressure (for example in the range from 0.5 to 5 bar). The reactions are generally carried out at atmospheric pressure.

Suitable solvents for the process steps (XV) or (XVI)+(XII)→(VI-D) are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane or chlorobenzene, or other solvents, such as dimethylformamide (DMF), dimethyl sulfoxide (DMSO), N-methylpyrrolidinone (NMP), acetonitrile or pyridine. Another suitable solvent is water. It is also possible to use mixtures of the solvents mentioned above. If appropriate, the reaction can also advantageously be carried out in the presence of an excess of the compound (XII) without addition of a further solvent. The reaction is preferably carried out in the solvent acetone or N-methylpyrrolidinone.

The process steps (XV) or (XVI)+(XII)→(VI-D) are generally carried out in a temperature range of from 0° C. to +180° C., preferably in the range from +20° C. to +100° C., in particular at from +60° C. to +100° C., if appropriate in a microwave. The reaction can be carried out at atmospheric, elevated or reduced pressure (for example in the range from 0.5 to 5 bar). The reaction is generally carried out at atmospheric pressure.

The preparation processes described above can be illustrated in an exemplary manner by the Reaction Schemes below:

Scheme 6

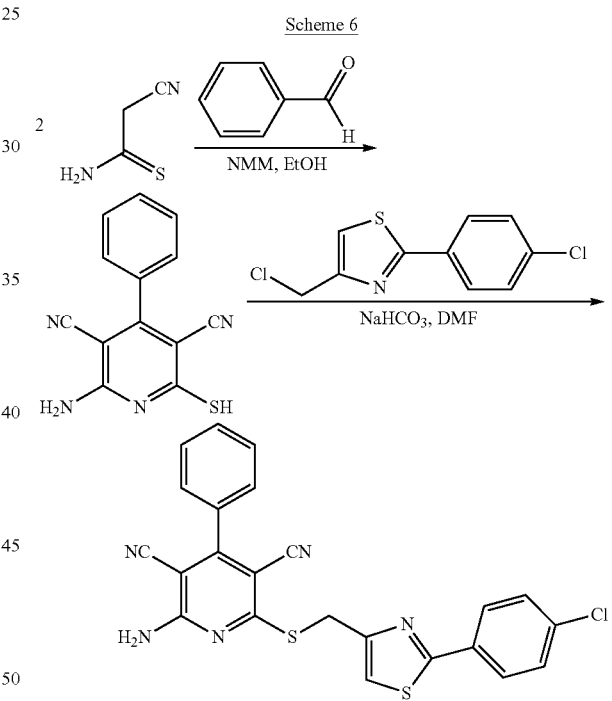

Scheme 7

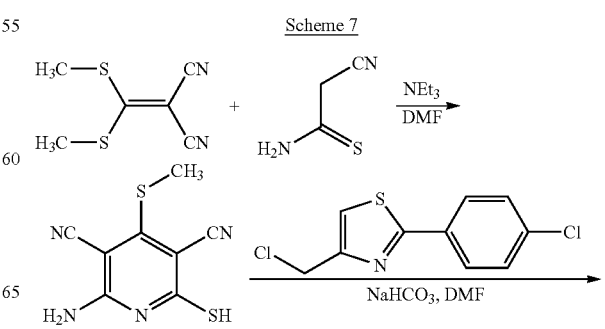

25
-continued
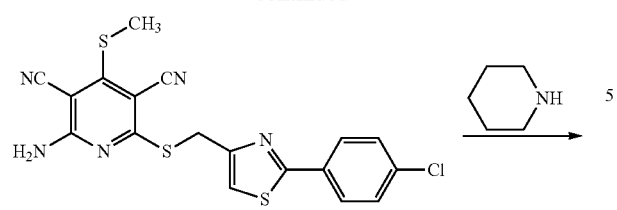
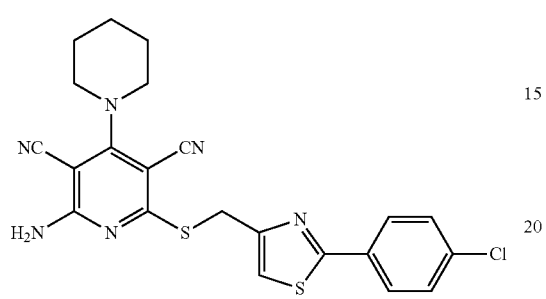
Scheme 8
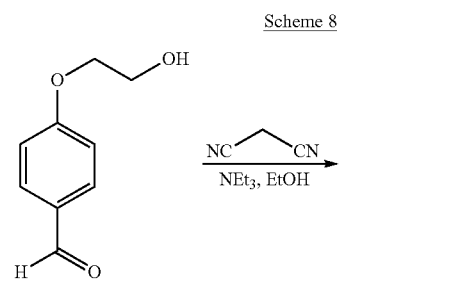
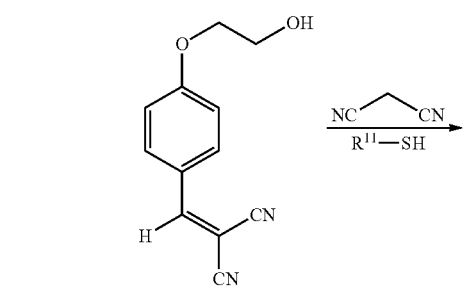
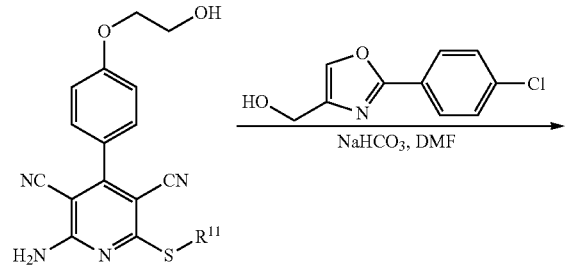
26
-continued
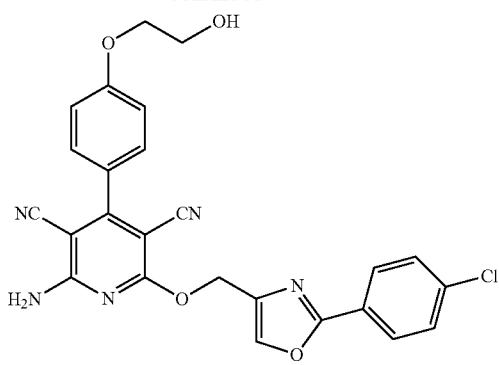
Scheme 9
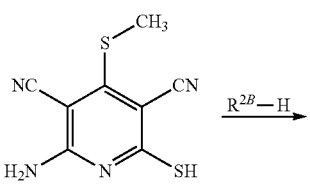
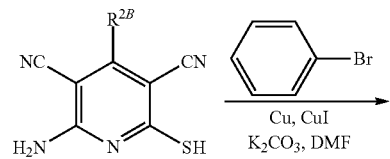
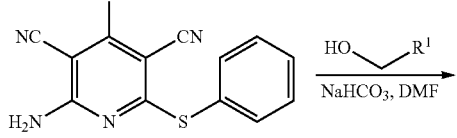
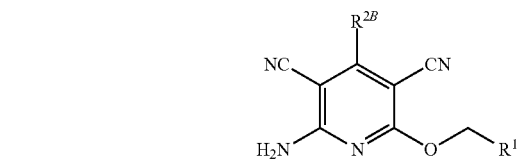
Scheme 10
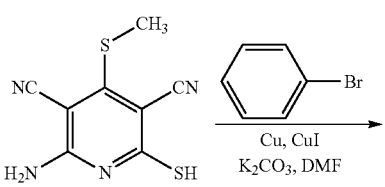
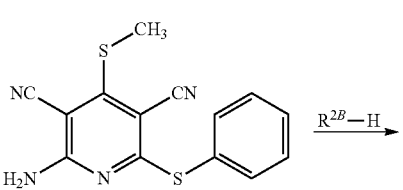

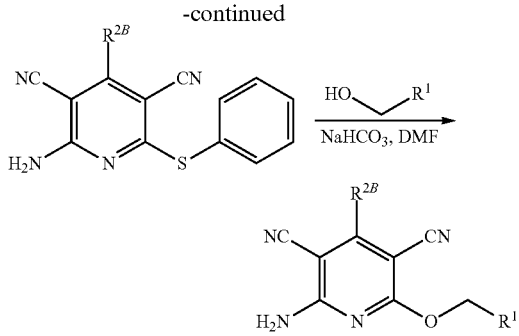

Surprisingly, the compounds according to the invention have an unforeseeable useful pharmacological activity spectrum and are therefore suitable in particular for the prevention and/or treatment of disorders.

The pharmaceutical activity of the compounds according to the invention can be explained by their action as potent, selective ligands at individual subtypes or a plurality of subtypes of adenosine receptors, in particular as selective ligands at adenosine A1 and/or A2b receptors. Here, they act as selective A1 agonists, as selective A1 antagonists or as selective dual A1/A2b agonists.

The compounds according to the invention act mainly as selective adenosine A1 agonists.

In the context of the present invention, "selective ligands at adenosine A1 and/or A2b receptors" are adenosine receptor ligands where firstly a marked activity at A1 and/or A2b adenosine receptor subtypes and secondly no or a considerably weaker activity (by a factor of 10 or more) at A2a and A3 adenosine receptor subtypes can be observed, where with respect to the test methods for activity/selectivity, reference is made to the tests described in section B-1.

Depending on their particular structure, the compounds according to the invention can act as full adenosine receptor agonists, as partial adenosine receptor agonists or as adenosine receptor antagonists. Partial adenosine receptor agonists are defined here as receptor ligands which trigger a functional response at adenosine receptors which is less than that of full agonists (such as, for example, adenosine itself). Accordingly, partial agonists have lower activity with respect to receptor activation than full agonists. The compounds of the formula (I) are suitable alone or in combination with one or more other active ingredients for the prevention and/or treatment of various disorders, for example in particular hypertension and other disorders of the cardiovascular system (cardiovascular disorders), for cardioprotection following lesions of the heart, and of metabolic disorders and kidney disorders.

In the context of the present invention, disorders of the cardiovascular system or cardiovascular disorders are to be understood as including, in addition to hypertension, for example in particular the following disorders: peripheral and cardial vascular disorders, coronary heart disease, coronary restenosis, such as, for example, restenosis after balloon dilation of peripheral blood vessels, myocardial infarction, acute coronary syndrome, stable and unstable angina pectoris, heart failure, tachycardias, arrhythmias, atrial and ventricular fibrillation, impaired peripheral circulation, elevated levels of fibrinogen and of low density LDL, and elevated concentrations of plasminogen activator inhibitor 1 (PAI-1), especially coronary heart disease, acute coronary syndrome, angina pectoris, heart failure, myocardial infarction, atrial fibrillation and hypertension.

In the context of the present invention, the term heart failure includes both acute and chronic manifestations of heart failure, as well as more specific or related types of disease, such as acute decompensated heart failure, right heart failure, left heart failure, global failure, ischemic cardiomyopathy, dilated cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

The compounds according to the invention are furthermore also suitable for reducing the myocard region affected by an infarct, and also for the prevention of secondary infarcts. The compounds according to the invention are furthermore suitable for the prevention and/or treatment of thromboembolic disorders, reperfusion damage following ischemia, micro- and macrovascular lesions (vasculitis), edemas, ischemias such as myocardial infarction, stroke and transient ischemic attacks, and for organ protection in connection with transplants, bypass operations, catheter heart examinations and other surgical procedures.

Furthermore, the compounds according to the invention are suitable for the treatment and/or prevention of kidney diseases, in particular of renal insufficiency. In the context of the present invention, the term renal insufficiency comprises both acute and chronic manifestations of renal insufficiency, as well as underlying or related kidney diseases such as renal hypoperfusion, obstructive uropathy, glomerulonephritis, acute glomerulonephritis, tubulointerstitial diseases, nephropathic diseases such as primary and congenital kidney disease, nephritis, nephropathy induced by toxic substances, diabetic nephropathy, pyelonephritis, renal cysts and nephrosclerosis, which can be characterized diagnostically for example by abnormally reduced creatinine and/or water excretion, abnormally raised blood concentrations of urea, nitrogen, potassium and/or creatinine, altered activity of renal enzymes, such as, for example, glutamylsynthetase, altered urine osmolarity or urine volume, increased microalbuminuria, macroalbuminuria, lesions on glomeruli and arterioles, tubular dilatation, hyperphosphatemia and/or need for dialysis. The present invention also comprises the use of the compounds according to the invention for the treatment and/or prevention of sequelae of renal insufficiency, for example hypertension, pulmonary edema, heart failure, uraemia, anemia, electrolyte disturbances (for example hyperkalemia, hyponatremia) and disturbances in bone and carbohydrate metabolism.

Further indications for which the compounds according to the invention may be used are, for example, the prevention and/or treatment of disorders of the urogenital system, such as, for example, irritable bladder, erectile dysfunction and female sexual dysfunction, but in addition also the prevention and/or treatment of inflammatory disorders, such as, for example, inflammatory dermatoses (psoriasis, acne, eczema, neurodermitis, dermatitis, keratitis, formation of scars, formation of warts, frostbites), of disorders of the central nervous system and neurodegenerative disorders (stroke, Alzheimer's disease, Parkinson's disease, dementia, epilepsy, depression, multiple sclerosis), of states of pain, cancerous diseases (skin cancer, liposarcomas, carcinomas of the gastrointestinal tract, the liver, pancreas, lung, kidney, ureter, prostate and the genital tract), and also of nausea and emesis associated with cancer therapies. Other areas of indication are, for example, the prevention and/or treatment of inflammatory and immune disorders (Crohn's disease, ulcerative colitis, lupus erythematodes, rheumatoid arthritis) and respiratory disorders, such as, for example, chronic obstructive pulmonary disease (chronic bronchitis, COPD), asthma, pulmonary emphysema, bronchiectases, cystic fibrosis (mucoviscidosis) and pulmonary hypertension, in particular pulmonary arterial hypertension.

Finally, the compounds according to the invention are also suitable for the prevention and/or treatment of diabetes, in particular diabetes mellitus, gestation diabetes, insulin-dependent diabetes and non-insulin-dependent diabetes, of diabetic sequelae such as, for example, retinopathy, nephropathy and neuropathy, of metabolic disorders (metabolic syndrome, hyperglycemia, hyperinsulinemia, insulin resistance, glucose intolerance, obesity (adipositas)) and also of arteriosclerosis and dyslipidemias (hypercholesterolemia, hypertriglyceridemia, elevated concentrations of postprandial plasma triglycerides, hypoalphalipoproteinemia, combined hyperlipidemias), in particular of diabetes, metabolic syndrome and dyslipidemias.

In addition, the compounds according to the invention can also be used for the treatment and/or prevention of disorders of the thyroid gland (hyperthyreosis), disorders of the pancreas (pancreatitis), fibrosis of the liver, viral diseases (HPV, HCMV, HIV), cachexia, osteoporosis, gout, incontinence, and also for wound healing and angiogenesis.

The present invention furthermore provides the use of the compounds according to the invention for the treatment and/or prevention of disorders, in particular the disorders mentioned above.

The present invention furthermore provides the use of the compounds according to the invention for preparing a medicament for the treatment and/or prevention of disorders, in particular the disorders mentioned above.

The present invention furthermore provides a method for the treatment and/or prevention of disorders, in particular the disorders mentioned above, using an effective amount of at least one of the compounds according to the invention.

The present invention furthermore provides the compounds according to the invention for use in a method for the treatment and/or prophylaxis of coronary heart disease, acute coronary syndrome, angina pectoris, heart failure, myocardial infarction and atrial fibrillation.

The present invention furthermore provides the compounds according to the invention for methods for the treatment and/or prophylaxis of diabetes, metabolic syndrome and dyslipidemias.

The compounds according to the invention can be used alone or, if required, in combination with other active compounds. The present invention furthermore provides medicaments comprising at least one of the compounds according to the invention and one or more further active ingredients, in particular for the treatment and/or prevention of the disorders mentioned above.

Suitable active ingredients for combination are, by way of example and by way of preference: active ingredients which modulate lipid metabolism, antidiabetics, hypotensive agents, perfusion-enhancing and/or antithrombotic agents, antioxidants, chemokine receptor antagonists, p38-kinase inhibitors, NPY agonists, orexin agonists, anorectics, PAF-AH inhibitors, antiphlogistics (COX inhibitors, $LTB_4$-receptor antagonists), analgesics for example aspirin, antidepressants and other psychopharmaceuticals.

The present invention relates in particular to combinations of at least one of the compounds according to the invention with at least one lipid metabolism-altering active ingredient, antidiabetic, blood pressure-reducing active ingredient and/or agent having antithrombotic effects.

The compounds according to the invention can preferably be combined with one or more lipid metabolism-modulating active ingredients, by way of example and by way of preference from the group of the HMG-CoA reductase inhibitors, inhibitors of HMG-CoA reductase expression, squalene synthesis inhibitors, ACAT inhibitors, LDL receptor inductors, cholesterol absorption inhibitors, polymeric bile acid adsorbers, bile acid reabsorption inhibitors, MTP inhibitors, lipase inhibitors, LpL activators, fibrates, niacin, CETP inhibitors, PPAR-α, PPAR-γ and/or PPAR-δ agonists, RXR modulators, FXR modulators, LXR modulators, thyroid hormones and/or thyroid mimetics, ATP citrate lyase inhibitors, Lp(a) antagonists, cannabinoid receptor 1 antagonists, leptin receptor agonists, bombesin receptor agonists, histamine receptor agonists and the antioxidants/radical scavengers;

antidiabetics mentioned in the Rote Liste 2004/II, chapter 12, and also, by way of example and by way of preference, those from the group of the sulfonylureas, biguanides, meglitinide derivatives, glucosidase inhibitors, inhibitors of dipeptidyl-peptidase IV (DPP-IV inhibitors), oxadiazolidinones, thiazolidinediones, GLP 1 receptor agonists, glucagon antagonists, insulin sensitizers, CCK 1 receptor agonists, leptin receptor agonists, inhibitors of liver enzymes involved in the stimulation of gluconeogenesis and/or glycogenolysis, modulators of glucose uptake and also potassium channel openers, such as, for example, those disclosed in WO 97/26265 and WO 99/03861;

hypotensive active ingredients, by way of example and by way of preference from the group of the calcium antagonists, angiotensin AII antagonists, ACE inhibitors, renin inhibitors, beta-receptor blockers, alpha-receptor blockers, aldosterone antagonists, mineralocorticoid receptor antagonists, ECE inhibitors, ACE/NEP inhibitors and the vasopeptidase inhibitors; and/or antithrombotic agents, by way of example and by way of preference from the group of the platelet aggregation inhibitors or the anticoagulants;

diuretics;

vasopressin receptor antagonists;

organic nitrates and NO donors;

compounds with positive inotropic activity;

compounds which inhibit the degradation of cyclic guanosine monophosphate (cGMP) and/or cyclic adenosine monophosphat (cAMP), such as, for example, inhibitors of phosphodiesterases (PDE) 1, 2, 3, 4 and/or 5, in particular PDE 5 inhibitors, such as sildenafil, vardenafil and tadalafil, and also PDE 3 inhibitors, such as milrinone; natriuretic peptides, such as, for example, "atrial natriuretic peptide" (ANP, anaritide), "B-type natriuretic peptide" or "brain natriuretic peptide" (BNP, nesiritide), "C-type natriuretic peptide" (CNP) and also urodilatin;

agonists of the prostacyclin receptor (IP receptor), such as, by way of example, iloprost, beraprost, cicaprost;

inhibitors of the $I_f$ (funny channel) channel, such as, by way of example, ivabradine; calcium sensitizers, such as, by way of example and by way of preference, levosimendan;

potassium supplements;

NO-independent, but heme-dependent stimulators of guanylate cyclase, such as, in particular, the compounds described in WO 00/06568, WO 00/06569, WO 02/42301 and WO 03/095451;

NO- and heme-independent activators of guanylate cyclase, such as, in particular, the compounds described in WO 01/19355, WO 01/19776, WO 01/19778, WO 01/19780, WO 02/070462 and WO 02/070510;

inhibitors of human neutrophil elastase (HNE), such as, for example, sivelestat and DX-890 (Reltran);

compounds which inhibit the signal transduction cascade, such as, for example, tyrosine-kinase inhibitors, in particular sorafenib, imatinib, gefitinib and erlotinib; and/or compounds which modulate the energy metabolism of the heart, such as, for example, etomoxir, dichloroacetate, ranolazine and trimetazidine.

Lipid metabolism-modifying active ingredients are to be understood as meaning, preferably, compounds from the group of the HMG-CoA reductase inhibitors, squalene synthesis inhibitors, ACAT inhibitors, cholesterol absorption inhibitors, MTP inhibitors, lipase inhibitors, thyroid hormones and/or thyroid mimetics, niacin receptor agonists, CETP inhibitors, PPAR-α agonists, PPAR-γ agonists, PPAR-δ agonists, polymeric bile acid adsorbers, bile acid reabsorption inhibitors, antioxidants/radical scavengers and also the cannabinoid receptor 1 antagonists.

In a preferred embodiment of the invention, the compounds according to the invention are administered in combination with an HMG-CoA reductase inhibitor from the class of the statins, such as, by way of example and by way of preference, lovastatin, simvastatin, pravastatin, fluvastatin, atorvastatin, rosuvastatin, cerivastation or pitavastatin.

In a preferred embodiment of the invention, the compounds according to the invention are administered in combination with a squalene synthesis inhibitor, such as, by way of example and by way of preference, BMS-188494 or TAK-475.

In a preferred embodiment of the invention, the compounds according to the invention are administered in combination with an ACAT inhibitor, such as, by way of example and by way of preference, avasimibe, melinamide, pactimibe, eflucimibe or SMP-797.

In a preferred embodiment of the invention, the compounds according to the invention are administered in combination with a cholesterol absorption inhibitor, such as, by way of example and by way of preference, ezetimibe, tiqueside or pamaqueside.

In a preferred embodiment of the invention, the compounds according to the invention are administered in combination with an MTP inhibitor, such as, by way of example and by way of preference, implitapide, BMS-201038, R-103757 or JTT-130.

In a preferred embodiment of the invention, the compounds according to the invention are administered in combination with a lipase inhibitor, such as, by way of example and by way of preference, orlistat.

In a preferred embodiment of the invention, the compounds according to the invention are administered in combination with a thyroid hormone and/or thyroid mimetic, such as, by way of example and by way of preference, D-thyroxine or 3,5,3'-triiodothyronine (T3). In a preferred embodiment of the invention, the compounds according to the invention are administered in combination with an agonist of the niacin receptor, such as, by way of example and by way of preference, niacin, acipimox, acifran or radecol.

In a preferred embodiment of the invention, the compounds according to the invention are administered in combination with a CETP inhibitor, such as, by way of example and by way of preference, torcetrapib, JTT-705, BAY 60-5521, BAY 78-7499 or CETP vaccine (Avant).

In a preferred embodiment of the invention, the compounds according to the invention are administered in combination with a PPAR-γ agonist, such as, by way of example and by way of preference, pioglitazone or rosiglitazone.

In a preferred embodiment of the invention, the compounds according to the invention are administered in combination with a PPAR-δ agonist, such as, by way of example and by way of preference, GW-501516 or BAY 68-5042.

In a preferred embodiment of the invention, the compounds according to the invention are administered in combination with a polymeric bile acid adsorber, such as, by way of example and by way of preference, cholestyramine, colestipol, colesolvam, CholestaGel or colestimide.

In a preferred embodiment of the invention, the compounds according to the invention are administered in combination with a bile acid reabsorption inhibitor, such as, by way of example and by way of preference, ASBT (=IBAT) inhibitors, such as, for example, AZD-7806, S-8921, AK-105, BARI-1741, SC-435 or SC-635.

In a preferred embodiment of the invention, the compounds according to the invention are administered in combination with an antioxidant/radical scavenger, such as, by way of example and by way of preference, probucol, AGI-1067, BO-653 or AEOL-10150.

In a preferred embodiment of the invention, the compounds according to the invention are administered in combination with a cannabinoid receptor 1 antagonist, such as, by way of example and by way of preference, rimonabant or SR-147778.

Antidiabetics are to be understood as meaning, preferably, insulin and insulin derivatives, and also orally effective hypoglycemic active ingredients. Here, insulin and insulin derivatives include both insulins of animal, human or biotechnological origin and also mixtures thereof. The orally effective hypoglycemic active ingredients preferably include sulfonylureas, biguanides, meglitinide derivatives, glucosidase inhibitors and PPAR-gamma agonists.

In a preferred embodiment of the invention, the compounds according to the invention are administered in combination with insulin.

In a preferred embodiment of the invention, the compounds according to the invention are administered in combination with a sulfonylurea, such as, by way of example and by way of preference, tolbutamide, glibenclamide, glimepiride, glipizide or gliclazide.

In a preferred embodiment of the invention, the compounds according to the invention are administered in combination with a biguanide, such as, by way of example and by way of preference, metformin.

In a preferred embodiment of the invention, the compounds according to the invention are administered in combination with a meglitinide derivative, such as, by way of example and by way of preference, repaglinide or nateglinide.

In a preferred embodiment of the invention, the compounds according to the invention are administered in combination with a glucosidase inhibitor, such as, by way of example and by way of preference, miglitol or acarbose.

In a preferred embodiment of the invention, the compounds according to the invention are administered in combination with a DPP-IV inhibitor, such as, by way of example and by way of preference, sitagliptin and vildagliptin.

In a preferred embodiment of the invention, the compounds according to the invention are administered in combination with a PPAR-gamma agonist, for example from the class of the thiazolidinediones, such as, by way of example and by way of preference, pioglitazone or rosiglitazone.

The hypotensive agents are preferably understood as meaning compounds from the group of the calcium antagonists, angiotensin AII antagonists, ACE inhibitors, beta-receptor blockers, alpha-receptor blockers and diuretics.

In a preferred embodiment of the invention, the compounds according to the invention are administered in combination with a calcium antagonist, such as, by way of example and by way of preference, nifedipine, amlodipine, verapamil or diltiazem.

In a preferred embodiment of the invention, the compounds according to the invention are administered in combination with an angiotensin AII antagonist, such as, by way of example and by way of preference, losartan, valsartan, candesartan, embusartan, olmesartan or telmisartan.

In a preferred embodiment of the invention, the compounds according to the invention are administered in combination with an ACE inhibitor, such as, by way of example and by way of preference, enalapril, captopril, lisinopril, ramipril, delapril, fosinopril, quinopril, perindopril or trandopril.

In a preferred embodiment of the invention, the compounds according to the invention are administered in combination with a beta-receptor blocker, such as, by way of example and by way of preference, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an alpha-receptor blocker, such as, by way of example and by way of preference, prazosin.

In a preferred embodiment of the invention, the compounds according to the invention are administered in combination with a diuretic, such as, by way of example and by way of preference, furosemide, bumetanide, torsemide, bendroflumethiazide, chlorothiazide, hydrochlorothiazide, hydroflumethiazide, methyclothiazide, polythiazide, trichloromethiazide, chlorothalidone, indapamide, metolazone, quinethazone, acetazolamide, dichlorophenamide, methazolamide, glycerol, isosorbide, mannitol, amiloride or triamteren.

In a preferred embodiment of the invention, the compounds according to the invention are administered in combination with an aldosterone or mineralocorticoid receptor antagonist, such as, by way of example and by way of preference, spironolactone or eplerenone.

In a preferred embodiment of the invention, the compounds according to the invention are administered in combination with a vasopressin receptor antagonist, such as, by way of example and by way of preference, conivaptan, tolvaptan, lixivaptan or SR-121463.

In a preferred embodiment of the invention, the compounds according to the invention are administered in combination with an organic nitrate or NO donor, such as, by way of example and by way of preference, sodium nitroprusside, nitroglycerol, isosorbide mononitrate, isosorbide dinitrate, molsidomin or SIN-1, or in combination with inhalative NO.

In a preferred embodiment of the invention, the compounds according to the invention are administered in combination with a positive-inotropic compound, such as, by way of example and by way of preference, cardiac glycosides (digoxin), beta-adrenergic and dopaminergic agonists, such as isoproterenol, adrenaline, noradrenaline, dopamine or dobutamine.

In a preferred embodiment of the invention, the compounds according to the invention are administered in combination with antisympathotonics, such as reserpine, clonidine or alpha-methyldopa, or in combination with potassium channel agonists, such as minoxidil, diazoxide, dihydralazine or hydralazine, or with substances which release nitrogen oxide, such as glycerol nitrate or sodium nitroprusside.

Antithrombotics are to be understood as meaning, preferably, compounds from the group of the platelet aggregation inhibitors or the anticoagulants.

In a preferred embodiment of the invention, the compounds according to the invention are administered in combination with a platelet aggregation inhibitor, such as, by way of example and by way of preference, aspirin, clopidogrel, ticlopidine or dipyridamol.

In a preferred embodiment of the invention, the compounds according to the invention are administered in combination with a thrombin inhibitor, such as, by way of example and by way of preference, ximelagatran, melagatran, dabigatran, bivalirudin or clexane. In a preferred embodiment of the invention, the compounds according to the invention are administered in combination with a GPIIb/IIIa antagonist, such as, by way of example and by way of preference, tirofiban or abciximab.

In a preferred embodiment of the invention, the compounds according to the invention are administered in combination with a factor Xa inhibitor, such as, by way of example and by way of preference, rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as, by way of example and by way of preference, coumarin.

In the context of the present invention, particular preference is given to combinations comprising at least one of the compounds according to the invention and also one or more further active ingredients selected from the group consisting of HMG-CoA reductase inhibitors (statins), diuretics, beta-receptor blockers, organic nitrates and NO donors, ACE inhibitors, angiotensin AII antagonists, aldosterone and mineralocorticoid receptor antagonists, vasopressin receptor antagonists, platelet aggregation inhibitors and anticoagulants, and also their use for the treatment and/or prevention of the disorders mentioned above.

The present invention furthermore provides medicaments comprising at least one compound according to the invention, usually together with one or more inert, nontoxic, pharmaceutically suitable auxiliaries, and also their use for the purposes mentioned above.

The compounds according to the invention can act systemically and/or locally. For this purpose, they can be administered in a suitable manner, such as, for example, orally, parenterally, pulmonally, nasally, sublingually, lingually, buccally, rectally, dermally, transdermally, conjunctivally, otically or as an implant or stent.

For these administration routes, the compounds according to the invention can be administered in suitable administration forms.

Suitable for oral administration are administration forms which work in accordance with the prior art and release the compounds according to the invention rapidly and/or in modified form and which comprise the compounds according to the invention in crystalline and/or amorphicized and/or dissolved form, such as, for example, tablets (uncoated or coated tablets, for example with enteric coats or coats which dissolve in a delayed manner or are insoluble and which control the release of the compound according to the invention), films/wafers or tablets which dissolve rapidly in the oral cavity, films/lyophilizates, capsules (for example hard or soft gelatin capsules), sugar-coated tablets, granules, pellets, powders, emulsions, suspensions, aerosols or solutions.

Parenteral administration may take place by circumventing a bioabsorption step (for example intravenously, intraarterially, intracardially, intraspinally or intralumbarly), or with bioabsorption (for example intramuscularly, subcutaneously, intracutaneously, percutaneously or intraperitoneally). Administration forms suitable for parenteral administration are inter alia preparations for injection or infusion in the form of solutions, suspensions, emulsions, lyophilizates or sterile powders.

Suitable for other administration routes are, for example, medicaments suitable for inhalation (inter alia powder inhalers, nebulizers), nose drops, solutions or sprays, tablets to be administered lingually, sublingually or buccally, films/wafers or capsules, suppositories, preparations to be administered to ears or eyes, vaginal capsules, aqueous suspensions (lotions, shaking mixtures), lipophilic suspensions, ointments, creams, transdermal therapeutic systems (for example plasters), milk, pastes, foams, powders for pouring, implants or stents.

Preference is given to oral or parenteral administration, in particular to oral and intravenous administration.

The compounds according to the invention can be converted into the administration forms mentioned. This can be carried out in a manner known per se by mixing with inert, non-toxic, pharmaceutically suitable auxiliaries. These auxiliaries include inter alia carriers (for example microcrystalline cellulose, lactose, mannitol), solvents (for example liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides), and flavor and/or odor corrigents.

In general, it has been found to be advantageous in the case of parenteral administration to administer amounts of about 0.001 to 1 mg/kg, preferably about 0.01 to 0.5 mg/kg of body weight to obtain effective results. In the case of oral administration, the dosage is from about 0.01 to 100 mg/kg, preferably from about 0.01 to 20 mg/kg and very particularly preferably from 0.1 to 10 mg/kg of body weight.

In spite of this, it may be necessary to deviate from the amounts mentioned, namely depending on body weight, administration route, individual response to the active ingredient, the type of preparation and the time or the interval at which administration takes place. Thus, in some cases it may be sufficient to administer less than the abovementioned minimum amount, whereas in other cases the upper limit mentioned has to be exceeded. In the case of the administration of relatively large amounts, it may be expedient to divide these into a plurality of individual doses which are administered over the course of the day.

The working examples below illustrate the invention. The invention is not limited to the examples.

The percentages in the tests and examples below are, unless indicated otherwise, percentages by weight; parts are parts by weight. Solvent ratios, dilution ratios and concentrations of liquid/liquid solutions are in each case based on volume.

A. EXAMPLES

Abbreviations used:

| | |
|---|---|
| aq. | aqueous |
| br s | broad singulet (in NMR) |
| Ex. | Example |
| c | concentration |
| d | doublet (in NMR) |
| dd | doublet of doublets (in NMR) |
| TLC | thin-layer chromatography |
| DCI | direct chemical ionization (in MS) |
| DMF | N,N-dimethylformamide |
| DMSO | dimethyl sulfoxide |
| ee | enantiomeric excess |
| EI | electron impact ionization (in MS) |
| ent | enantiomer/enantiomerically pure |
| ESI | electrospray ionization (in MS) |
| Et | ethyl |
| m.p. | melting point |
| GC-MS | gas chromatography-coupled mass spectrometry |
| h | hour(s) |
| HATU | O-(7-azabenzotriazol-1-yl)-N,N,N',N'-tetramethyluronium hexafluorophosphate |
| HPLC | high-pressure, high-performance liquid chromatography |
| cat. | catalytic |
| conc. | concentrated |
| LC-MS | liquid chromatography-coupled mass spectrometry |
| lit. | literature (reference) |
| MeCN | acetonitrile |
| min | minute(s) |
| MS | mass spectrometry |
| NMP | N-methylpyrrolidone |
| NMR | nuclear magnetic resonance spectrometry |
| q | quartet (in NMR) |
| rac. | racemic |
| RP-HPLC | reversed-phase HPLC |
| RT | room temperature |
| $R_t$ | retention time (in HPLC) |
| s | singlet (in NMR) |
| t | triplet (in NMR) |
| t-Bu | tert-butyl |
| TFA | trifluoroacetic acid |
| THF | tetrahydrofuran |
| dil. | dilute |

HPLC, LC-MS and GC-MS methods:

Method 1 (HPLC): instrument: Hewlett Packard Series 1050; column: Symmetry TM C18 3.9×150 mm; flow rate: 1.5 ml/min; mobile phase A: water, mobile phase B: acetonitrile; gradient:→0.6 min 10% B→3.8 min 100% B→5.0 min 100% B→5.5 min 10% B; stop time: 6.0 min; injection volume: 10 µl; diode array detector signal: 214 and 254 nm.

Method 2 (LC-MS): MS instrument type: Micromass ZQ; HPLC instrument type: Waters Alliance 2795; column: Merck Chromolith SpeedROD RP-18e 100 mm×4.6 mm; mobile phase A: 1 l of water+0.5 ml of 50% strength formic acid, mobile phase B: 1 l of acetonitrile+0.5 ml of 50% strength formic acid; gradient: 0.0 min 10% B→7.0 min 95% B→9.0 min 95% B; oven: 35° C.; flow rate: 0.0 min 1.0 ml/min→7.0 min 2.0 ml/min→9.0 min 2.0 ml/min; UV detection: 210 nm.

Method 3 (LC-MS): MS instrument type: Micromass ZQ; HPLC instrument type: HP 1100 Series; UV DAD; column: Phenomenex Gemini 3μ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 4 (LC-MS): instrument: Micromass Quattro LCZ with HPLC Agilent series 1100; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 208-400 nm.

Method 5 (LC-MS): MS instrument type: Micromass ZQ; HPLC instrument type: Waters Alliance 2795; column: Phenomenex Synergi 2.5μ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 6 (LC-MS): instrument: Micromass QuattroPremier with Waters UPLC Acquity; column: Thermo Hypersil GOLD 1.9μ 50×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; oven: 50° C.; flow rate: 0.33 ml/min; UV detection: 210 nm.

Method 7 (LC-MS): MS instrument type: Waters ZQ; HPLC instrument type: Waters Alliance 2795; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 210 nm.

Method 8 (LC-MS): instrument: Micromass Quattro LCZ with HPLC Agilent series 1100; column: Phenomenex Synergi 2.5μ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.

Method 9 (LC-MS): instrument: Micromass Quattro LCZ with HPLC Agilent series 1100; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 10 (LC-MS): MS instrument type: Micromass ZQ; HPLC instrument type: Waters Alliance 2795; column: Merck Chromolith SpeedROD RP-18e 100×4.6 mm; mobile phase A: 1 l of water+0.5 ml of 50% strength formic acid; mobile phase B: 1 l of acetonitrile+0.5 ml of 50% strength formic acid; gradient: 0.0 min 10% B→7.0 min 95% B→9.0 min 95% B; oven: 35° C.; flow rate: 0.0 min 1.0 ml/min→7.0 min 2.0 ml/min→9.0 min 2.0 ml/min; UV detection: 210 nm.

Method 11 (LC-MS): instrument: Micromass Quattro LCZ with HPLC Agilent series 1100; column: Phenomenex Gemini 3μ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 12 (LC-MS): MS instrument type: M-40 DCI (NH₃); HPLC instrument type: HP 1100 with DAD detection; column: Kromasil 100 RP-18, 60 mm×2.1 mm, 3.5 μm; mobile phase A: 5 ml of $HClO_4$ (70% strength)/liter of water, mobile phase B: acetonitrile; gradient: 0 min 2% B→0.5 min 2% B→4.5 min 90% B→6.5 min 90% B→6.7 min 2% B→7.5 min 2% B; flow rate: 0.75 ml/min; column temperature: 30° C.; UV detection: 210 nm.

Starting Materials and Intermediates

Example 1A

2-Amino-4-[4-(2-hydroxyethoxy)phenyl]-6-sulfanylpyridine-3,5-dicarbonitrile

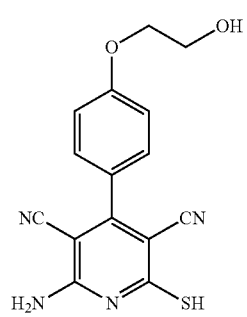 [SMILES: N#Cc1c(N)nc(S)c(C#N)c1-c1ccc(OCCO)cc1]

The preparation was carried out as described in WO 03/053441 for Example 6 (step 1).

LC-MS (Method 4): $R_t$=1.73 min; MS (ESIpos): m/z=313 [M+H]⁺.

Example 2A

2-Amino-4-phenyl-6-sulfanylpyridine-3,5-dicarbonitrile

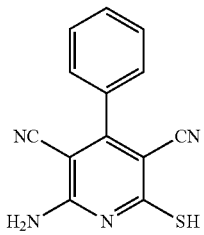 [SMILES: N#Cc1c(N)nc(S)c(C#N)c1-c1ccccc1]

The preparation is carried out analogously to Example 1A.
MS (ESIpos): m/z=253 (M+H)$^+$

Example 3A

2-Amino-4-(1H-pyrazol-3-yl)-6-sulfanylpyridine-3,5-dicarbonitrile

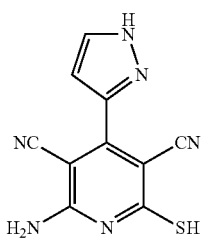 [SMILES: N#Cc1c(N)nc(S)c(C#N)c1-c1cc[nH]n1]

The preparation was carried out as described in WO 03/053441 for Example 6 (step 1) from pyrazole-3-carbaldehyde, cyanothioacetamide and 4-methylmorpholine.

LC-MS (Method 6): R$_t$=0.44 min; MS (ESIpos): m/z=243 [M+H]$^+$.

Example 4A

2'-Amino-6'-sulfanyl-3,4'-bipyridine-3',5'-dicarbonitrile

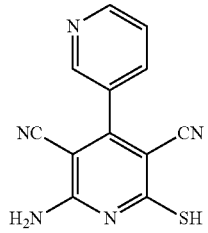 [SMILES: N#Cc1c(N)nc(S)c(C#N)c1-c1cccnc1]

The preparation was carried out analogously to Example 1A.

LC-MS (Method 3): R$_t$=1.26 min; MS (ESIpos): m/z=254 [M+H]+.

Example 5A

3-[({6-Amino-3,5-dicyano-4-[4-(2-hydroxyethoxy)phenyl]pyridin-2-yl}sulfanyl)methyl]benzoic acid

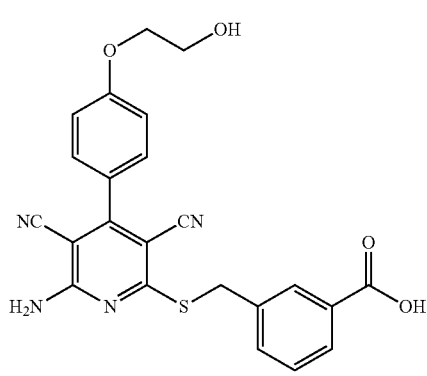 [SMILES: N#Cc1c(N)nc(SCc2cccc(C(=O)O)c2)c(C#N)c1-c1ccc(OCCO)cc1]

6.50 g (20.81 mmol) of the compound from Example 1A, 5.24 g (62.43 mmol) of sodium bicarbonate and 3.91 g (22.89 mmol) of 3-(chloromethyl)benzoic acid were combined in 100 ml of absolute DMF and stirred at room temperature for 1.5 h. The reaction mixture was poured into 700 ml of water, 1 N hydrochloric acid was added and the mixture was stirred for 1 h. The resulting precipitate was filtered off with suction through a glass frit and washed with water. The residue was dried under reduced pressure.

Yield: 8.56 g (92% of theory)

LC-MS (Method 7): $R_t$=2.84 min; MS (ESIpos): m/z=447 [M+H]$^+$.

The examples listed in Table 1 were prepared analogously to Example 5A from the corresponding starting materials with subsequent purification [preparative HPLC (Chromasil, water/acetonitrile+0.15% conc. hydrochloric acid)]:

TABLE 1

| Example No. | Structure (yield) | LC-MS: $R_t$ [min] (Method); MS (ESI): m/z [M + H]$^+$ |
|---|---|---|
| 6A | 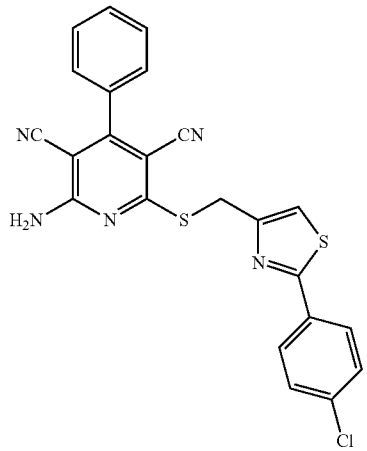 (93% of theory) | 4.26 min (Method 4); m/z = 460 |
| 7A | 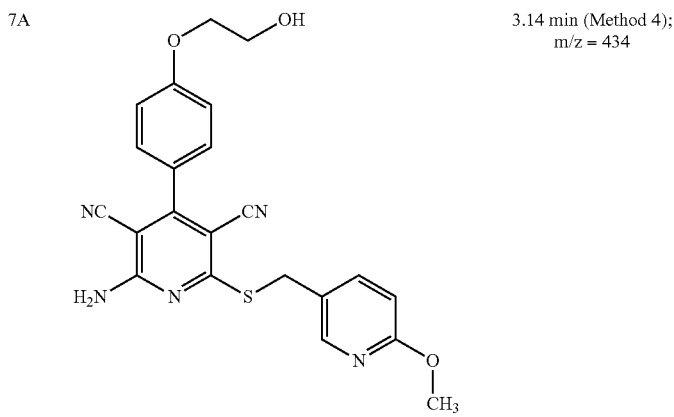 (98% of theory) | 3.14 min (Method 4); m/z = 434 |

TABLE 1-continued
| Example No. | Structure (yield) | LC-MS: $R_t$ [min] (Method); MS (ESI): m/z [M + H]$^+$ |
|---|---|---|
| 8A | 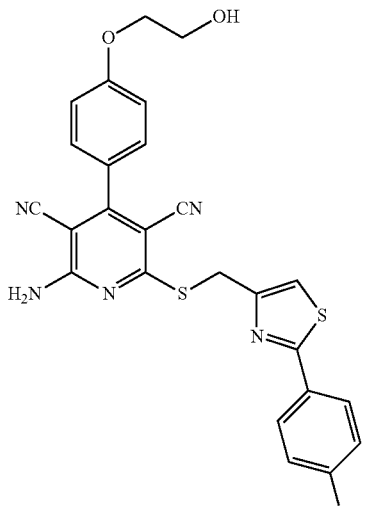 (80% of theory) | 5.69 min (Method 10); m/z = 520 |
| 9A | 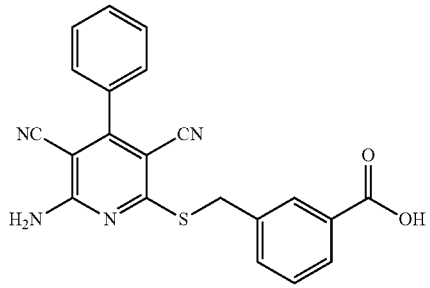 (79% of theory) | 3.42 min (Method 4); m/z = 387 |
| 10A | 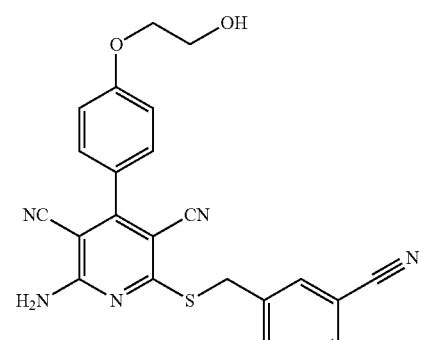 (92% of theory) | 3.29 min (Method 4); m/z = 428 |

TABLE 1-continued
| Example No. | Structure (yield) | LC-MS: R$_t$ [min] (Method); MS (ESI): m/z [M + H]$^+$ |
| --- | --- | --- |
| 11A | 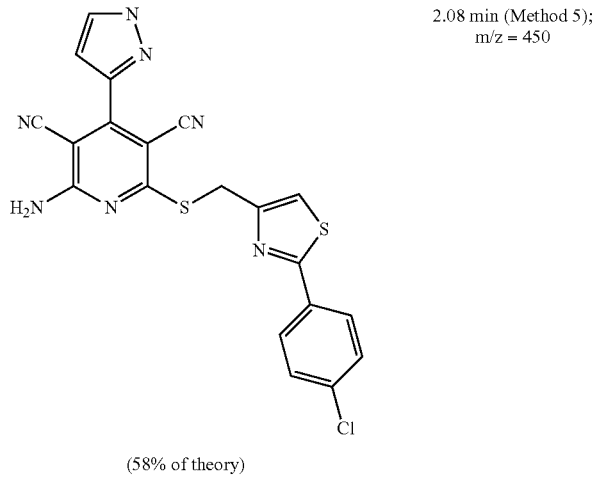<br>(58% of theory) | 2.08 min (Method 5);<br>m/z = 450 |
| 12A | 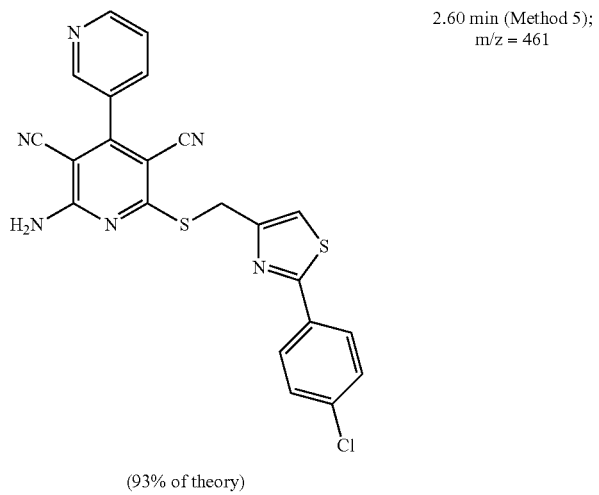<br>(93% of theory) | 2.60 min (Method 5);<br>m/z = 461 |

Example 13A

3-[({6-Chloro-3,5-dicyano-4-[4-(2-hydroxyethoxy)phenyl]pyridin-2-yl}sulfanyl)methyl]-benzoic acid

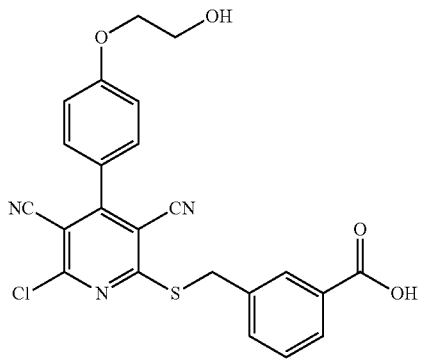 [SMILES: N#Cc1c(Cl)nc(SCc2cccc(C(=O)O)c2)c(C#N)c1-c1ccc(OCCO)cc1]

262 mg (2.24 mmol) of isopentyl nitrite and 301 mg (2.24 mmol) of copper(II) chloride were initially charged in 10.4 ml of acetonitrile. 500 mg (1.12 mmol) of the compound from Example 5A were added, and the mixture was then stirred at 60° C. for 4 h. After cooling to RT, 2.2 ml of 1N hydrochloric acid were added. The aqueous phase was extracted three times with in each case 30 ml of ethyl acetate. The combined organic phases were washed once with saturated aqueous sodium bicarbonate solution, twice with water and once with saturated aqueous sodium chloride solution and dried over sodium sulfate. After removal of the solvent, the product was used without further purification for the subsequent reaction.

Yield: 600 mg (86% of theory, purity 75%)

LC-MS (Method 7): $R_t$=3.23 min; MS (ESIpos): m/z=466 [M+H]$^+$.

The examples listed in Table 2 were prepared analogously to Example 13A from the appropriate starting materials with subsequent purification [preparative HPLC (Chromasil, water/acetonitrile+0.15% conc. hydrochloric acid)]:

TABLE 2

| Example No. | Structure (yield) | LC-MS: $R_t$ [min] (Method); MS (ESI): m/z [M + H]$^+$ |
|---|---|---|
| 14A | 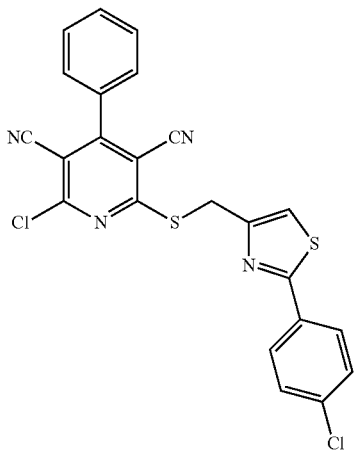<br>(60% of theory) | 3.15 min (Method 2); m/z = 479 |
| 15A | 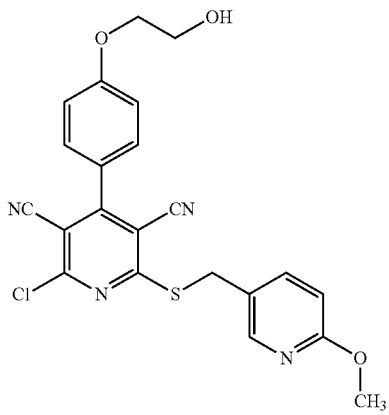<br>(52% of theory) | 3.66 min (Method 4); m/z = 453 |

TABLE 2-continued
| Example No. | Structure (yield) | LC-MS: $R_t$ [min] (Method); MS (ESI): m/z [M + H]+ |
|---|---|---|
| 16A | 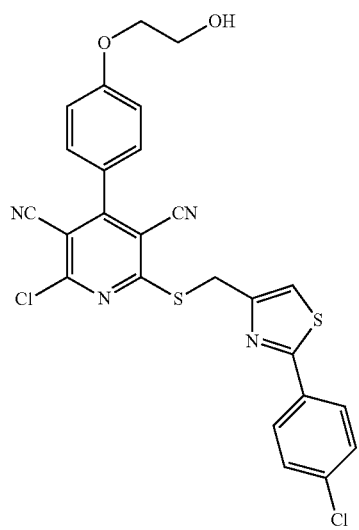<br>(56% of theory) | 3.01 min (Method 11);<br>m/z = 539 |
| 17A | 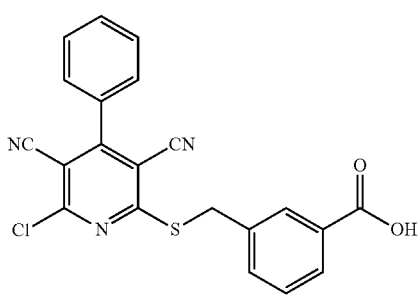<br>(75% of theory) | 3.75 min (Method 4);<br>m/z = 406 |
| 18A | 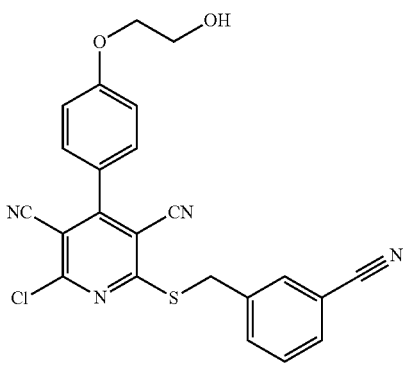<br>(63% of theory) | 4.99 min (Method 10);<br>m/z = 447 |

TABLE 2-continued
| Example No. | Structure (yield) | LC-MS: R$_t$ [min] (Method); MS (ESI): m/z [M + H]$^+$ |
|---|---|---|
| 19A | 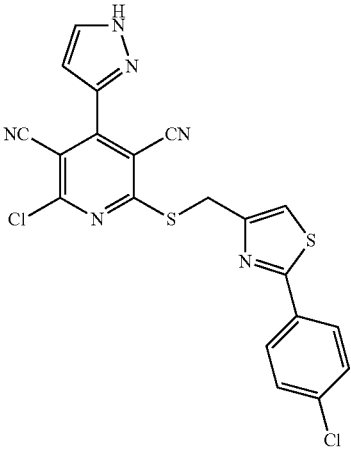 (22% of theory) | 1.49 min (Method 6); m/z = 469 |
| 20A | 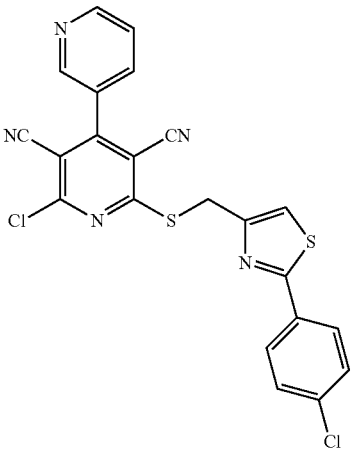 (56% of theory) | 2.94 min (Method 3); m/z = 480 |

Example 21A

Methyl N-{6-({[2-(4-chlorophenyl)-1,3-thiazol-4-yl]methyl}thio)-3,5-dicyano-4-[4-(2-hydroxyethoxy)phenyl]pyridin-2-yl}-N-methylglycinate

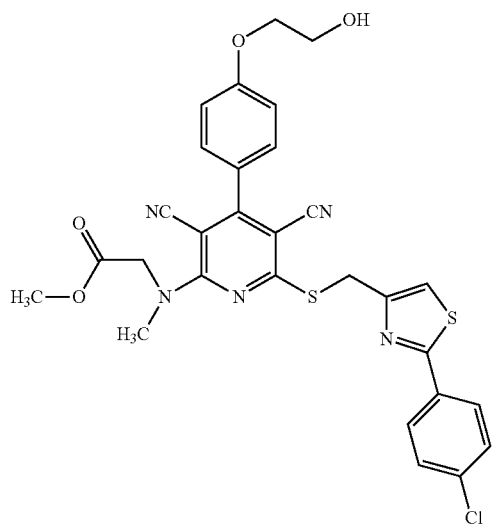 [SMILES: COC(=O)CN(C)c1nc(SCc2csc(-c3ccc(Cl)cc3)n2)c(C#N)c(-c2ccc(OCCO)cc2)c1C#N]

60 mg (0.111 mmol) of the compound from Example 16A, 31 mg (0.222 mmol) of methyl sarcosinate hydrochloride and 0.031 ml (0.222 mmol) of triethylamine in 1.5 ml of THF were stirred at RT overnight. Water was added, and the reaction mixture was extracted three times with ethyl acetate. The combined organic phases were washed with saturated aqueous sodium chloride solution, dried over sodium sulfate and concentrated. The residue was purified by preparative HPLC (Chromasil, water/acetonitrile+0.3% conc. hydrochloric acid).

Yield: 50 mg (74% of theory)

$^1$H-NMR (400 MHz, DMSO-d$_6$): δ=7.98 (d, 2H), 7.70 (s, 1H), 7.61-7.52 (m, 4H), 7.11 (d, 2H), 4.91 (t, 1H), 4.62-4.57 (m, 4H), 4.09 (t, 2H), 3.74 (q, 2H), 3.66 (s, 3H), 3.48 (s, 3H). LC-MS (Method 4): R$_t$=4.13 min; MS (ESIpos): m/z=606 [M+H]$^+$.

The examples listed in Table 3 were prepared analogously to Example 21A from the appropriate starting materials with subsequent purification [preparative HPLC (Chromasil, water/acetonitrile+0.15% conc. hydrochloric acid)]:

TABLE 3

| Example No. | Structure (yield) | LC-MS: R$_t$ [min] (Method); MS (ESI): m/z [M + H]$^+$ | $^1$H-NMR (DMSO-d$_6$): |
|---|---|---|---|
| 22A | (21% of theory) | 4.47 min (Method 4); m/z = 546 | — |

TABLE 3-continued
| Example No. | Structure (yield) | LC-MS: R_t [min] (Method); MS (ESI): m/z [M + H]+ | 1H-NMR (DMSO-d6): |
|---|---|---|---|
| 23A | 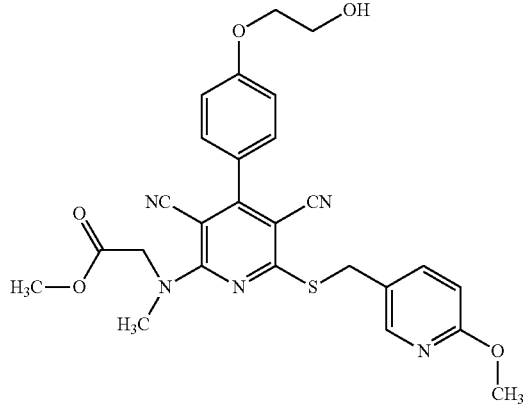 (10% of theory) | 2.38 min (Method 3); m/z = 520 | — |
| 24A | 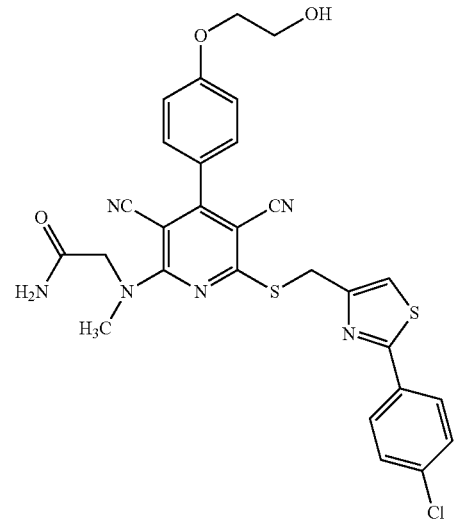 (80% of theory) | 2.28 min (Method 2); m/z = 591 | δ (400 MHz) = 7.98 (d, 2H), 7.71 (s, 1H), 7.61-7.55 (m, 3H), 7.51 (d, 2H), 7.25 (s, 1H), 7.11 (d, 2H), 4.90 (t, 1H), 4.68 (s, 2H), 4.39 (s, 2H), 4.09 (t, 2H), 3.75 (q, 2H), 3.46 (s, 3H). |
| 25A | 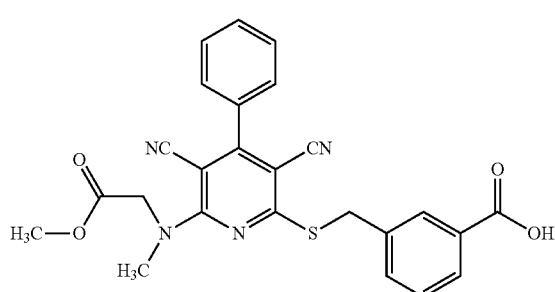 (40% of theory) | 2.53 min (Method 3); m/z = 473 | δ (400 MHz) = 13.08 (s, 1H), 8.00 (s, 1H), 7.87 (d, 1H), 7.65 (d, 1H), 7.61-7.52 (m, 5H), 7.49 (t, 1H), 4.58-4.52 (m, 4H), 3.62 (s, 3H), 3.47 (s, 3H). |

TABLE 3-continued
| Example No. | Structure (yield) | LC-MS: R_t [min] (Method); MS (ESI): m/z [M + H]+ | $^1$H-NMR (DMSO-$d_6$): |
|---|---|---|---|
| 26A | 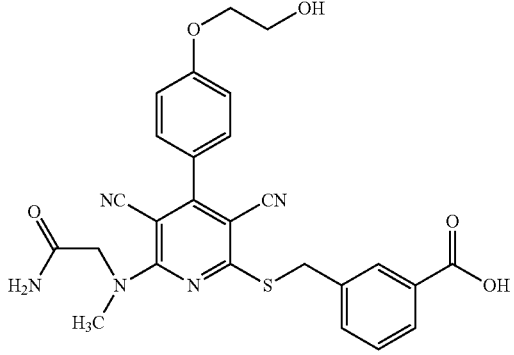 (55% of theory) | 1.56 min (Method 8); m/z = 518 | δ (400 MHz) = 13.06 (s, 1H), 8.00 (s, 1H), 7.87 (d, 1H), 7.68 (d, 1H), 7.59-7.48 (m, 4H), 7.21 (s, 1H), 7.11 (d, 2H), 4.90 (br s, 1H), 4.59 (s, 2H), 4.33 (s, 2H), 4.09 (t, 2H), 3.73 (t, 2H), 3.42 (s, 3H). |
| 27A | 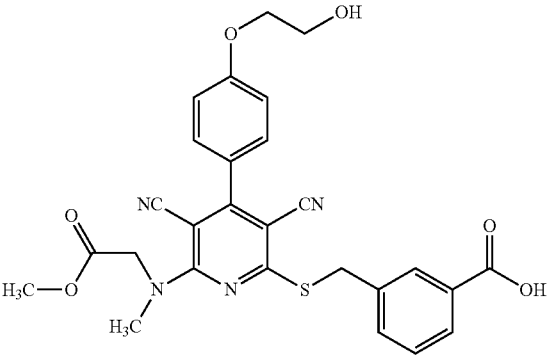 (50% of theory) | 1.87 min (Method 8); m/z = 533 | δ (400 MHz) = 13.06 (s, 1H), 8.00 (s, 1H), 7.87 (d, 1H), 7.66 (d, 1H), 7.58 (d, 2H), 7.50 (t, 1H), 7.11 (d, 2H), 4.90 (br s, 1H), 4.58-4.49 (m, 4H), 4.09 (t, 2H), 3.73 (t, 2H), 3.62 (s, 3H), 3.44 (s, 3H). |
| 28A | 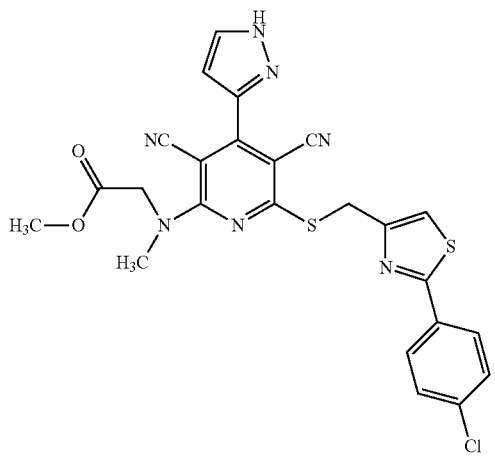 (41% of theory) | 1.38 min (Method 6); m/z = 536 | δ (400 MHz) = 13.61 (s, 1H), 7.99-7.92 (m, 3H), 7.70 (s, 1H), 7.58 (d, 2H), 6.81 (t, 1H), 4.63-54 (m, 4H), 3.67 (s, 3H), 3.47 (s, 3H). |

| Example No. | Structure (yield) | LC-MS: R$_t$ [min] (Method); MS (ESI): m/z [M + H]$^+$ | $^1$H-NMR (DMSO-d$_6$): |
|---|---|---|---|
| 29A | (41% of theory) | 1.42 min (Method 6); m/z = 547 | δ (400 MHz) = 8.82-8.76 (m, 2H), 8.09 (dt, 1H), 7.95 (d, 2H), 7.70 (s, 1H), 7.66-7.56 (m, 3H), 4.64-4.59 (m, 4H), 3.67 (s, 3H), 3.49 (s, 3H). |

Example 30A

Methyl N-{6-({[2-(4-chlorophenyl)-1,3-thiazol-4-yl]methyl}thio)-3,5-dicyano-4-[4-(2-hydroxyethoxy)phenyl]pyridin-2-yl}glycinate 97 mg (0.18 mmol) of the compound from Example 16A, 45 mg (0.36 mmol) of glycine methyl ester hydrochloride and 0.05 ml (0.36 mmol) of triethylamine in 2 ml of THF were stirred at RT for 30 min. After addition of 23 mg (0.18 mmol) of glycine methyl ester hydrochloride and 0.025 ml (0.18 mmol) of triethylamine, the reaction mixture was stirred at RT for 1 h, water was then added and the precipitate formed was filtered off. The precipitate was dried under high vacuum.

Yield: 68 mg (63% of theory)

$^1$H-NMR (400 MHz, DMSO-d$_6$): δ=8.58 (t, 1H), 7.98 (d, 2H), 7.68 (s, 1H), 7.60 (d, 2H), 7.53 (d, 2H), 7.12 (d, 2H), 4.91 (t, 1H), 4.61 (s, 2H), 4.25 (d, 2H), 4.09 (t, 2H), 3.74 (q, 2H), 3.62 (s, 3H).

LC-MS (Method 2): R$_t$=2.64 min; MS (ESIpos): m/z=592 [M+H]$^+$.

Example 31A

Methyl N-(tert-butyloxycarbonyl)-N-[4-(4-{2-[(tert-butyloxycarbonyl)oxy]ethoxy}phenyl)-6-({[2-(4-chlorophenyl)-1,3-thiazol-4-yl]methyl}thio)-3,5-dicyanopyridin-2-yl]glycinate 100 mg (0.17 mmol) of the compound from Example 30A were initially charged in 0.5 ml of absolute dichloromethane, 0.024 ml (0.17 mmol) of triethylamine, 44 mg (0.203 mmol) of di-tert-butyl dicarbonate and 2 mg (0.017 mmol) of 4-dimethylaminopyridine were added and the mixture was stirred at RT overnight. The reaction mixture was diluted with dichloromethane and washed with water. The organic phase was dried over sodium sulfate and concentrated. The residue was purified by column chromatography on silica gel 60 (mobile phase: cyclohexane:ethyl acetate=9:1).

Yield: 92 mg (69% of theory)

$^1$H-NMR (400 MHz, DMSO-d$_6$): δ=7.96 (d, 2H), 7.70 (s, 1H), 7.60-7.52 (m, 4H), 7.21 (d, 2H), 4.62 (s, 2H), 4.60 (s, 2H), 4.40-4.35 (m, 2H), 4.33-4-28 (m, 2H), 3.60 (s, 3H), 1.49 (s, 9H), 1.42 (s, 9H).

LC-MS (Method 4): R$_t$=4.89 min; MS (ESIpos): m/z=792 [M+H]$^+$.

Example 32A

2-Amino-4-[4-(2-{[tert-butyl(dimethyl)silyl]oxy}ethoxy)phenyl]-6-({[2-(4-chlorophenyl)-1,3-thiazol-4-yl]methyl}thio)pyridine-3,5-dicarbonitrile

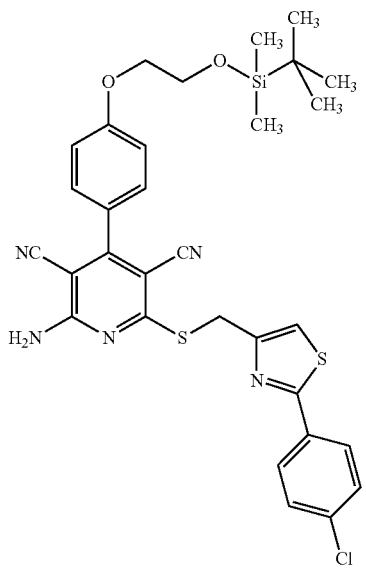 [SMILES: CC(C)(C)[Si](C)(C)OCCOc1ccc(-c2c(C#N)c(N)nc(SCc3csc(-c4ccc(Cl)cc4)n3)c2C#N)cc1]

200 mg (0.385 mmol) of Example 8A were initially charged in 4 ml of dichloromethane, and 161 μl (1.154 mmol) of triethylamine were added. At RT, a solution of 90 mg (0.577 mmol) of tert-butyldimethylsilyl chloride in 1 ml of dichloromethane was added dropwise to the suspension formed, and the mixture was stirred at RT overnight. 2 ml of DMF were added to the reaction mixture, another 29 mg (0.19 mmol) tert-butyldimethylsilyl chloride and 54 ml (0.385 mmol) of triethylamine were added to the solution formed and the mixture was stirred at RT overnight. The dichloromethane was removed on a rotary evaporator and the solution that remained was purified by preparative HPLC (Chromasil, water/acetonitrile).

Yield: 159 mg (65% of theory)

$^1$H-NMR (400 MHz, DMSO-d$_6$): δ=8.12 (br s, 2H), 7.97-7.89 (m, 3H), 7.58 (d, 2H), 7.48 (d, 2H), 7.09 (d, 2H), 4.62 (s, 2H), 4.11 (t, 2H), 3.93 (t, 2H), 0.88 (s, 9H), 0.08 (s, 6H). LC-MS (Method 2): R$_t$=3.37 min; MS (ESIpos): m/z=634 [M+H]$^+$.

Example 33A

Methyl 3-amino-4-[4-(2-{[tert-butyl(dimethyl)silyl]oxy}ethoxy)phenyl]-6-({[2-(4-chlorophenyl)-1,3-thiazol-4-yl]methyl}thio)-5-cyano-1-(2-methoxy-2-oxoethyl)-1H-pyrrolo[2,3-b]pyridine-2-carboxylate

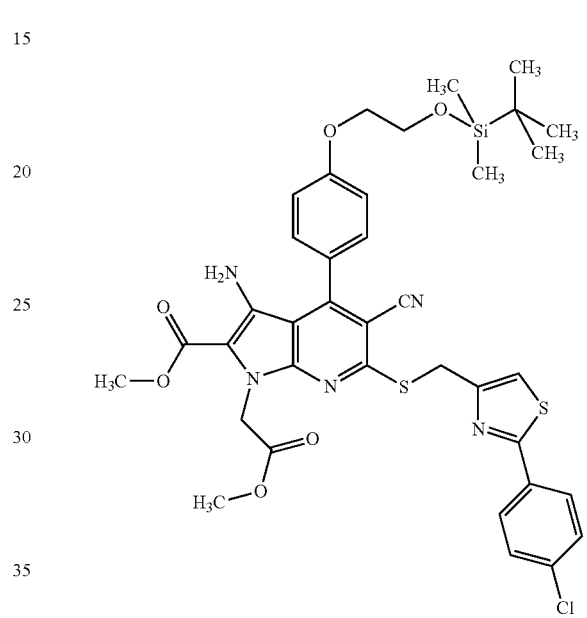

Under argon, 230 mg (0.363 mmol) of the compound from Example 32A were initially charged in 4 ml of DMF, 17 mg (60% pure, 0.435 mmol) of sodium hydride were added a little at a time and the mixture was then stirred at RT for 30 min. A solution of 41 μl (0.435 mmol) of methyl bromoacetate in 1 ml of DMF was then added dropwise, and the resulting solution was stirred at RT overnight. Water was added, and the reaction mixture was extracted three times with ethyl acetate. The combined organic phases were washed with saturated aqueous sodium chloride solution, dried over sodium sulfate and concentrated. The residue was purified by preparative HPLC (Chromasil, water/acetonitrile).

Yield: 23 mg (8% of theory)

$^1$H-NMR (500 MHz, DMSO-d$_6$): δ=7.97 (d, 2H), 7.64 (s, 1H), 7.59 (d, 2H), 7.49 (d, 2H), 7.18 (d, 2H), 5.31 (s, 2H), 4.93 (br s, 2H), 4.74 (s, 2H), 4.14 (t, 2H), 3.98 (t, 2H), 3.73 (s, 3H), 3.62 (s, 3H), 0.89 (s, 9H), 0.10 (s, 6H).

LC-MS (Method 2): R$_t$=3.47 min; MS (ESIpos): m/z=778 [M+H]$^+$.

Example 34A

N-{6-({[2-(4-Chlorophenyl)-1,3-thiazol-4-yl]methyl}thio)-3,5-dicyano-4-[4-(2-hydroxyethoxy)phenyl]pyridin-2-yl}-N-methylglycine

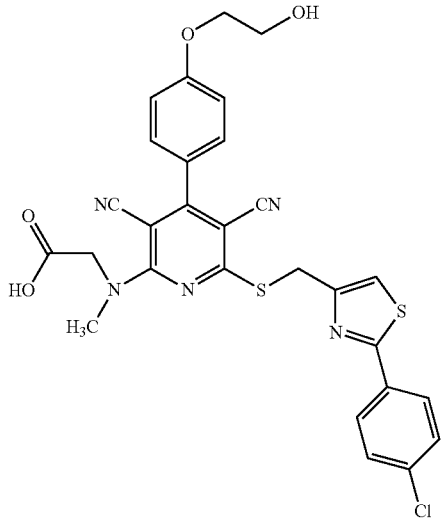 [SMILES: CN(CC(=O)O)c1nc(SCc2csc(-c3ccc(Cl)cc3)n2)c(C#N)c(-c2ccc(OCCO)cc2)c1C#N]

A solution of 89 mg (1 mmol) of sarcosine in 1 ml of 1N aqueous sodium hydroxide solution was added to a solution of 300 mg (0.5 mmol) of the compound from Example 16A in 6 ml of 1,4-dioxane, and the mixture was then stirred at RT for 3 h. Water and then 1N hydrochloric acid were added, and the reaction mixture was extracted three times with ethyl acetate. The combined organic phases were washed with saturated aqueous sodium chloride solution, dried over sodium sulfate and concentrated. The residue was purified by preparative HPLC (Chromasil, water/acetonitrile+0.15% conc. hydrochloric acid).

Yield: 211 mg (68% of theory)

$^1$H-NMR (500 MHz, DMSO-$d_6$): δ=7.94 (d, 2H), 7.79 (s, 1H), 7.57 (d, 2H), 7.50 (d, 2H), 7.10 (d, 2H), 4.93 (br s, 1H), 4.63 (s, 2H), 4.38 (s, 2H), 4.09 (t, 2H), 3.73 (t, 2H), 3.44 (s, 3H).

LC-MS (Method 2): $R_t$=3.79 min; MS (ESIpos): m/z=592 [M+H]$^+$.

Example 35A

Methyl N-{3,5-dicyano-6-[(3-cyanobenzyl)thio]-4-[4-(2-hydroxyethoxy)phenyl]pyridin-2-yl}-N-methylglycinate

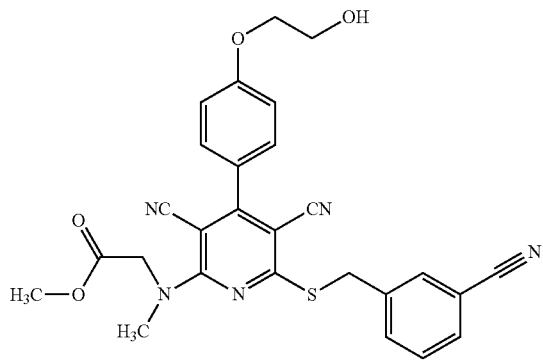 [SMILES: COC(=O)CN(C)c1nc(SCc2cccc(C#N)c2)c(C#N)c(-c2ccc(OCCO)cc2)c1C#N]

A solution of 155 mg (1.11 mmol) of methyl sarcosinate in 1.1 ml of 1N aqueous sodium hydroxide solution was added to a solution of 300 mg (0.56 mmol) of the compound from Example 18A in 7.3 ml of 1,4-dioxane, and the mixture was then stirred at RT overnight. The same amounts of methyl sarcosinate and sodium hydroxide solution were then added again, and the mixture was stirred at RT for 4 h. Water was added, and the reaction mixture was extracted three times with ethyl acetate. The combined organic phases were washed with saturated aqueous sodium chloride solution, dried over sodium sulfate and concentrated. The residue was purified by preparative HPLC (Chromasil, water/acetonitrile+0.15% conc. hydrochloric acid).

Yield: 179 mg (62% of theory)

$^1$H-NMR (500 MHz, DMSO-$d_6$): δ=7.87 (s, 1H), 7.79 (d, 1H), 7.74 (d, 1H), 7.59-7.53 (m, 3H), 7.11 (d, 2H), 4.92 (t, 1H), 4.54 (s, 2H), 4.52 (s, 2H), 4.09 (t, 2H), 3.75 (q, 2H), 3.61 (s, 3H), 3.44 (s, 3H).

LC-MS (Method 7): $R_t$=3.28 min; MS (ESIpos): m/z=514 [M+H]$^+$.

Example 36A $N^2$-{6-({[2-(4-Chlorophenyl)-1,3-thiazol-4-yl]methyl}sulfanyl)-3,5-dicyano-4-[4-(2-hydroxyethoxy)phenyl]pyridin-2-yl}-$N,N^2$-dimethylglycinamide

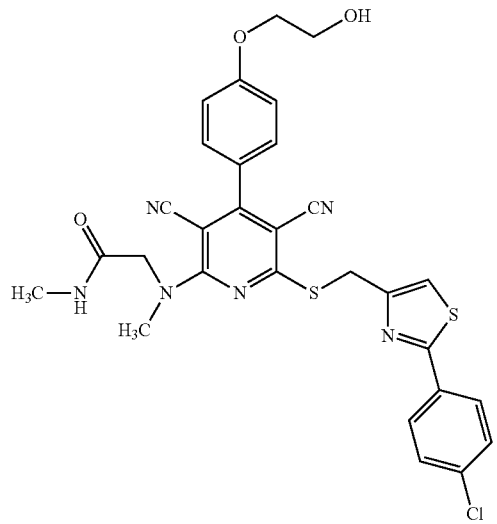 [SMILES: CNC(=O)CN(C)c1nc(SCc2csc(-c3ccc(Cl)cc3)n2)c(C#N)c(-c2ccc(OCCO)cc2)c1C#N]

100 mg (0.162 mmol) of the compound from Example 34A were initially charged in 2 ml of DMF, cooled to 0° C., and 123 mg (0.324 mmol) of HATU were added. After 20 min, 243 μl (0.486 mmol) of methylamine and 56 ml (0.324 mmol) of N,N-diisopropylethylamine were added, and the mixture was then stirred at RT overnight. Water was added, and the reaction mixture was extracted three times with ethyl acetate. The combined organic phases were washed with saturated aqueous sodium chloride solution, dried over sodium sulfate and concentrated. The residue was purified by preparative HPLC (Chromasil, water/acetonitrile+0.15% conc. hydrochloric acid). This gave 37 mg of the desired compound. In addition, more solid precipitated from the aqueous phase overnight; this was filtered off and washed with a little water. This gave another 50 mg of the desired compound.

Total yield: 87 mg (86% of theory)

$^1$H-NMR (500 MHz, DMSO-$d_6$): δ=8.03-7.92 (m, 3H), 7.70 (s, 1H), 7.59 (d, 2H), 7.51 (d, 2H), 7.12 (d, 2H), 4.61 (s,

2H), 4.39 (s, 2H), 4.09 (t, 2H), 3.73 (t, 2H), 3.44 (s, 3H), 2.61 (d, 3H).

LC-MS (Method 3): $R_t$=2.60 min; MS (ESIpos): m/z=605 [M+H]$^+$.

Example 37A

4-{[(4R)-2,2-Dimethyl-1,3-dioxolan-4-yl]methoxy}benzaldehyde

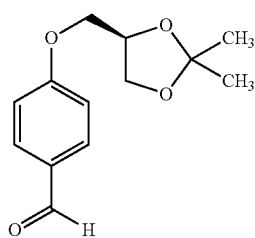 [SMILES: CC1(C)OC[C@@H](COc2ccc(C=O)cc2)O1]

31.2 g (255.4 mmol) of 4-hydroxybenzaldehyde were initially charged in 400 ml of dry DMF, and 105.7 g (766.1 mmol) of potassium carbonate and 50.0 g (332.0 mmol) of (S)-(−)-3-chloro-1,2-propanediol acetonide were added at RT. The mixture was stirred at 160° C. for 16 h. 4000 ml of water were then added, and the mixture was extracted three times with in each case 500 ml of ethyl acetate. The combined organic phases were washed in each case once with 500 ml of water and 500 ml of saturated aqueous sodium chloride solution. After drying over magnesium sulfate, the solvent was removed on a rotary evaporator and the residue was purified by column chromatography on silica gel 60 (mobile phase gradient: ethyl acetate/petroleum ether 1:9→2:8).

Yield: 40.4 g (63% of theory)

$^1$H-NMR (400 MHz, DMSO-d$_6$): δ=9.90 (s, 1H), 7.85 (d, 2H), 7.03 (d, 2H), 4.50 (q, 1H), 4.22-4.09 (m, 2H), 4.04 (dd, 1H), 3.92 (dd, 1H), 1.48 (s, 3H), 1.41 (s, 3H).

LC-MS (Method 12): $R_t$=3.97 min; MS (ESIpos): m/z=254 [M+NH$_4$]$^+$.

Example 38A

2-Amino-4-(4-{[(4R)-2,2-dimethyl-1,3-dioxolan-4-yl]methoxy}phenyl)-6-mercaptopyridine-3,5-dicarbonitrile

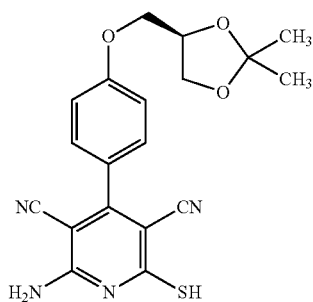 [SMILES: CC1(C)OC[C@@H](COc2ccc(-c3c(C#N)c(N)nc(S)c3C#N)cc2)O1]

40.4 g (171.0 mmol) of the compound from Example 37A and 34.2 g (342.0 mmol) of cyanothioacetamide were initially charged in 700 ml of ethanol. 34.5 g (342.0 mmol) of 4-methyl morpholine were added, and the reaction mixture was heated under reflux with stirring for 3 h. After cooling to RT, the mixture was stirred at this temperature for a further 16 h. The resulting precipitate was filtered off with suction, washed with about 100 ml of ethanol and dried in a drying cabinet. The product was used without further purification for the subsequent reactions.

Yield: 19.5 g (29% of theory)

$^1$H-NMR (400 MHz, DMSO-d$_6$): δ=7.63-7.31 (br s, 2H), 7.41 (d, 2H), 7.09 (d, 2H), 4.49-4.38 (m, 1H), 4.15-3.99 (m, 2H), 3.78 (dd, 1H), 3.66 (dd, 1H), 2.77-2.68 (br s, 1H), 1.37 (s, 3H), 1.32 (s, 3H).

LC-MS (Method 9): $R_t$=1.95 min; MS (ESIpos): m/z=424 [M+H+CH$_3$CN]$^+$.

Example 39A

2-Amino-6-({[2-(4-chlorophenyl)-1,3-oxazol-4-yl]methyl}sulfanyl)-4-(4-{[(4R)-2,2-dimethyl-1,3-dioxolan-4-yl]methoxy}phenyl)pyridine-3,5-dicarbonitrile

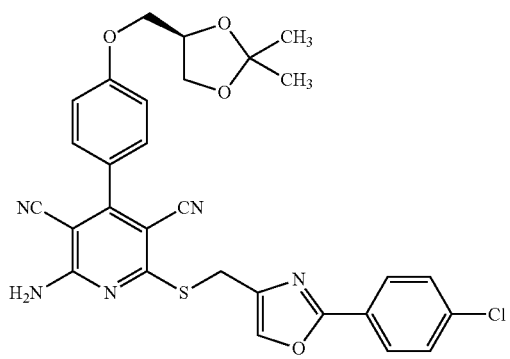 [SMILES: CC1(C)OC[C@@H](COc2ccc(-c3c(C#N)c(N)nc(SCc4coc(-c5ccc(Cl)cc5)n4)c3C#N)cc2)O1]

70 mg (0.18 mmol) of the compound from Example 38A and 46 mg (0.20 mmol) of 4-(chloromethyl)-2-(4-chlorophenyl)-1,3-oxazole together with 46 mg (0.55 mmol) of sodium bicarbonate were suspended in 1.9 ml of dry DMF. The reaction mixture was stirred at RT for 20 h. The mixture was then freed from the solvent on a rotary evaporator, and the residue was purified by preparative HPLC (column: YMC GEL ODS-AQ S-5/15 μm; mobile phase gradient: acetonitrile/water 10:90→95:5).

Yield: 79 mg (75% of theory)

$^1$H-NMR (400 MHz, DMSO-d$_6$): δ=8.37 (s, 1H), 8.30-8.01 (br s, 2H), 7.97 (d, 2H), 7.60 (d, 2H), 7.48 (d, 2H), 7.12 (d, 2H), 4.48-4.40 (m, 1H), 4.42 (s, 2H), 4.16-4.03 (m, 3H), 3.78 (dd, 1H), 1.37 (s, 3H), 1.31 (s, 3H).

LC-MS (Method 3): $R_t$=2.99 min; MS (ESIpos): m/z=574 [M+H]$^+$.

Example 40A

2-Amino-6-({[2-(4-chlorophenyl)-1,3-oxazol-4-yl]methyl}sulfanyl)-4-(4-{[(2S)-2,3-dihydroxypropyl]oxy}phenyl)pyridine-3,5-dicarbonitrile

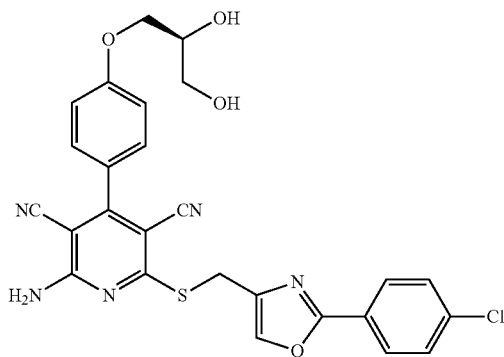 [SMILES: N#Cc1c(N)nc(SCc2coc(-c3ccc(Cl)cc3)n2)c(C#N)c1-c1ccc(OC[C@@H](O)CO)cc1]

400 mg (0.70 mmol) of the compound from Example 39A were initially charged in 17 ml of acetic acid, and 8.6 ml of water were then added carefully. The mixture was stirred at RT for 12 h. The reaction mixture was concentrated on a rotary evaporator, and the residue was then purified directly by preparative HPLC (column: YMC GEL ODS-AQ S-5/15 µm; mobile phase gradient: acetonitrile/water 10:90→95:5). Removal of the solvent on a rotary evaporator gave the product as a solid.

Yield: 340 mg (91% of theory)

$^1$H-NMR (400 MHz, DMSO-d$_6$): δ=8.37 (s, 1H), 8.27-7.91 (br s, 2H), 7.98 (d, 2H), 7.60 (d, 2H), 7.47 (d, 2H), 7.10 (d, 2H), 5.00 (d, 1H), 4.70 (t, 1H), 4.42 (s, 2H), 4.09 (dd, 1H), 3.96 (dd, 1H), 3.70 (q, 1H), 3.46 (t, 2H).

LC-MS (Method 3): R$_t$=2.48 min; MS (ESIpos): m/z=534 [M+H]$^+$.

Example 41A

2-Chloro-6-({[2-(4-chlorophenyl)-1,3-oxazol-4-yl]methyl}thio)-4-(4-{[(2S)-2,3-dihydroxypropyl]oxy}phenyl)pyridine-3,5-dicarbonitrile

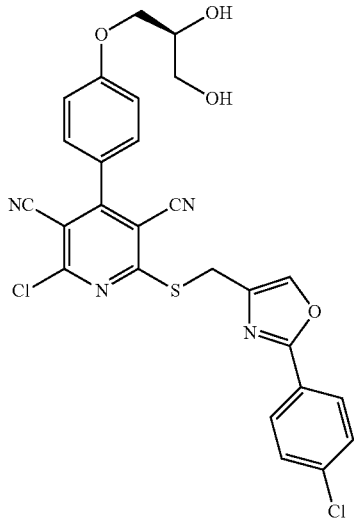 [SMILES: N#Cc1c(Cl)nc(SCc2coc(-c3ccc(Cl)cc3)n2)c(C#N)c1-c1ccc(OC[C@@H](O)CO)cc1]

171 mg (1.46 mmol) of isopentyl nitrite and 196 mg (1.46 mmol) of copper(II) chloride were initially charged in 18 ml of acetonitrile. 389 mg (0.73 mmol) of the compound from Example 40A were added, and the mixture was then stirred at 60° C. for 3 h. After cooling to RT, 20 ml of 1N hydrochloric acid were added. The aqueous phase was extracted twice with in each case 30 ml of ethyl acetate. The combined organic phases were dried over magnesium sulfate. The solvent was removed, and the product was then used without further purification for the subsequent reaction.

Yield: 451 mg (77% of theory, purity 69%)

LC-MS (Method 3): R$_t$=2.84 min; MS (ESIpos): m/z=553 [M+H]$^+$.

Example 42A

Methyl N-[6-({[2-(4-chlorophenyl)-1,3-oxazol-4-yl]methyl}thio)-3,5-dicyano-4-(4-{[(2S)-2,3-dihydroxypropyl]oxy}phenyl)pyridin-2-yl]-N-methylglycinate

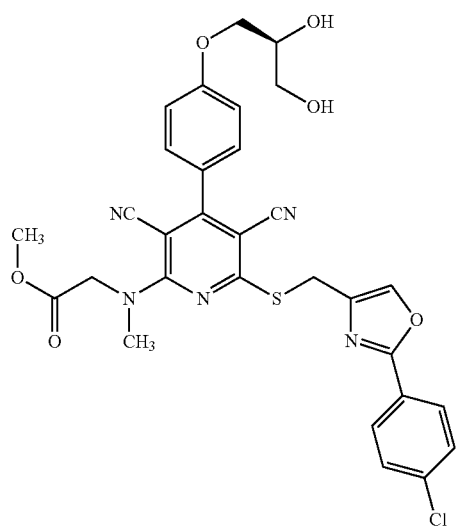 [SMILES: COC(=O)CN(C)c1nc(SCc2coc(-c3ccc(Cl)cc3)n2)c(C#N)c(-c2ccc(OC[C@@H](O)CO)cc2)c1C#N]

451 mg (0.51 mmol) of the compound from Example 40A were dissolved in 7.8 ml of dry THF, and 141 mg (1.01 mmol) of methyl sarcosinate hydrochloride and 211 µl (1.52 mmol) of triethylamine were then added in succession. The reaction mixture was stirred at RT for 8 h. After removal of the solvent, the mixture was purified directly by preparative HPLC (column: YMC GEL ODS-AQ S-5/15 µm; mobile phase gradient: acetonitrile/water 10:90→95:5).

Yield: 52 mg (15% of theory)

$^1$H-NMR (400 MHz, DMSO-d$_6$): δ=8.19 (s, 1H), 7.98 (d, 2H), 7.62 (d, 2H), 7.55 (d, 2H), 7.11 (d, 2H), 5.01 (d, 1H), 4.70 (t, 1H), 4.61 (s, 2H), 4.42 (s, 2H), 4.09 (dd, 1H), 3.96 (dd, 1H), 3.87-3.78 (m, 1H), 3.65 (s, 3H), 3.52-3.43 (m, 5H).

LC-MS (Method 3): R$_t$=2.70 min; MS (ESIpos): m/z=620 [M+H]$^+$.

Example 43A

2-Amino-6-mercapto-4-(methylthio)pyridine-3,5-dicarbonitrile

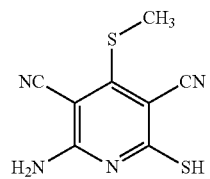

10 g (58.74 mmol) of 2-(di(methylthio))methylidenemalononitrile and 7.1 g (70.48 mmol) of cyanothioacetamide were initially charged in 21 ml of DMF, and 16.4 ml (117.47 mmol) of triethylamine were added dropwise at room temperature. The mixture was stirred at room temperature for 8 h. The reaction mixture was added to 300 ml of 3N hydrochloric acid. The resulting precipitate was filtered off with suction, washed with water and dried. This gave the product as a powder.

Yield: 12.2 g (89% of theory, 96% pure)

$^1$H-NMR (400 MHz, CDCl$_3$): δ=3.98 (s, 1H), 2.72 (s, 3H).

LC-MS (Method 7): R$_t$=1.56 min; MS (ESIpos): m/z=223 [M+H]$^+$.

Example 44A

2-Amino-6-({[2-(4-chlorophenyl)-1,3-thiazol-4-yl]methyl}thio)-4-(methylthio)pyridine-3,5-dicarbonitrile

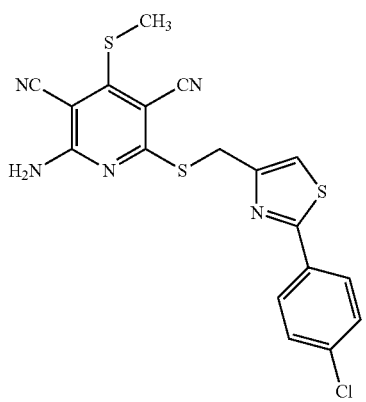 [SMILES: CSc1c(C#N)c(N)nc(SCc2csc(-c3ccc(Cl)cc3)n2)c1C#N]

7.30 g (32.84 mmol) of the compound from Example 43A (2-amino-6-mercapto-4-(methylthio)pyridine-3,5-dicarbonitrile), 11.03 g (131.36 mmol) of sodium bicarbonate and 9.62 g (39.41 mmol) of 4-(chloromethyl)-2-(4-chlorophenyl)-1,3-thiazole were combined in 150 ml of absolute DMF and stirred at room temperature for 12 h. A solid precipitated out; this solid was filtered off with suction through a glass frit and washed three times with water and twice with diethyl ether. The residue was dried under reduced pressure.

Yield: 14.2 g (99% of theory)

$^1$H-NMR (400 MHz, CDCl$_3$): δ=8.14-8.05 (br s, 2H), 7.96 (d, 2H), 7.87 (s, 1H), 7.58 (d, 2H), 4.58 (s, 2H), 2.72 (s, 3H).

LC-MS (Method 2): R$_t$=2.67 min; MS (ESIpos): m/z=430 [M+H]$^+$.

Example 45A

2-Amino-6-({[2-(4-chlorophenyl)-1,3-thiazol-4-yl]methyl}sulfanyl)-4-piperidin-1-ylpyridine-3,5-dicarbonitrile

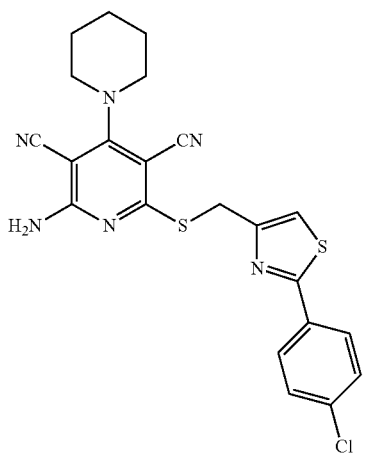 [SMILES: N#Cc1c(N)nc(SCc2csc(-c3ccc(Cl)cc3)n2)c(C#N)c1N1CCCCC1]

5.00 g (11.63 mmol) of the compound from Example 44A and 57.50 ml (581.43 mmol) of piperidine were initially charged in 120 ml of acetone and heated at reflux for 8 h. After cooling, the mixture was poured into a solvent mixture of 50 ml of saturated aqueous ammonium chloride solution and 50 ml of ethyl acetate. The phases were separated. The organic phase was washed twice with in each case 20 ml of saturated aqueous sodium chloride solution and then dried over magnesium sulfate. After removal of the solvent, the residue was triturated with 100 ml of diethyl ether. The precipitate was filtered off with suction and dried under reduced pressure at 50° C.

Yield: 2.00 g (37% of theory)

$^1$H-NMR (400 MHz, CDCl$_3$): δ=7.94 (d, 2H), 7.82 (s, 1H), 7.75-7.59 (br s, 2H), 7.55 (d, 2H), 4.53 (s, 2H), 3.48 (br s, 4H), 1.61 (br s, 6H).

LC-MS (Method 2): R$_t$=2.90 min; MS (ESIpos): m/z=467 [M+H]$^+$.

Example 46A

2-Chloro-6-({[2-(4-chlorophenyl)-1,3-thiazol-4-yl]methyl}sulfanyl)-4-piperidin-1-ylpyridine-3,5-dicarbonitrile

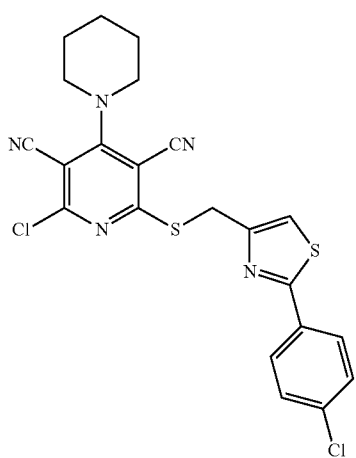 [SMILES: N#Cc1c(Cl)nc(SCc2csc(-c3ccc(Cl)cc3)n2)c(C#N)c1N1CCCCC1]

3.85 g (29.55 mmol) of isopentyl nitrite and 3.97 g (29.55 mmol) of copper(II) chloride were initially charged in 40 ml of acetonitrile, and 2.30 g (4.93 mmol) of the compound from Example 45A were added. The reaction mixture was stirred at 60° C. for 3 h. 20 ml of 1N hydrochloric acid were added to the reaction solution. The aqueous phase was extracted twice with in each case 40 ml of ethyl acetate. The combined organic phases were washed in each case once with 20 ml of saturated aqueous sodium bicarbonate solution and saturated aqueous sodium chloride solution and then dried over magnesium sulfate. The solvent was removed on a rotary evaporator. The residue was purified by column chromatography on silica gel 60 (mobile phase gradient cyclohexane:ethyl acetate=10:1→1:4).

Yield: 1.50 g (60% of theory)

$^1$H-NMR (400 MHz, CDCl$_3$): δ=7.94 (d, 2H), 7.67 (s, 1H), 7.57 (d, 2H), 4.53 (s, 2H), 3.68-3.59 (br s, 4H), 1.71-1.59 (br s, 6H).

LC-MS (Method 2): R$_t$=2.79 min; MS (ESIpos): m/z=509 [M+H]$^+$.

Example 47A

Methyl N-[6-({[2-(4-chlorophenyl)-1,3-thiazol-4-yl]methyl}sulfanyl)-3,5-dicyano-4-piperidin-1-ylpyridin-2-yl]-N-methylglycinate

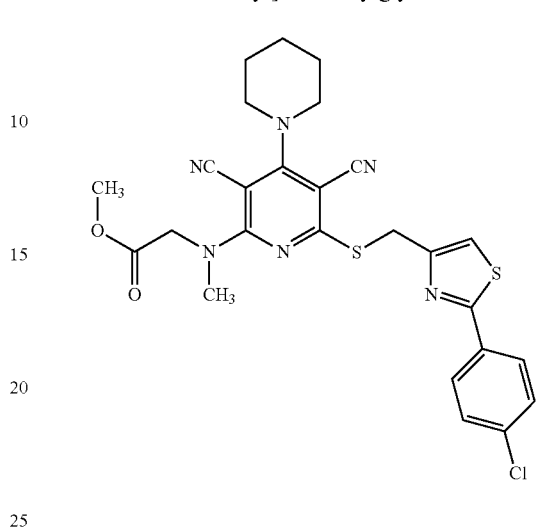

100 mg (0.21 mmol) of the compound from Example 46A were dissolved in 2 ml of dry THF. 57 mg (0.41 mmol) of methyl sarcosinate hydrochloride and 86 µl (0.62 mmol) of triethylamine were then added in succession. The reaction mixture was stirred at RT for 10 h. 1 ml of water was added, and the mixture was extracted three times with in each case 5 ml of ethyl acetate. The combined organic phases were washed once with 3 ml of saturated aqueous sodium chloride solution and dried over magnesium sulfate. After removal of the solvent on a rotary evaporator, the residue was purified by preparative HPLC (column: YMC GEL ODS-AQ S-5/15 µm; mobile phase gradient: acetonitrile/water 10:90→95:5).

Yield: 80 mg (70% of theory)

$^1$H-NMR (400 MHz, CDCl$_3$): δ=7.95 (d, 2H), 7.62 (s, 1H), 7.58 (d, 2H), 4.51 (s, 2H), 4.46 (s, 2H), 3.13 (s, 3H), 3.07 (br s, 4H), 3.31 (s, 3H), 1.65 (br s, 6H).

LC-MS (Method 3): R$_t$=3.24 min; MS (ESIpos): m/z=553 [M].

Example 48A

2-Amino-4-[4-(2-hydroxyethoxy)phenyl]-6-(phenylsulfanyl)pyridine-3,5-dicarbonitrile

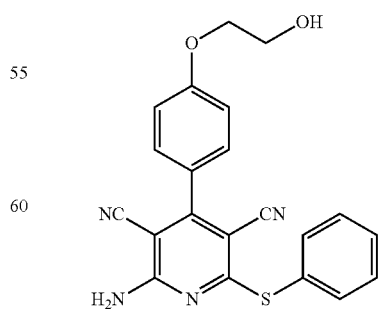

100.0 g (601.8 mmol) of 4-(2-hydroxyethoxy)benzaldehyde were initially charged in 600 ml of absolute ethanol, 40 g (605.5 mmol) of malononitrile and 1 ml (7.22 mmol) of triethylamine were added and the mixture was heated at reflux for 2 h. The heating bath was removed, and 43.5 g (658.2 mmol) of malononitrile, 1.5 ml (10.83 mmol) of triethylamine and 66.3 g (601.8 mmol) of thiophenol were added to the mixture. The mixture was heated at reflux for another 2 h and then stirred at room temperature for 8 h. The reaction solution was cooled to 5° C., and the precipitate formed was filtered off with suction. The precipitate was washed with 500 ml of tert-butyl methyl ether. The residue was taken up in 400 ml of DMF and heated to 70° C. A solution of 141.1 g (257.4 mmol) of ammonium cerium(IV) nitrate in 250 ml of water of a temperature of 50° C. was then added dropwise. During the addition, a further 500 ml of DMF were added. After the addition, the mixture was stirred at RT for 1 h. 1000 ml of water were then added, and the reaction mixture was stirred at RT for 16 h. The resulting precipitate was filtered off with suction and washed with water. The residue was dried under reduced pressure.

Yield: 95.2 g (89% of theory).

$^1$H-NMR (400 MHz, DMSO-$d_6$): δ=7.83-7.19 (br s, 2H), 7.64-7.58 (m, 2H), 7.53-7.48 (m, 5H), 7.12 (d, 2H), 5.10-4.75 (br s, 1H), 4.10 (t, 2H), 3.75 (t, 2H).

LC-MS (Method 5): $R_t$=1.76 min; MS (ESIpos): m/z=389 [M+H]$^+$.

Example 49A

2-Amino-6-{[2-(4-chlorophenyl)-1,3-oxazol-4-yl]methoxy}-4-[4-(2-hydroxyethoxy)phenyl]-pyridine-3,5-dicarbonitrile

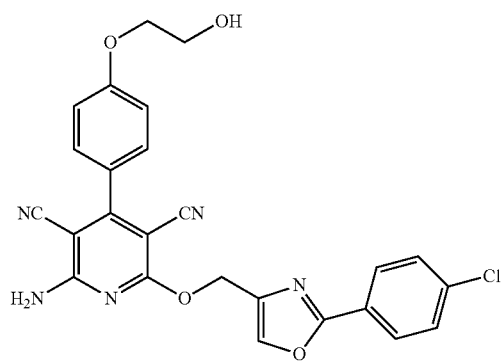 [SMILES: N#Cc1c(N)nc(OCc2coc(-c3ccc(Cl)cc3)n2)c(C#N)c1-c1ccc(OCCO)cc1]

72 mg (0.64 mmol) of potassium tert-butoxide were suspended in 1 ml of dry dimethoxyethane. 270 mg (1.29 mmol) of [2-(4-chlorophenyl)-1,3-oxazol-4-yl]methanol and 50 mg (0.13 mmol) of the compound from Example 48A were then added in succession. The reaction mixture was stirred at 60° C. for 2 h and then cooled to RT and stirred at this temperature for 8 h. 5 ml of water and 1 ml of 2N acetic acid were added to the reaction mixture. A precipitate is formed, which was filtered off with suction. The residue was purified by preparative HPLC (column: YMC GEL ODS-AQ S-5/15 μm; mobile phase gradient: acetonitrile/water 10:90→95:5). Removal of the solvent on a rotary evaporator gave the product as a solid.

Yield: 44 mg (70% of theory).

$^1$H-NMR (400 MHz, DMSO-$d_6$): δ=8.48 (s, 1H), 8.18-7.85 (br s, 2H), 8.00 (d, 2H), 7.62 (d, 2H), 7.48 (d, 2H), 7.11 (d, 2H), 5.41 (s, 2H), 4.91 (t, 1H), 4.08 (t, 2H), 3.73 (q, 2H).

LC-MS (Method 6): $R_t$=1.22 min; MS (ESIpos): m/z=488 [M+H]$^+$.

Example 50A

2-Chloro-6-{[2-(4-chlorophenyl)-1,3-oxazol-4-yl]methoxy}-4-[4-(2-hydroxyethoxy)phenyl]-pyridine-3,5-dicarbonitrile

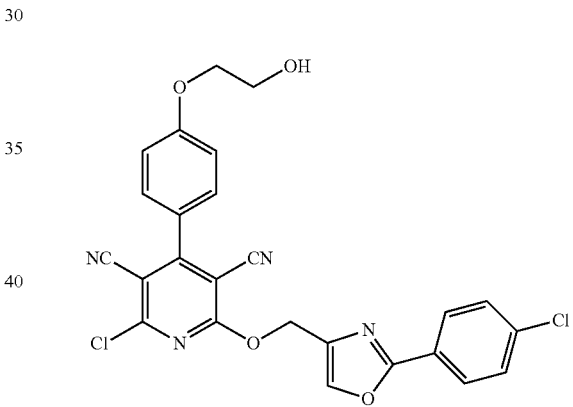

78 mg (0.67 mmol) of isopentyl nitrite and 90 mg (0.67 mmol) of copper(II) chloride were initially charged in 8.5 ml of acetonitrile, and 72 mg (0.64 mmol) of the compound from Example 49A were added. The reaction mixture was stirred at 60° C. for 3 h. 8.5 ml of 1N hydrochloric acid were added to the reaction solution. The aqueous phase was extracted twice with in each case 20 ml of ethyl acetate, and the combined organic phases were dried over magnesium sulfate. After removal of the solvent on a rotary evaporator, the residue was dried under reduced pressure and used without further purification for the subsequent reaction.

Yield: 231 mg (87% of theory, 64% pure).

LC-MS (Method 6): $R_t$=1.40 min; MS (ESIpos): m/z=507 [M]$^+$.

Example 51A

Methyl N-(6-{[2-(4-chlorophenyl)-1,3-oxazol-4-yl]methoxy}-3,5-dicyano-4-[4-(2-hydroxyethoxy)phenyl]pyridin-2-yl)-N-methylglycinate

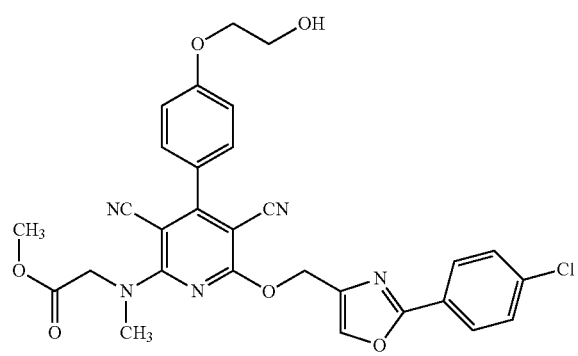 [SMILES: COC(=O)CN(C)c1nc(OCc2coc(-c3ccc(Cl)cc3)n2)c(C#N)c(-c2ccc(OCCO)cc2)c1C#N]

230 mg (about 0.45 mmol) of the crude product from Example 50A were dissolved in 3 ml of absolute THF, and 127 mg (0.91 mmol) of methyl sarcosinate hydrochloride and 138 mg (1.36 mmol) of triethylamine were added. The reaction mixture was stirred at RT for 10 h. After removal of the solvent on a rotary evaporator, the residue was purified directly by preparative HPLC (column: YMC GEL ODS-AQ S-5/15 µm; mobile phase gradient: acetonitrile/water 10:90→95:5). Removal of the solvent on a rotary evaporator gave the product as a white solid.

Yield: 24 mg (9% of theory).

$^1$H-NMR (400 MHz, DMSO-$d_6$): δ=8.34 (s, 1H), 8.00 (d, 2H), 7.62 (d, 2H), 7.53 (d, 2H), 7.11 (d, 2H), 5.39 (s, 2H), 4.98-4.86 (br s, 1H), 4.58 (s, 2H), 4.09 (t, 2H), 3.78-3.71 (m, 2H), 3.68 (s, 3H), 3.49 (s, 3H).

LC-MS (Method 3): $R_t$=2.59 min; MS (ESIpos): m/z=574 [M+H]$^+$.

Working Examples

Example 1

Methyl 3-amino-6-({[2-(4-chlorophenyl)-1,3-thiazol-4-yl]methyl}thio)-5-cyano-4-[4-(2-hydroxyethoxy)phenyl]-1-methyl-1H-pyrrolo[2,3-b]pyridine-2-carboxylate

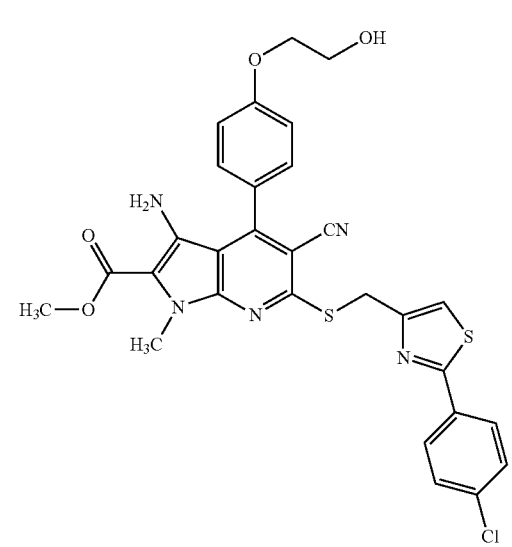 [SMILES: COC(=O)c1c(N)c2c(-c3ccc(OCCO)cc3)c(C#N)c(SCc3csc(-c4ccc(Cl)cc4)n3)nc2n1C]

21 mg (0.035 mmol) of the compound from Example 21A were initially charged in 0.69 ml of acetonitrile, and 45 mg (0.139 mmol) of cesium carbonate were added. The reaction mixture was stirred at 50° C. for 2 h and then cooled. The solid was filtered off and then washed with acetonitrile. The filtrate was concentrated and the residue was dried under high vacuum.

Yield: 17 mg (81% of theory)

$^1$H-NMR (400 MHz, DMSO-$d_6$): δ=7.96 (d, 2H), 7.72 (s, 1H), 7.58 (d, 2H), 7.48 (d, 2H), 7.16 (d, 2H), 4.96-4.87 (m, 3H), 4.79 (s, 2H), 4.10 (t, 2H), 3.96 (s, 3H), 3.80 (s, 3H), 3.78 (q, 2H).

LC-MS (Method 3): $R_t$=3.16 min; MS (ESIpos): m/z=606 [M+H]$^+$.

The examples listed in Table 4 were prepared from the appropriate starting materials analogously to Example 1 with subsequent purification [preparative HPLC (Chromasil, water/acetonitrile+0.15% conc. hydrochloric acid)]:

TABLE 4
| Example No. | Structure (yield) | LC-MS: $R_t$ [min] (Method);<br>MS (ESI): m/z [M + H]⁺ | ¹H-NMR<br>(DMSO-$d_6$): |
|---|---|---|---|
| 2 | 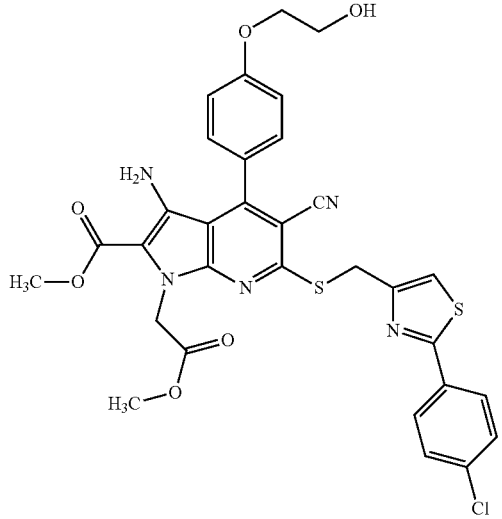<br>(43% of theory) | 2.83 min (Method 2);<br>m/z = 664 | δ (500 MHz) = 7.96 (d, 2H), 7.64 (s, 1H), 7.58 (d, 2H), 7.51 (d, 2H), 7.19 (d, 2H), 5.31 (s, 2H), 4.98-4.89 (m, 3H), 4.73 (s, 2H), 4.12-4.05 (m, 2H), 3.79-3.70 (m, 5H), 3.62 (s, 3H). |
| 3 | 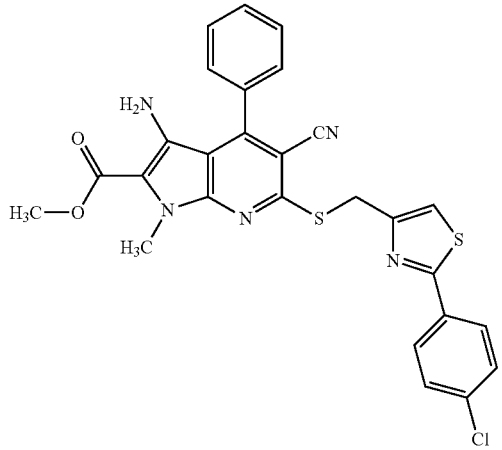<br>(30% of theory) | 4.64 min (Method 7);<br>m/z = 546 | δ (500 MHz) = 7.98 (d, 2H), 7.73 (s, 1H), 7.65-7.60 (m, 3H), 7.59-7.50 (m, 4H), 4.81 (s, 2H), 4.79 (s, 2H), 3.98 (s, 3H), 3.80 (s, 3H). |
| 4 | 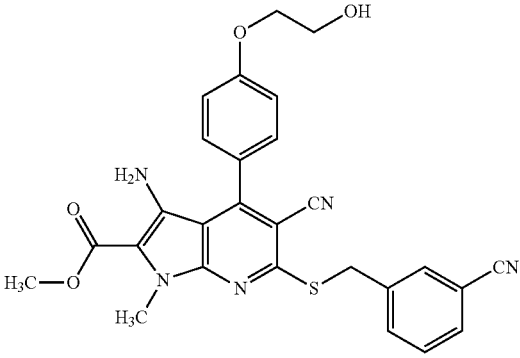<br>(57% of theory) | 1.64 min (Method 4);<br>m/z = 514 | δ (400 MHz) = 8.02 (s, 1H), 7.88 (d, 1H), 7.73 (d, 1H), 7.56 (t, 1H), 7.48 (d, 2H), 7.16 (d, 2H), 5.01-4.82 (m, 3H), 4.68 (s, 2H), 4.09 (t, 2H), 3.95 (s, 3H), 3.80 (s, 3H), 3.78 (t, 2H). |

TABLE 4-continued
| Example No. | Structure (yield) | LC-MS: R$_t$ [min] (Method); MS (ESI): m/z [M + H]$^+$ | $^1$H-NMR (DMSO-d$_6$): |
|---|---|---|---|
| 5 | 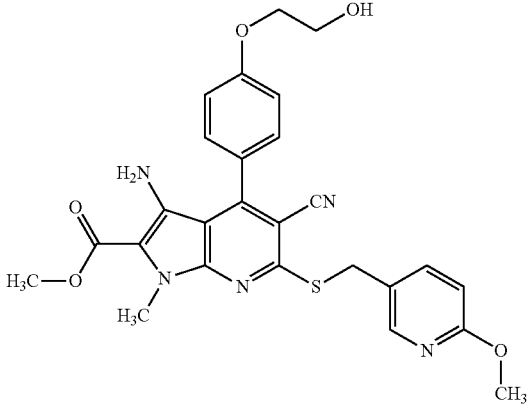<br>(29% of theory) | 2.64 min (Method 3); m/z = 520 | δ (400 MHz) = 8.30 (d, 1H), 7.84 (dd, 1H), 7.48 (d, 2H), 7.18 (d, 2H), 6.80 (d, 1H), 5.10-4.78 (m, 3H), 4.59 (s, 2H), 4.09 (t, 2H), 3.98 (s, 3H), 3.81 (s, 6H), 3.78 (t, 2H). |
| 6 | 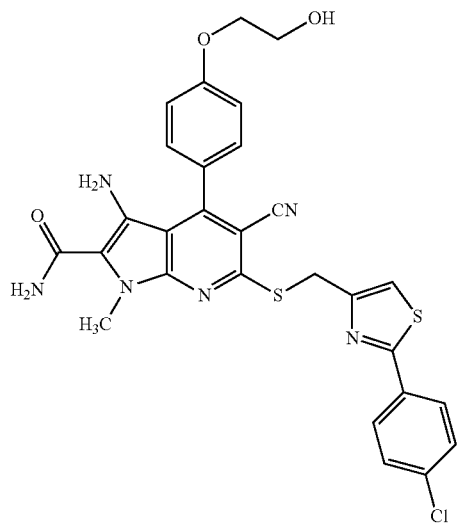<br>(10% of theory) | 2.69 min (Method 3); m/z = 591 | δ (400 MHz) = 7.97 (d, 2H), 7.71 (s, 1H), 7.58 (d, 2H), 7.48 (d, 2H), 7.32 (s, 2H), 7.14 (d, 2H), 4.79 (s, 2H), 4.55-4.28 (s, 2H), 4.09 (t, 2H), 3.92 (s, 3H), 3.76 (t, 2H). |
| 7 | 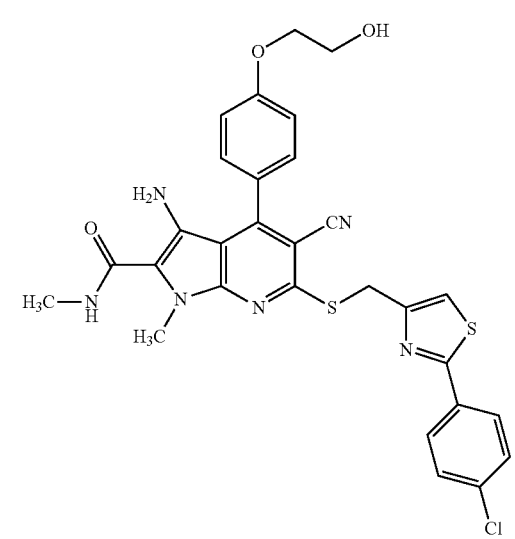<br>(3% of theory) | 3.70 min (Method 4); m/z = 605 | δ (400 MHz) = 8.02-7.92 (m, 3H), 7.70 (s, 1H), 7.59 (d, 2H), 7.50 (d, 2H), 7.11 (d, 2H), 5.05-4.80 (s, 1H), 4.61 (s, 2H), 4.39 (s, 2H), 4.09 (t, 2H), 3.76 (t, 2H) 3.42 (s, 3H), 2.60 (d, 3H). |

TABLE 4-continued
| Example No. | Structure (yield) | LC-MS: $R_t$ [min] (Method); MS (ESI): m/z [M + H]$^+$ | $^1$H-NMR (DMSO-$d_6$): |
|---|---|---|---|
| 8 | 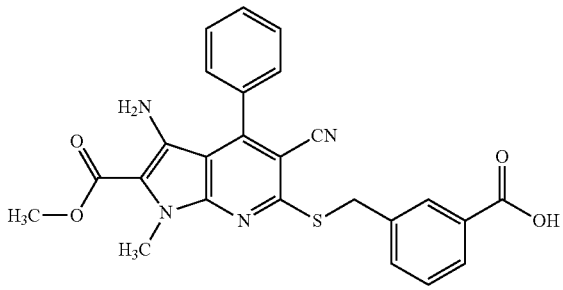<br>(68% of theory) | 3.70 min (Method 7); m/z = 473 | δ (400 MHz) = 13.00 (s, 1H), 8.19 (s, 1H), 7.85-7.77 (m, 2H), 7.65-7.57 (m, 3H), 7.56-7.50 (m, 2H), 7.48 (t, 1H), 4.80 (s, 2H), 4.69 (s, 2H), 3.99 (s, 3H), 3.80 (s, 3H). |
| 9 | 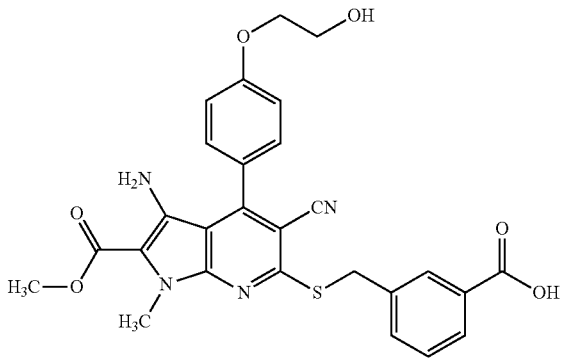<br>(63% of theory) | 2.04 min (Method 8); m/z = 533 | δ (400 MHz) = 12.98 (s, 1H), 8.19 (s, 1H), 7.83-7.76 (m, 2H), 7.49-7.42 (m, 3H), 7.16 (d, 2H), 5.09-4.82 (m, 3H), 4.68 (s, 2H), 4.10 (t, 2H), 3.98 (s, 3H), 3.81 (s, 3H), 3.77 (t, 2H). |
| 10 | 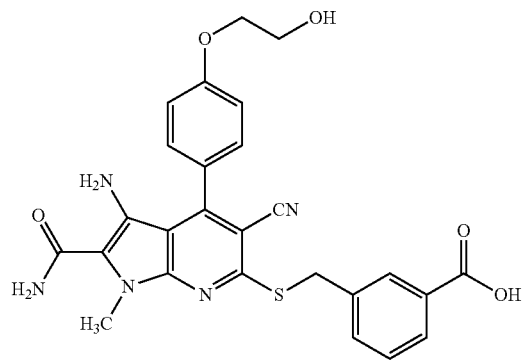<br>(50% of theory) | 1.68 min (Method 8); m/z = 518 | δ (400 MHz) = 12.98 (s, 1H), 12.70-9.10 (br s, 3H), 8.17 (s, 1H), 7.83-7.77 (m, 2H), 7.50-7.41 (m, 3H), 7.32 (s, 1H), 7.13 (d, 2H), 4.68 (s, 2H), 4.40 (s, 1H), 4.10 (t, 2H), 3.93 (s, 3H), 3.76 (t, 2H). |

TABLE 4-continued
| Example No. | Structure (yield) | LC-MS: R$_t$ [min] (Method); MS (ESI): m/z [M + H]$^+$ | $^1$H-NMR (DMSO-d$_6$): |
|---|---|---|---|
| 11 | 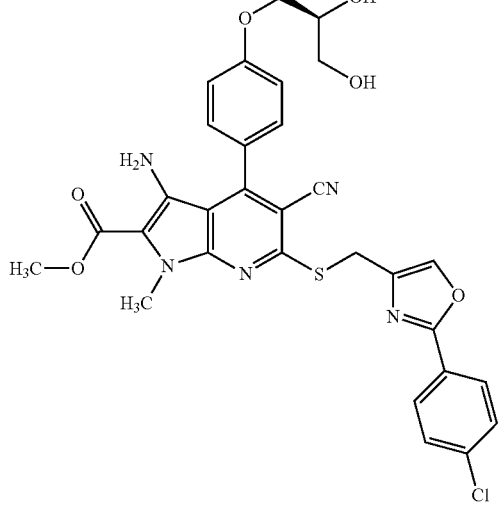<br>(37% of theory) | 2.96 min (Method 3);<br>m/z = 620 | δ (400 MHz) = 8.21 (s, 1H), 7.98 (d, 2H), 7.60 (d, 2H), 7.47 (d, 2H), 7.18 (d, 2H), 5.03 (d, 1H), 4.92 (s, 2H), 4.71 (t, 1H), 4.59 (s, 2H), 4.11 (dd, 1H), 4.01-3.95 (m, 1H), 3.97 (s, 3H), 3.88-3.79 (m, 1H), 3.82 (s, 3H), 3.48 (t, 2H). |
| 12 | 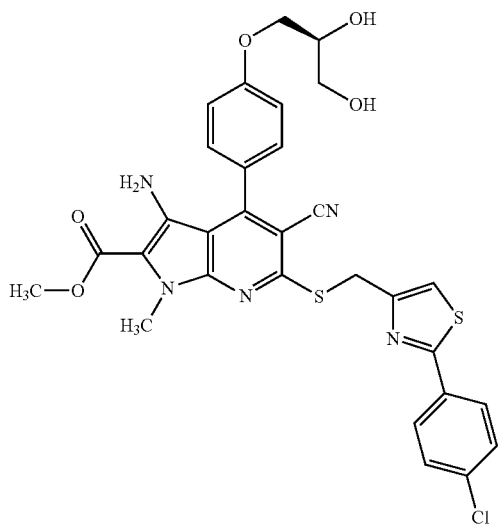<br>(78% of theory) | 4.13 min (Method 7);<br>m/z = 636 | δ (400 MHz) = 7.96 (d, 2H), 7.73 (s, 1H), 7.57 (d, 2H), 7.47 (d, 2H), 7.16 (d, 2H), 5.10-4.97 (br s, 1H), 4.91 (br s, 1H), 4.78 (s, 2H), 4.10 (dd, 1H), 4.01-3.94 (m, 1H), 3.95 (s, 3H), 3.87-3.79 (m, 1H), 3.81 (s, 3 h), 3.48 (d, 2H), NH2 is missing. |

TABLE 4-continued

| Example No. | Structure (yield) | LC-MS: $R_t$ [min] (Method); MS (ESI): m/z [M + H]$^+$ | $^1$H-NMR (DMSO-d$_6$): |
|---|---|---|---|
| 13 | 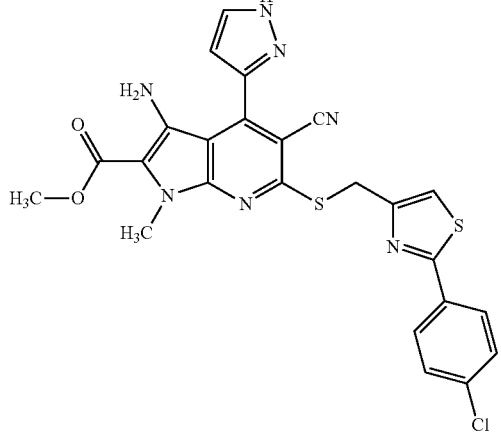<br>(63% of theory) | 1.53 min (Method 6); m/z = 536 | δ (400 MHz) = 13.79 (s, 1H), 8.11 (s, 1H), 7.96 (d, 2H), 7.72 (s, 1H), 7.57 (d, 2H), 6.98 (s, 1H), 6.42 (br s, 2H), 4.78 (s, 2H), 3.94 (s, 3H), 3.82 (s, 3H). |
| 14 | 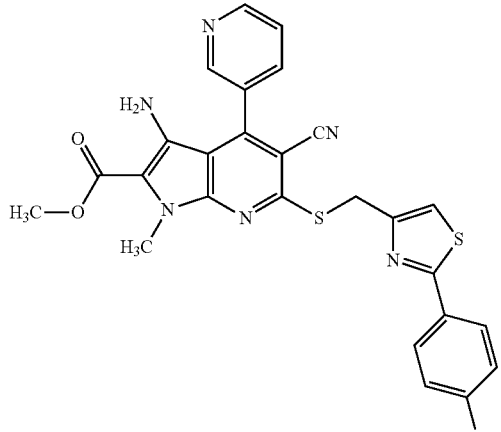<br>(60% of theory) | 3.02 min (Method 3); m/z = 547 | δ (400 MHz) = 8.80 (dd, 1H), 8.76 (d, 1H), 8.03 (d t, 1H), 7.95 (d, 2H), 7.74 (s, 1H), 7.63 (m, 1H), 7.58 (d, 2H), 4.90 (s, 2H), 4.79 (s, 2H), 3.98 (s, 3H), 3.82 (s, 3H). |

Example 15

Methyl 3-amino-6-[(3-carbamoylbenzyl)thio]-5-cyano-4-[4-(2-hydroxyethoxy)phenyl]-1-methyl-1H-pyrrolo[2,3-b]pyridine-2-carboxylate

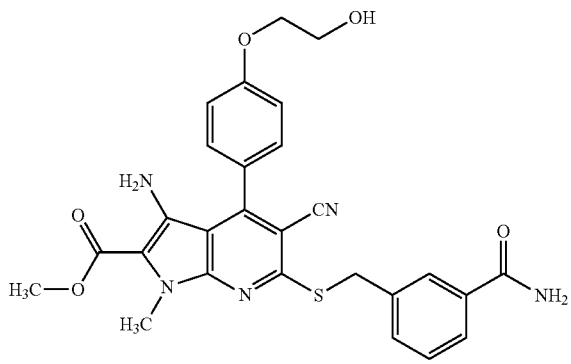 [SMILES: COC(=O)c1c(N)c2c(-c3ccc(OCCO)cc3)c(C#N)c(SCc3cccc(C(N)=O)c3)nc2n1C]

35 mg (0.066 mmol) of the compound from Example 9 were initially charged in 1.5 ml of acetonitrile, and 19 mg (0.1 mmol) of 1-(3-dimethylaminopropyl)-3-ethylcarbodiimide hydrochloride and 13 mg (0.1 mmol) of 1-hydroxy-1H-benzotriazole hydrate were added. After 10 min at RT, 18 mg (0.33 mmol) of ammonium chloride and 0.08 ml (0.46 mmol) of N,N-diisopropylethylamine were added and the mixture was stirred at RT overnight.

Water was added to the reaction mixture until a clear solution had formed. This was purified by preparative HPLC (Chromasil, water/acetonitrile+0.1% TFA).

Yield: 34 mg (97% of theory)

$^1$H-NMR (400 MHz, DMSO-d$_6$): δ=8.09 (s, 1H), 7.98 (s, 1H), 7.76 (d, 1H), 7.68 (d, 1H), 7.49-7.32 (m, 4H), 7.15 (d, 2H), 4.90 (br s, 3H), 4.66 (s, 2H), 4.09 (t, 2H), 3.98 (s, 3H), 3.81 (s, 3H), 3.77 (t, 2H).

LC-MS (Method 8): $R_t$=1.84 min; MS (ESIpos): m/z=532 [M+H]$^+$.

Example 16

3-Amino-6-[(3-carbamoylbenzyl)thio]-5-cyano-4-[4-(2-hydroxyethoxy)phenyl]-1-methyl-1H-pyrrolo[2,3-b]pyridine-2-carboxamide

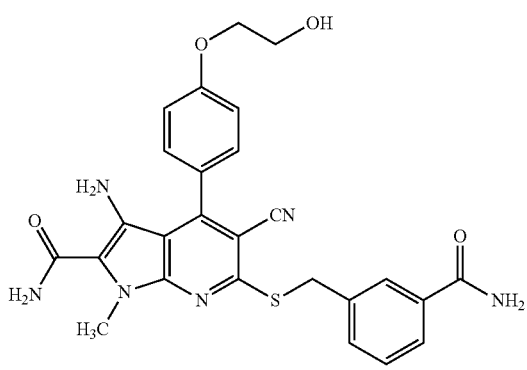 [SMILES: Cn1c(C(N)=O)c(N)c2c(-c3ccc(OCCO)cc3)c(C#N)c(SCc3cccc(C(N)=O)c3)nc21]

The target compound was prepared in a manner analogous to Example 15 from Example 10.

Yield: 2 mg (5% of theory)

$^1$H-NMR (400 MHz, DMSO-$d_6$): δ=8.18 (br s, 2H), 8.08 (s, 1H), 7.97 (s, 1H), 7.77 (d, 1H), 7.68 (d, 1H), 7.48-7.30 (m, 4H), 7.12 (d, 2H), 5.40-4.60 (m, 4H), 4.40 (br s, 1H), 4.09 (t, 2H), 3.93 (s, 3H), 3.77 (t, 2H).

LC-MS (Method 3): $R_t$=1.92 min; MS (ESIpos): m/z=517 [M+H]$^+$.

Example 17

Methyl 3-amino-6-({[2-(4-chlorophenyl)-1,3-thiazol-4-yl]methyl}thio)-5-cyano-4-[4-(2-hydroxyethoxy)phenyl]-1H-pyrrolo[2,3-b]pyridine-2-carboxylate

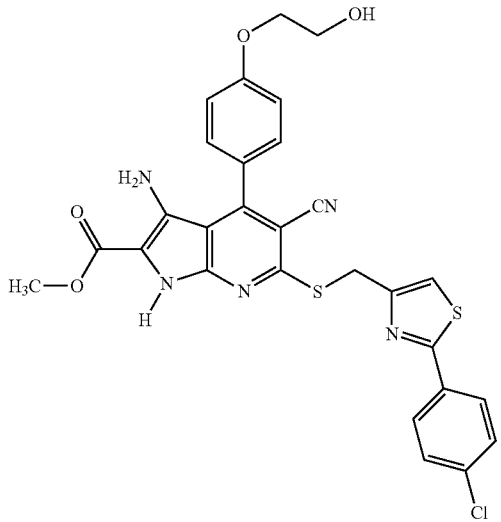 [SMILES: COC(=O)c1[nH]c2nc(SCc3csc(-c4ccc(Cl)cc4)n3)c(C#N)c(-c3ccc(OCCO)cc3)c2c1N]

90 mg (0.114 mmol) of the compound from Example 30A were initially charged in 5 ml of acetonitrile, and 148 mg (0.454 mmol) of cesium carbonate were added. The reaction mixture was stirred at 50° C. overnight, and another 74 mg (0.23 mmol) of cesium carbonate were then added. The mixture was stirred overnight at 50° C., and the solid was then filtered off and washed with acetonitrile. The filtrate was concentrated and the residue (about 200 mg) was reacted further without further purification.

This residue was initially charged in 2 ml of dichloromethane, 2 ml of a 4M solution of hydrogen chloride in 1,4-dioxane were added and the mixture was stirred at RT for 2.5 h. The reaction mixture was evaporated and the residue was purified by preparative HPLC (Chromasil, water/acetonitrile+0.15% conc. hydrochloric acid).

Yield: 5 mg (7% of theory)

$^1$H-NMR (400 MHz, DMSO-$d_6$): δ=12.05 (s, 1H), 8.00 (s, 1H), 7.95 (d, 2H), 7.58 (d, 2H), 7.48 (d, 2H), 7.15 (d, 2H), 4.91 (br s, 1H), 4.74 (s, 2H), 4.70 (s, 2H), 4.09 (t, 2H), 3.81 (s, 3H), 3.77 (t, 2H).

LC-MS (Method 4): $R_t$=4.00 min; MS (ESIpos): m/z=592 [M+H]$^+$.

Example 18

Methyl 3-amino-6-({[2-(4-chlorophenyl)-1,3-thiazol-4-yl]methyl}sulfanyl)-5-cyano-1-methyl-4-piperidin-1-yl-1H-pyrrolo[2,3-b]pyridine-2-carboxylate

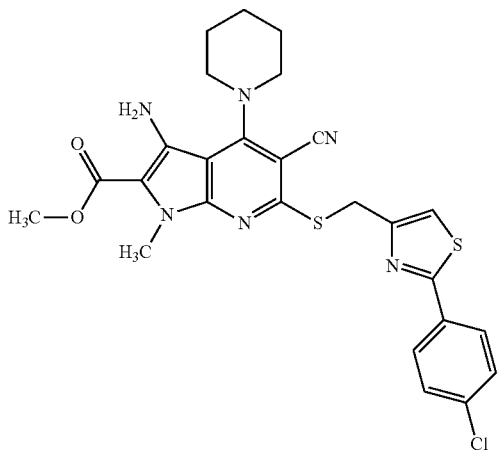 [SMILES: COC(=O)c1c(N)c2c(N3CCCCC3)c(C#N)c(SCc3csc(-c4ccc(Cl)cc4)n3)nc2n1C]

80 mg (0.15 mmol) of the compound from Example 47A were initially charged in 3 ml of acetonitrile, and 189 mg (0.58 mmol) of cesium carbonate were added. The mixture was stirred at 50° C. for 4 h. After cooling, the mixture was filtered and the filtrate was freed from the solvent on a rotary evaporator. The residue was dried under reduced pressure.

Yield: 68 mg (85% of theory)

$^1$H-NMR (400 MHz, CDCl$_3$): δ=7.95 (d, 2H), 7.68 (s, 1H), 7.57 (d, 2H), 5.71 (s, 2H), 4.68 (s, 2H), 3.88 (s, 3H), 3.83 (s, 3H), 3.48-3.42 (m, 4H), 1.76-1.68 (br s, 4H), 1.65-1.57 (m, 2H).

LC-MS (Method 4): $R_t$=5.00 min; MS (ESIpos): m/z=554 [M+H]$^+$.

Example 19

Methyl 3-amino-6-{[2-(4-chlorophenyl)-1,3-oxazol-4-yl]methoxy}-5-cyano-4-[4-(2-hydroxyethoxy)phenyl]-1-methyl-1H-pyrrolo[2,3-b]pyridine-2-carboxylate

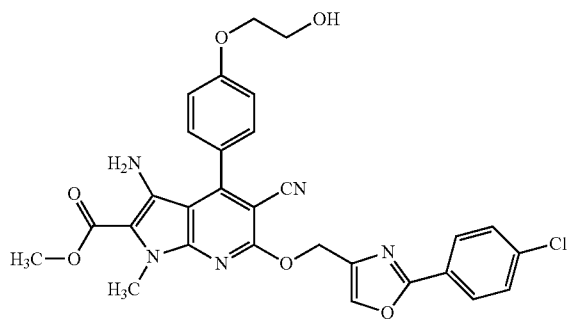 [SMILES: COC(=O)c1c(N)c2c(-c3ccc(OCCO)cc3)c(C#N)c(OCc3coc(-c4ccc(Cl)cc4)n3)nc2n1C]

20 mg (0.04 mmol) of the compound from Example 51A were initially charged in 1 ml of acetonitrile, and 45 mg (0.14 mmol) of cesium carbonate were added. The reaction mixture was stirred at 50° C. for 4 h. After cooling to RT, the mixture was filtered off. The precipitate was washed with acetonitrile and suspended in water. The mixture was extracted three times with in each case 10 ml of ethyl acetate, and the combined organic phases were dried over magnesium sulfate. After removal of the solvent on a rotary evaporator, the residue was purified directly by preparative HPLC (column: YMC GEL ODS-AQ S-5/15 µm; mobile phase gradient: acetonitrile/water 10:90→95:5). Removal of the solvent on a rotary evaporator gave the product as a solid.

Yield: 10 mg (48% of theory).

$^1$H-NMR (400 MHz, DMSO-$d_6$): δ=8.41 (s, 1H), 8.02 (d, 2H), 7.62 (d, 2H), 7.48 (d, 2H), 7.17 (d, 2H), 5.56 (s, 2H), 4.96-4.90 (m, 3H), 4.09 (t, 2H), 3.91 (s, 3H), 3.79 (s, 3H), 3.78 (q, 2H).

LC-MS (Method 6): $R_t$=1.44 min; MS (ESIpos): m/z=574 [M+H]$^+$.

Example 20

Methyl 3-amino-6-({[2-(4-chlorophenyl)-1,3-thiazol-4-yl]methyl}thio)-5-cyano-4-[4-(2-hydroxyethoxy)phenyl]-1-(2-methoxy-2-oxoethyl)-1H-pyrrolo[2,3-b]pyridine-2-carboxylate

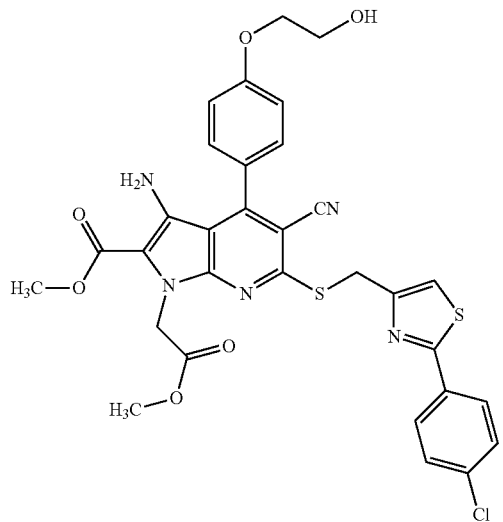 [SMILES: COC(=O)Cn1c(C(=O)OC)c(N)c2c(-c3ccc(OCCO)cc3)c(C#N)c(SCc3csc(-c4ccc(Cl)cc4)n3)nc21]

19 mg (0.024 mmol) of the compound from Example 33A were initially charged in 1 ml of THF, and 0.122 ml (0.122 mmol) of a 1N solution of tetrabutylammonium fluoride in THF were added. The reaction mixture was stirred at RT for 2 h and then diluted with ethyl acetate. The mixture was washed with saturated aqueous sodium bicarbonate solution. The organic phase was dried over sodium sulfate and concentrated, and the residue was purified by preparative HPLC (Chromasil, water/acetonitrile). This gave 15 mg of the product, which were purified by preparative thin-layer chromatography (dichloromethane/methanol=20/1).

Yield: 7 mg (43% of theory)

$^1$H-NMR (500 MHz, DMSO-$d_6$): δ=7.96 (d, 2H), 7.64 (s, 1H), 7.58 (d, 2H), 7.51 (d, 2H), 7.19 (d, 2H), 5.31 (s, 2H), 4.98-4.89 (m, 3H), 4.73 (s, 2H), 4.12-4.05 (m, 2H), 3.79-3.70 (m, 5H), 3.62 (s, 3H).

LC-MS (Method 2): $R_t$=2.83 min; MS (ESIpos): m/z=664 [M+H]$^+$.

Example 21

3-Amino-6-({[2-(4-chlorophenyl)-1,3-thiazol-4-yl]methyl}sulfanyl)-4-[4-(2-hydroxyethoxy)phenyl]-1H-pyrazolo[3,4-b]pyridine-5-carbonitrile

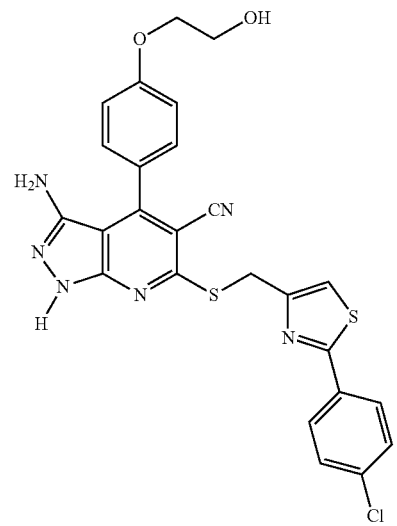 [SMILES: N#Cc1c(SCc2csc(-c3ccc(Cl)cc3)n2)nc2[nH]nc(N)c2c1-c1ccc(OCCO)cc1]

100 mg (0.165 mmol) of the compound from Example 16A were dissolved in 3.2 ml of N-methylpyrrolidone and stirred with 0.20 ml (0.412 mmol) of hydrazine hydrate at RT for 1.5 h. The mixture was diluted with very little acetonitrile, THF and water and purified by preparative HPLC (Chromasil, water/acetonitrile+0.1% TFA).

Yield: 30 mg (34% of theory)

$^1$H-NMR (400 MHz, DMSO-$d_6$): δ=12.81 (br s, 1H), 7.98 (d, 2H), 7.76 (s, 1H), 7.58 (d, 2H), 7.51 (d, 2H), 7.18 (d, 2H), 5.30-4.48 (m, 5H), 4.10 (t, 2H), 3.76 (t, 2H).

LC-MS (Method 3): $R_t$=2.522 min; MS (ESIpos): m/z=535 [M+H]$^+$.

Example 22

3-Amino-6-({[2-(4-chlorophenyl)-1,3-thiazol-4-yl]methyl}sulfanyl)-4-phenyl-1H-pyrazolo[3,4-b]pyridine-5-carbonitrile

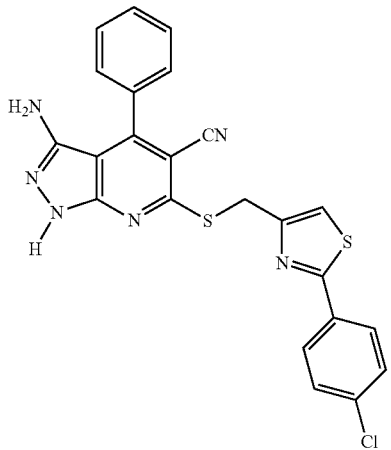 [SMILES: N#Cc1c(SCc2csc(-c3ccc(Cl)cc3)n2)nc2[nH]nc(N)c2c1-c1ccccc1]

The target compound was prepared in a manner analogous to Example 21 from Example 14A.
Yield: 16 mg (20% of theory)
$^1$H-NMR (400 MHz, DMSO-$d_6$): δ=12.88 (br s, 1H), 7.98 (d, 2H), 7.78 (s, 1H), 7.65-7.55 (m, 7H), 5.32-4.42 (m, 4H).
LC-MS (Method 3): $R_t$=2.77 min; MS (ESIpos): m/z=475 [M+H]$^+$.

Example 23

6-({[2-(4-Chlorophenyl)-1,3-thiazol-4-yl]methyl}sulfanyl)-4-[4-(2-hydroxyethoxy)phenyl]-1H-pyrazolo[3,4-b]pyridine-5-carbonitrile

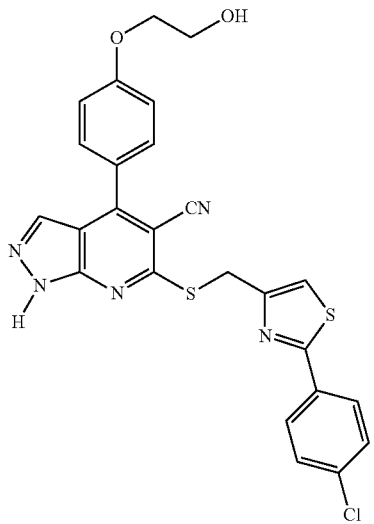 [SMILES: N#Cc1c(SCc2csc(-c3ccc(Cl)cc3)n2)nc2[nH]ncc2c1-c1ccc(OCCO)cc1]

280 mg (0.359 mmol) of the compound from Example 21 were initially charged in 3 ml of water and 6 ml of glacial acetic acid and cooled to 0° C., and a solution of 50 mg of sodium nitrite in 3 ml of water was added. The reaction mixture was stirred at RT overnight. The mixture was then cooled to 0° C., and the precipitate was filtered off. The precipitate was washed with ice-cold water, and 9 ml of 1,2-dimethoxyethane and 12 ml of 0.1N hydrochloric acid solution were added. The reaction mixture was stirred at 80° C. for 1.5 h and then cooled. The mixture was diluted with a small amount of THF such that a clear solution was formed. This was purified a little at a time by preparative HPLC (Chromasil, water/acetonitrile+0.1% TFA).
Yield: 102 mg (55% of theory)
$^1$H-NMR (400 MHz, DMSO-$d_6$): δ=14.18 (s, 1H), 8.11 (s, 1H), 7.97 (d, 2H), 7.78 (s, 1H), 7.74 (d, 2H), 7.58 (d, 2H), 7.19 (d, 2H), 4.99-4.87 (m, 1H), 4.78 (s, 2H), 4.11 (t, 2H), 3.80-3.72 (m, 2H).
LC-MS (Method 4): $R_t$=2.58 min; MS (ESIpos): m/z=520 [M+H]$^+$.

B. Assessing the Pharmacological and Physiological Activity

The pharmacological and physiological activity of the compounds according to the invention can be demonstrated in the following assays:

B-1. Indirect determination of the adenosine agonism by way of gene expression Cells of the CHO (Chinese Hamster Ovary) permanent line are transfected stably with the cDNA for the adenosine receptor subtypes A1, A2a and A2b. The adenosine A1 receptors are coupled to the adenylate cyclase by way of $G_i$ proteins, while the adenosine A2a and A2b receptors are coupled by way of $G_s$ proteins. In correspondence with this, the formation of cAMP in the cell is inhibited or stimulated, respectively. After that, expression of the luciferase is modulated by way of a cAMP-dependent promoter. The luciferase test is optimized, with the aim of high sensitivity and reproducibility, low variance and good suitability for implementation on a robot system, by varying several test parameters, such as cell density, duration of the growth phase and the test incubation, forskolin concentration and medium composition. The following test protocol is used for pharmacologically characterizing cells and for the robot-assisted substance screening:

The stock cultures are grown, at 37° C. and under 5% $CO_2$, in DMEM/F12 medium containing 10% FCS (fetal calf serum) and in each case split 1:10 after 2-3 days. Test cultures are seeded in 384-well plates with 2000 cells per well and grown at 37° C. for approx. 48 hours. The medium is then replaced with a physiological sodium chloride solution (130 mM sodium chloride, 5 mM potassium chloride, 2 mM calcium chloride, 20 mM HEPES, 1 mM magnesium chloride hexahydrate, 5 mM sodium bicarbonate, pH 7.4). The substances to be tested, which are dissolved in DMSO, are pipetted into the test cultures (maximum final concentration of DMSO in the test mixture: 0.5%) in a dilution series of from $5 \times 10^{-11}$M to $3 \times 10^{-6}$M (final concentration). 10 minutes later, forskolin is added to the A1 cells and all the cultures are subsequently incubated at 37° C. for four hours. After that, 35 μl of a solution which is composed of 50% lysis reagent (30 mM disodium hydrogenphosphate, 10% glycerol, 3% TritonX100, 25 mM TrisHCl, 2 mM dithiotreitol (DTT), pH 7.8) and 50% luciferase substrate solution (2.5 mM ATP, 0.5 mM luciferin, 0.1 mM coenzyme A, 10 mM tricine, 1.35 mM magnesium sulfate, 15 mM DTT, pH 7.8) are added to the test cultures, which are shaken for approx. 1 minute and the luciferase activity is measured using a camera system. The $EC_{50}$ values are determined, i.e., the concentrations at which 50% of the luciferase response is inhibited in the case of the A1 cell, and, respectively, 50% of the maximum stimulation with the corresponding substance is achieved in the case of the A2b and A2a cells. The adenosine-analogous compound NECA (5-N-ethylcarboxamidoadenosine), which binds to all adenosine receptor subtypes with high affinity and possesses an agonistic effect, is used in these experiments as the reference compound [Klotz, K. N., Hessling, J., Hegler, J., Owman, C., Kull, B., Fredholm, B. B., Lohse, M. J., "Comparative pharmacology of human adenosine receptor subtypes—characterization of stably transfected receptors in CHO cells", Naunyn Schmiedebergs Arch. Pharmacol., 357, 1-9 (1998)).

Table 1 below lists the $EC_{50}$ values of representative working examples for the receptor stimulation on adenosine A1, A2a and A2b receptor subtypes:

TABLE 1

| Example No. | EC50 A1 [nM] (1 μM forskolin) | EC50 A2a [nM] | EC50 A2b [nM] |
|---|---|---|---|
| 1 | 0.8 | 170 | 550 |
| 2 | 1.7 | 150 | 1540 |
| 3 | 5.3 | >3000 | >3000 |
| 4 | 3.0 | 73 | 320 |
| 5 | 1.5 | 200 | 1000 |
| 6 | 0.3 | 1120 | >3000 |
| 7 | 5.0 | 350 | 660 |
| 11 | 14 | 600 | >3000 |
| 12 | 11 | 1600 | >3000 |
| 15 | 3.7 | 440 | 1330 |
| 16 | 4.9 | 330 | 760 |
| 17 | 3.7 | 680 | >3000 |
| 21 | 10 | >3000 | >3000 |

B-2. Studies on Isolated Blood Vessels

The caudal artery of anesthetized rats is excised and mounted in a conventional apparatus for measuring isolated blood vessels. The vessels are perfused in a heated bath and contracted using phenylephrine. The extent of the contraction is determined using a contraction meter. Test substances are added to the precontracted blood vessels, and the decrease in the contraction of the vessels is measured. A decrease in contraction corresponds to dilation of the vessels. The concentration at which the contraction of the blood vessels is reduced by 50% is given as the $EC_{50}$ value of a test substance with respect to its relaxing properties.

B-3. Measurement of Blood Pressure and Heart Rate on Awake Rats

Various dosages of test substances are administered orally to awake SHR rats (spontaneously hypertensive rats) carrying an internal transmitter capable of measuring permanently both blood pressure and heart rate (telemetric monitoring of hemodynamic parameters). Blood pressure, heart rate and their changes are then recorded over a period of 24 hours.

B-4. Measurement of Blood Pressure and Heart Rate on Awake Marmosets

Various concentrations of test substances are administered orally to awake marmosets which carry an internal transmitter capable of measuring permanently both blood pressure and heart rate (telemetric monitoring of hemodynamic parameters). Blood pressure, heart rate and their changes are then recorded over a period of 6-24 hours.

B-5. Indirect Determination of Adenosine Antagonism Via Gene Expression

Cells of the permanent line CHO K1 (Chinese Hamster Ovary) are stably transfected with a reporter construct (CRE luciferase) and the cDNA for the adenosine receptor subtype A2a or A2b. A2a or A2b receptors are coupled via Gαs proteins to the adenylate cyclase. Through receptor activation, the adenylate cyclase is activated and therefore the cAMP level in the cell increases. Via the reporter construct, a cAMP-dependent promoter, the change in the cAMP level is coupled to luciferase expression. For determination of adenosine antagonism on the adenosine receptor subtype A1, once again CHO K1 cells are stably transfected, but this time with a $Ca^{2+}$-sensitive reporter construct (NFAT-TA-Luc; Clontech) and an A1-Gα16 fusion construct. This receptor chimera is, in contrast to the native A1 receptor (Gαi-coupling), coupled to the phospholipase C. The luciferase is expressed here as a function of the cytosolic $Ca^{2+}$ concentration.

The permanent cell lines are cultured in DMEM/F12 (Cat. No. BE04-687Q; BioWhittaker) with 10% FCS (fetal calf serum) and various additives (20 ml/liter 1M HEPES (Cat. No. 15630; Gibco), 20 ml/liter GlutaMAX (Cat. No. 35050-038, Gibco), 14 ml/liter MEM sodium pyruvate (Cat. No. 11360-039; Gibco) 10 ml/liter PenStrep (Cat. No. 15070-063; Gibco)) at 37° C. under 5% carbon dioxide, and split twice weekly.

For testing in the 384-well plate format, the cells are sown at 2000 cells/well in 25 μl/well sowing medium and cultured at 37° C. under 5% carbon dioxide until substance testing. The A2a and A2b cells are sown, 24 h before substance testing, in medium with additives and 5% FCS, the base medium used for the A2a cells being DMEM/F12 and the base medium used for the A2b cells being OptiMEM (Cat. No. 31985-047; Gibco). The A1-Gα16 cells are sown, 48 h before substance testing, in OptiMEM with 2.5% dialysed FCS and additives. On the day of the test, prior to the addition of the substance, the medium is replaced by 25 μl of Cafty buffer (Cat. No. T21-154; PAA) with 2 mM calcium chloride and 0.1% BSA (bovine serum albumin). Dilution series in Cafty buffer with 2 mM calcium chloride and 0.1% BSA (bovine serum albumin) and a suitable agonist concentration are prepared from the substances to be tested, which are dissolved in DMSO. The substances are pipetted at a final concentration of from $5 \times 10^{-5}$ M to $2.56 \times 10^{-11}$ M to the test cultures, while the DMSO content on the cells should not exceed 0.5%. NECA (5-N-ethyl carboxamidoadenosine) at a final concentration of 30 nM, which roughly corresponds to the $EC_{50}$ concentration, is used as agonist for the A2a and A2b cells. 25 nM CPA (N6-cyclopentyladenosine), which roughly corresponds to the $EC_{75}$ concentration, is used as agonist for the A1-Gα16 cells. After adding the substances, the cell plates are incubated for 3-4 h at 37° C. under 5% carbon dioxide. Then, 25 μl of a solution consisting to 50% of lysis reagent (30 nM disodium hydrogen phosphate, 10% glycerol, 3% Triton X-100, 25 mM TrisHCl, 2 mM dithiothreitol (DTT), pH 7.8) and to 50% of luciferase substrate solution (2.5 mM ATP, 0.5 mM luciferin, 0.1 mM coenzyme A, 10 mM Tricin, 1.35 mM magnesium sulfate, 15 mM DTT, pH 7.8) are added to the cells directly before measurement. The luciferase activity is detected with a luminescence reader. The $IC_{50}$ values are determined, i.e. the concentrations at which the luciferase response, produced by the respective agonist, is inhibited to 50%. ZM241385, for the A2a and A2b cells, and DPCPX (1,3-dipropyl-8-cyclopentylxanthine), for the A1-Gα16 cells, are used as reference antagonist.

C. Working Examples of Pharmaceutical Compositions

The compounds of the invention can be converted into pharmaceutical preparations in the following ways:
Tablet:
Composition:
100 mg of the compound of the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

The mixture of compound of the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.

Suspension which can be administered orally:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol, and the compound of the invention is added to the suspension. The water is added while stirring. The mixture is stirred for about 6 h until the swelling of the Rhodigel is complete.

Solution which can be administered orally:

Composition:

500 mg of the compound of the invention, 2.5 g of polysorbate and 97 g of polyethylene glycol 400.20 g of oral solution correspond to a single dose of 100 mg of the compound of the invention.

Production:

The compound of the invention is suspended in the mixture of polyethylene glycol and polysorbate with stirring. The stirring process is continued until the compound of the invention has completely dissolved.

i.v. Solution:

The compound of the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound of the formula (I)

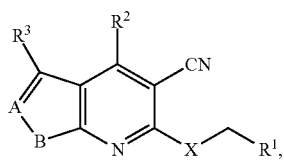

(I)

in which either

A represents $CR^4$ or N, where $R^4$ represents $(C_1-C_4)$-alkoxycarbonyl, aminocarbonyl, mono-$(C_1-C_4)$-alkylaminocarbonyl or di-$(C_1-C_4)$-alkylaminocarbonyl, and B represents $NR^5$, where $R^5$ represents hydrogen or $(C_1-C_4)$-alkyl, in which $(C_1-C_4)$-alkyl may be substituted by a $(C_1-C_4)$-alkoxycarbonyl substituent, or A represents N, and B represents O, X represents O or S, $R^1$ represents $(C_6-C_{10})$-aryl or 5- to 10-membered heteroaryl, where $(C_6-C_{10})$-aryl and 5- to 10-membered heteroaryl may be substituted by 1 or 2 substituents independently of one another selected from the group consisting of halogen, nitro, cyano, $(C_1-C_6)$-alkyl, trifluoromethyl, hydroxyl, $(C_1-C_6)$-alkoxy, amino, mono-$(C_1-C_6)$-alkylamino, di-$(C_1-C_6)$-alkylamino, hydroxycarbonyl, $(C_1-C_6)$-alkoxycarbonyl, aminocarbonyl, mono-$(C_1-C_6)$-alkylaminocarbonyl, di-$(C_1-C_6)$-alkylaminocarbonyl, pyrrolidino, piperidino, morpholino, piperazino and N'-$(C_1-C_4)$-alkylpiperazino, phenyl and 5- or 6-membered heteroaryl, in which phenyl and 5- or 6-membered heteroaryl may be substituted by 1 to 3 substituents independently of one another selected from the group consisting of halogen, nitro, cyano, $(C_1-C_6)$-alkyl, difluoromethyl, trifluoromethyl, hydroxyl, $(C_1-C_6)$-alkoxy, difluoromethoxy, trifluoromethoxy, amino, mono-$(C_1-C_6)$-alkylamino, di-$(C_1-C_6)$-alkyl-amino, hydroxycarbonyl and $(C_1-C_6)$-alkoxycarbonyl, $R^2$ represents $(C_5-C_6)$-cycloalkyl, 5- or 6-membered heterocyclyl, phenyl or 5- or 6-membered heteroaryl, where $(C_5-C_6)$-cycloalkyl may be substituted by 1 or 2 substituents independently of one another selected from the group consisting of $(C_1-C_6)$-alkyl, hydroxyl, oxo, $(C_1-C_6)$-alkoxy, amino, mono-$(C_1-C_6)$-alkylamino and di-$(C_1-C_6)$-alkylamino, in which $(C_1-C_6)$-alkyl and $(C_1-C_6)$-alkoxy may be substituted by 1 or 2 substituents independently of one another selected from the group consisting of hydroxyl, $(C_1-C_4)$-alkoxy and $(C_3-C_7)$-cycloalkyl, in which $(C_3-C_7)$-cycloalkyl for its part may be substituted by 1 or 2 substituents independently of one another selected from the group consisting of $(C_1-C_4)$-alkyl, hydroxyl, oxo and $(C_1-C_4)$-alkoxy, and where 5- or 6-membered heterocyclyl may be substituted by 1 to 3 substituents independently of one another selected from the group consisting of oxo, thioxo, hydroxyl, $(C_1-C_6)$-alkyl, $(C_1-C_6)$-alkoxy, $(C_1-C_6)$-alkylcarbonyl, amino, mono-$(C_1-C_6)$-alkylamino, di-$(C_1-C_6)$-alkylamino and $(C_3-C_7)$-cycloalkyl, in which $(C_1-C_6)$-alkyl may be substituted by 1 to 3 substituents independently of one another selected from the group consisting of fluorine, oxo, hydroxyl, trifluoromethyl, $(C_1-C_4)$-alkoxy, $(C_1-C_4)$-alkylcarbonyloxy, amino, mono-$(C_1-C_4)$-alkylamino, di-$(C_1-C_4)$-alkylamino and $(C_3-C_7)$-cycloalkyl, in which $(C_3-C_7)$-cycloalkyl for its part may be substituted by 1 or 2 substituents independently of one another selected from the group consisting of $(C_1-C_4)$-alkyl, hydroxyl, oxo and $(C_1-C_4)$-alkoxy, and in which $(C_1-C_6)$-alkylcarbonyl may be substituted by a substituent selected from the group consisting of hydroxyl and $(C_1-C_4)$-alkoxy, and in which $(C_3-C_7)$-cycloalkyl may be substituted by 1 or 2 substituents independently of one another selected from the group consisting of $(C_1-C_4)$-alkyl, hydroxyl, oxo and $(C_1-C_4)$-alkoxy, and
where phenyl and 5- or 6-membered heteroaryl may be substituted by 1 to 3 substituents independently of one another selected from the group consisting of halogen, cyano, hydroxyl, $(C_1-C_6)$-alkyl, $(C_1-C_6)$-alkoxy, $(C_3-C_7)$-cycloalkoxy and —$NR^A R^B$, in which $(C_1-C_6)$-alkyl may be substituted by 1 to 3 substituents selected from the group consisting of fluorine, and in which $(C_1-C_6)$-alkoxy may be substituted by 1 to 3 substituents independently of one another selected from the group consisting of fluorine, trifluoromethyl, $(C_3-C_7)$-cycloalkyl, oxo, hydroxyl, $(C_1-C_4)$-alkoxy, hydroxycarbonyl, amino, mono-$(C_1-C_4)$-alkylamino and di-$(C_1-C_4)$-alkylamino, and in which $(C_3-C_7)$-cycloalkoxy may be substituted by 1 or 2 substituents independently of one another selected from the group consisting of $(C_1-C_4)$-alkyl, hydroxyl, oxo and $(C_1-C_4)$-alkoxy, and in which $R^A$ represents hydrogen or $(C_1-C_6)$-alkyl, in which $(C_1-C_6)$-alkyl for its part may be substituted by a substituent selected from the group consisting of hydroxyl and $(C_1-C_4)$-alkoxy, $R^B$ represents hydrogen, $(C_1-C_6)$-alkyl, $(C_3-C_7)$-cycloalkyl, $(C_1-C_4)$-alkylsulfonyl or $(C_3-C_7)$-cycloalkylsulfonyl, in which $(C_1-C_6)$-alkyl for its part may be substituted by 1 or 2 substituents independently of one another selected from the group consisting of $(C_3-C_7)$-cycloalkyl, oxo, hydroxyl, $(C_1-C_4)$-alkoxy, hydroxycarbonyl, amino, mono-$(C_1-C_4)$-alkylamino and di-$(C_1-C_4)$-alkylamino, and in which $(C_3-C_7)$-cycloalkyl for its part may be substituted by 1 or 2 substituents independently of one another selected from the group consisting of $(C_1-C_4)$-alkyl, hydroxyl, oxo and $(C_1-C_4)$-alkoxy, or in which two adjacent substituents at the phenyl together with the carbon atoms to which they are attached may form a 1,3-dioxolane or 2,2-difluoro-1,3-dioxolane, $R^3$ represents hydrogen, $(C_1-C_4)$-alkyl, $(C_1-C_4)$-alkoxy, amino, mono-$(C_1-C_4)$-alkylamino, di-$(C_1-C_4)$-alkylamino or $(C_1-C_4)$-alkylcarbonyl or an N-oxide, salt, or salt of the N-oxide thereof.

2. The compound of the formula (I) as claimed in claim 1 in which

A represents $CR^4$ or N, where $R^4$ represents $(C_1-C_4)$-alkoxycarbonyl, aminocarbonyl or mono-$(C_1-C_4)$-alkylaminocarbonyl, and B represents $NR^5$, where $R^5$ represents hydrogen, methyl or ethyl, in which methyl and ethyl may be substituted by a substituent selected from the group consisting of methoxycarbonyl and ethoxycarbonyl, X represents O or S, $R^1$ represents phenyl or 5- or 6-membered heteroaryl, where phenyl and 5- or 6-membered heteroaryl may be substituted by 1 or 2 substituents independently of one another selected from the group consisting of fluorine, chlorine, cyano, $(C_1-C_4)$-alkyl, trifluoromethyl, hydroxyl, $(C_1-C_4)$-alkoxy, amino, hydroxycarbonyl, $(C_1-C_4)$-alkoxycarbonyl, aminocarbonyl, phenyl and 5- or 6-membered heteroaryl, in which phenyl and 5- or 6-membered heteroaryl may be substituted by 1 to 3 substituents independently of one another selected from the group consisting of fluorine, chlorine, nitro, cyano, $(C_1-C_4)$-alkyl, difluoromethyl, trifluoromethyl, hydroxyl, methoxy, ethoxy, amino, hydroxycarbonyl and $(C_1-C_4)$-alkoxycarbonyl, $R^2$ represents cyclohexyl, tetrahydropyranyl, piperidinyl, piperazinyl, morpholinyl, phenyl, pyrazolyl, imidazolyl, oxazolyl, thiazolyl or pyridyl, where cyclohexyl may be substituted by a substituent selected from the group consisting of hydroxyl and $(C_1-C_4)$-alkoxy, in which $(C_2-C_4)$-alkoxy may be substituted by 1 or 2 substituents independently of one another selected from the group consisting of hydroxyl and methoxy, and where piperidinyl, piperazinyl and morpholinyl may be substituted by a substituent selected from the group consisting of $(C_1-C_4)$-alkyl, hydroxyl, $(C_1-C_4)$-alkoxy and $(C_1-C_4)$-alkylcarbonyl, in which $(C_1-C_4)$-alkyl may be substituted by 1 or 2 substituents independently of one another selected from the group consisting of hydroxyl, methoxy, ethoxy, methylcarbonyloxy and ethylcarbonyloxy, and in which $(C_1-C_4)$-alkylcarbonyl may be substituted by a substituent selected from the group consisting of hydroxyl, methoxy and ethoxy, and where phenyl and pyridyl may be substituted by 1 to 3 substituents independently of one another selected from the group consisting of fluorine, chlorine, cyano, hydroxyl, $(C_1-C_4)$-alkyl and $(C_1-C_4)$-alkoxy, in which $(C_2-C_4)$-alkoxy may be substituted by 1 or 2 substituents independently of one another selected from the group consisting of oxo, hydroxyl, $(C_1-C_4)$-alkoxy, hydroxycarbonyl and amino, and where pyrazolyl, imidazolyl, oxazolyl and thiazolyl may be substituted by 1 or 2 substituents independently of one another selected from the group consisting of fluorine, chlorine, cyano, hydroxyl, $(C_1-C_4)$-alkyl and $(C_1-C_4)$-alkoxy, in which $(C_2-C_4)$-alkoxy may be substituted by 1 or 2 substituents independently of one another selected from the group consisting of oxo, hydroxyl, $(C_1-C_4)$-alkoxy, hydroxycarbonyl and amino, $R^3$ represents hydrogen, amino, methylamino or dimethylamino.

3. The compound of the formula (I) as claimed in claim 1 in which

A represents $CR^4$ or N, where $R^4$ represents $(C_1-C_4)$-alkoxycarbonyl, aminocarbonyl or mono-$(C_1-C_4)$-alkylaminocarbonyl, and B represents $NR^5$, where $R^5$ represents hydrogen, methyl or ethyl, in which methyl and ethyl may be substituted by a substituent selected from the group consisting of methoxycarbonyl and ethoxycarbonyl, X represents O or S, $R^1$ represents phenyl or 5- or 6-membered heteroaryl, where phenyl and 5- or 6-membered heteroaryl may be substituted by 1 or 2 substituents independently of one another selected from the group consisting of fluorine, chlorine, cyano, $(C_1-C_4)$-alkyl, trifluoromethyl, hydroxyl, $(C_1-C_4)$-alkoxy, amino, hydroxycarbonyl, $(C_1-C_4)$-alkoxycarbonyl, aminocarbonyl, phenyl and 5- or 6-membered heteroaryl, in which phenyl and 5- or 6-membered heteroaryl may be substituted by 1 to 3 substituents independently of one another selected from the group consisting of fluorine, chlorine, nitro, cyano, $(C_1-C_4)$-alkyl, difluoromethyl, trifluoromethyl, hydroxyl, methoxy, ethoxy, amino, hydroxycarbonyl and $(C_1-C_4)$-alkoxycarbonyl, $R^2$ represents a group of the formula

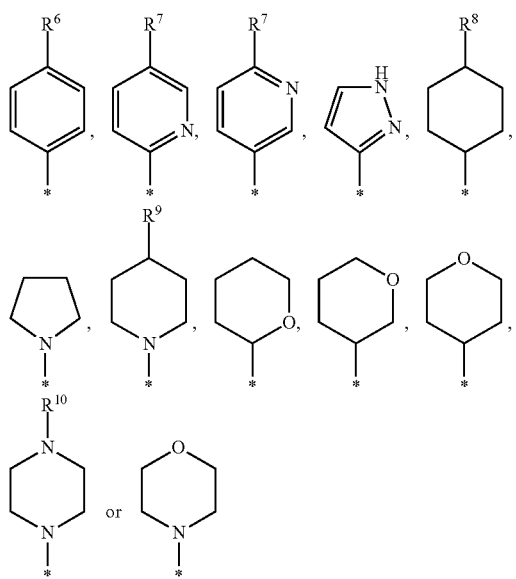

where

* represents the point of attachment to the bicycle, $R^6$ represents hydrogen or $(C_1-C_4)$-alkoxy, in which $(C_2-C_4)$-alkoxy may be substituted by 1 or 2 hydroxyl substituents, $R^7$ represents hydrogen or $(C_1-C_4)$-alkoxy, in which $(C_2-C_4)$-alkoxy may be substituted by 1 or 2 hydroxyl substituents, $R^8$ represents hydrogen, hydroxyl, methoxy, ethoxy or 2-hydroxyethoxy, $R^9$ represents hydrogen or hydroxyl, and $R^{10}$ represents hydrogen or methyl, $R^3$ represents hydrogen, amino, methylamino or dimethylamino.

4. The compound of the formula (I) as claimed in claim 1 in which

A represents $CR^4$ or N, where $R^4$ represents methoxycarbonyl, aminocarbonyl or methylaminocarbonyl, and B represents $NR^5$, where $R^5$ represents hydrogen or methyl, in which methyl may be substituted by a methoxycarbonyl substituent, X represents O or S, $R^1$ represents thiazolyl, oxazolyl, phenyl or pyridyl, where phenyl and pyridyl may be substituted by 1 or 2 substituents independently of one another selected from the group consisting of fluorine, chlorine, cyano, methyl, ethyl, methoxy, amino, hydroxycarbonyl, methoxycarbonyl, ethoxycarbonyl and aminocarbonyl, and where thiazolyl and oxazolyl are substituted by a phenyl group substituent, in which phenyl may be substituted by a substituent selected from the group consisting of fluorine, chlorine, cyano, methyl, methoxy and hydroxycarbonyl, and where thiazolyl and oxazolyl may be substituted by a substituent selected from the group consisting of fluorine, chlorine, cyano, methyl, ethyl, methoxy, amino, hydroxycarbonyl, methoxycarbonyl, ethoxycarbonyl and aminocarbonyl, $R^2$ represents a group of the formula

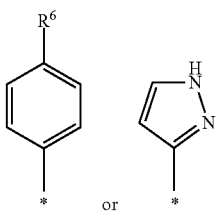

where

* represents the point of attachment to the bicycle, $R^6$ represents hydrogen or $(C_1-C_4)$-alkoxy, in which $(C_2-C_4)$-alkoxy may be substituted by 1 or 2 hydroxyl substituents, $R^3$ represents amino.

5. A process for preparing compounds of the formula (I) as defined in claim 1 and in which $R^3$ represents amino, characterized in that a compound of the formula (II)

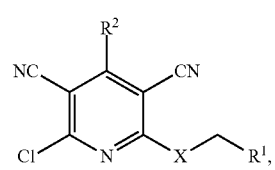

in which X, $R^1$ and $R^2$ each have the meanings given in claim 1,

[A] is reacted in an inert solvent in the presence of a suitable base with a compound of the formula (III-A)

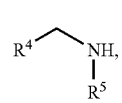

in which $R^4$ and $R^5$ each have the meanings given in claim 1, to give a compound of the formula (IV-A)

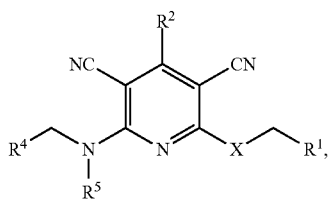

(IV-A)

in which X, R¹, R², R⁴ and R⁵ each have the meanings given in claim 1, and this is then cyclized in an inert solvent and in the presence of a suitable base to give compounds of the formula (I-A)

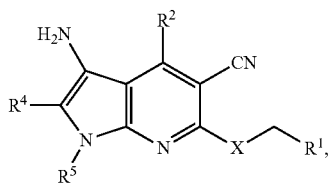

(I-A)

in which X, R¹, R², R⁴ and R⁵ each have the meanings given in claim 1, or

[B] is cyclized in an inert solvent in the presence of a suitable base with a compound of the formula (III-B)

(III-B)

in which R⁵ has the meaning given in claim 1, to give compounds of the formula (I-B)

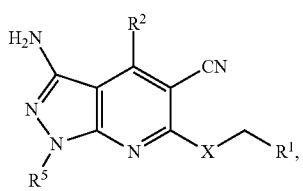

(I-B)

in which X, R¹, R² and R⁵ each have the meanings given in claim 1, or

[C] is reacted in an inert solvent in the presence of a suitable base with the compound of the formula (III-C)

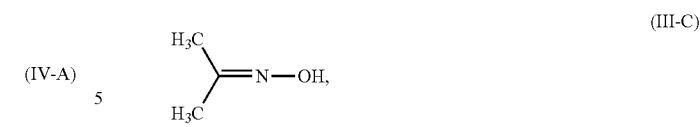

(III-C)

to give a compound of the formula (IV-C)

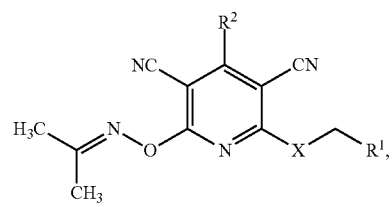

(IV-C)

in which X, R¹ and R² each have the meanings given in claim 1, and this is then cyclized in a suitable solvent in the presence of a suitable base to give compounds of the formula (I-C)

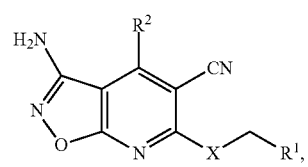

(I-C)

in which X, R¹ and R² each have the meanings given in claim 1, any protective groups present are then cleaved off and the resulting compounds of the formulae (I-A), (I-B) and (I-C) are optionally converted with the appropriate (i) solvents and/or (ii) bases or acids into their salts.

6. A medicament comprising a compound of the formula (I) as defined in claim 1 in combination with an inert, non-toxic, pharmaceutically suitable auxiliary.

7. A medicament comprising a compound of the formula (I) as defined in claim 1 in combination with one or more further active compounds selected from the group consisting of lipid metabolism-modifying active compounds, antidiabetics, antihypertensive drugs and antithrombotic drugs.

8. The medicament as claimed in claim 7 for treating coronary heart disease, acute coronary syndrome, angina pectoris, heart failure, myocardial infarction, atrial fibrillation and hypertension.

9. The medicament as claimed in claim 6 for the treating coronary heart disease, acute coronary syndrome, angina pectoris, heart failure, myocardial infarction, atrial fibrillation and hypertension.

10. A method for treating coronary heart disease, acute coronary syndrome, angina pectoris, heart failure, myocardial infarction, atrial fibrillation and hypertension in humans and animals comprising the step of administering an effective amount of at least one compound of the formula (I) as defined in claim 1.

* * * * *

UNITED STATES PATENT AND TRADEMARK OFFICE
CERTIFICATE OF CORRECTION

| | | |
|---|---|---|
| PATENT NO. | : 8,609,686 B2 | Page 1 of 1 |
| APPLICATION NO. | : 12/809674 | |
| DATED | : December 17, 2013 | |
| INVENTOR(S) | : Nell et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 566 days.

Signed and Sealed this
Twenty-fifth Day of August, 2015

Michelle K. Lee
*Director of the United States Patent and Trademark Office*